United States Patent
Levy et al.

(10) Patent No.: US 11,673,891 B2
(45) Date of Patent: Jun. 13, 2023

(54) IMIDAZOPYRIMIDINE COMPOUNDS AND USES THEREOF

(71) Applicants: Dana-Farber Cancer Institute, Inc., Boston, MA (US); Children's Medical Center Corporation, Boston, MA (US)

(72) Inventors: Ofer Levy, Cambridge, MA (US); David J. Dowling, Brighton, MA (US); Francesco Borriello, Jamaica Plain, MA (US); David A. Scott, Newton, MA (US); Spencer E. Brightman, San Diego, CA (US); Frederic Feru, Boston, MA (US)

(73) Assignees: Dana-Farber Cancer Institute, Inc., Boston, MA (US); Children's Medical Center Corporation, Boston, MA (US)

( * ) Notice: Subject to any disclaimer, the term of this patent is extended or adjusted under 35 U.S.C. 154(b) by 256 days.

(21) Appl. No.: 16/764,171

(22) PCT Filed: Nov. 14, 2018

(86) PCT No.: PCT/US2018/061117
§ 371 (c)(1),
(2) Date: May 14, 2020

(87) PCT Pub. No.: WO2019/099564
PCT Pub. Date: May 23, 2019

(65) Prior Publication Data
US 2022/0242867 A1     Aug. 4, 2022

Related U.S. Application Data

(60) Provisional application No. 62/586,124, filed on Nov. 14, 2017.

(51) Int. Cl.
| | | |
|---|---|---|
| C07D 487/04 | (2006.01) | |
| A61K 31/4188 | (2006.01) | |
| A61K 31/519 | (2006.01) | |
| A61P 37/02 | (2006.01) | |
| A61K 45/06 | (2006.01) | |

(52) U.S. Cl.
CPC .......... *C07D 487/04* (2013.01); *A61K 31/519* (2013.01); *A61K 45/06* (2013.01)

(58) Field of Classification Search
CPC .............. C07D 487/04; A61K 31/4188; A61K 31/519; A61P 37/02
See application file for complete search history.

(56) References Cited

U.S. PATENT DOCUMENTS

| | | | |
|---|---|---|---|
| 5,840,732 A | 11/1998 | Takatani et al. | |
| 6,610,697 B1 | 8/2003 | Dodd et al. | |
| 8,486,945 B2 | 7/2013 | Ivashchenko et al. | |
| 8,507,507 B2 | 8/2013 | Halcomb et al. | |
| 8,871,767 B2 | 10/2014 | Atkinson et al. | |
| 9,617,266 B2 | 4/2017 | Hoelzemann et al. | |
| 9,718,848 B2 | 8/2017 | Adams et al. | |
| 10,676,468 B2 | 6/2020 | Cai et al. | |
| 2003/0176449 A1 | 9/2003 | Blackaby et al. | |
| 2004/0054179 A1 | 3/2004 | Yura et al. | |
| 2006/0040940 A1 | 2/2006 | Bettati et al. | |
| 2007/0037827 A1* | 2/2007 | Nunes .................. | C07D 471/04 544/362 |

(Continued)

FOREIGN PATENT DOCUMENTS

| | | |
|---|---|---|
| CN | 1342162 A | 3/2002 |
| CN | 102666541 | 9/2012 |

(Continued)

OTHER PUBLICATIONS

[No Author Listed] Pubchem 7080208 deposited Jul. 29, 2006. 12 pages. [No Author Listed] Synchrovax SEM Plasmid DNA Vaccine. http://www.violinnet.org/vaxquery/vaccine_detail.php?c_vaccine_id=5506.

Akinbobuyi et al., Synthesis and immunostimulatory activity of substituted TLR7 agonists. Bioorg Med Chem Lett. 2016;26(17):4246-4249.

Awate et al., Mechanisms of action of adjuvants. Front Immunol. 2013;4:114. Published May 16, 2013.

Chuai et al., Poly(I:C)/alum mixed adjuvant priming enhances HBV subunit vaccine-induced immunity in mice when combined with recombinant adenoviral-based HBV vaccine boosting. PLoS One. 2013;8(1):e54126.

(Continued)

*Primary Examiner* — Bruck Kifle
(74) *Attorney, Agent, or Firm* — Wolf, Greenfield & Sacks, P.C.

(57) ABSTRACT

The present disclosure provides compounds of Formula (I), and pharmaceutically acceptable salts, solvates, hydrates, polymorphs, co-crystals, tautomers, stereoisomers, isotopically labeled derivatives, prodrugs, and compositions thereof. The compounds described herein are used as enhancers and/or modifiers of an immune response (e.g., innate and/or adaptive immune response), and are useful in treating and/or preventing a disease, as adjuvants in a vaccine for the disease, (e.g., proliferative disease, inflammatory disease, autoimmune disease, infectious disease, or chronic disease), or as stand alone anti-infective or immune response modifying agents. Also provided in the present disclosure are pharmaceutical compositions, kits, methods, and uses including or using a compound described herein.

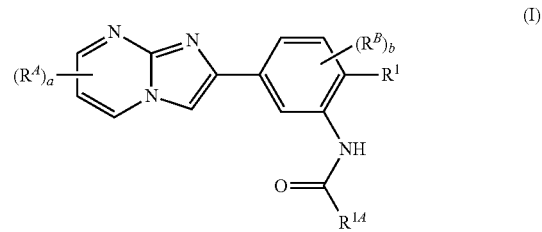

(I)

19 Claims, 13 Drawing Sheets

(56) References Cited

U.S. PATENT DOCUMENTS

| | | |
|---|---|---|
| 2008/0058350 A1 | 3/2008 | Araldi et al. |
| 2008/0167287 A1 | 7/2008 | Zhuo et al. |
| 2010/0075995 A1 | 3/2010 | Biggadike et al. |
| 2010/0168084 A1 | 7/2010 | Huber et al. |
| 2011/0053915 A1 | 3/2011 | Ivaschenko et al. |
| 2011/0098248 A1 | 4/2011 | Halcomb et al. |
| 2011/0263593 A1 | 10/2011 | Bacque et al. |
| 2014/0275119 A1 | 9/2014 | Liang et al. |
| 2014/0322272 A1 | 10/2014 | Garcon-Johnson et al. |
| 2016/0002242 A1 | 1/2016 | Busch et al. |
| 2016/0297827 A1 | 10/2016 | Ali et al. |
| 2016/0326178 A1 | 11/2016 | Zhuo et al. |
| 2016/0361411 A1 | 12/2016 | Gindy et al. |
| 2017/0158724 A1 | 6/2017 | Adams et al. |
| 2017/0197969 A1 | 7/2017 | Pinard et al. |
| 2017/0283454 A1 | 10/2017 | Dubensky, Jr. et al. |
| 2020/0282048 A1 | 9/2020 | Levy et al. |

FOREIGN PATENT DOCUMENTS

| | | |
|---|---|---|
| CN | 103261198 A | 8/2013 |
| CN | 103467590 A | 12/2013 |
| CN | 103570625 A | 2/2014 |
| CN | 105026397 | 11/2015 |
| EP | 2103614 | 9/2009 |
| EP | 2958889 B1 | 3/2017 |
| JP | 2009-503112 A | 1/2009 |
| JP | 2014-500331 A | 1/2014 |
| JP | 2015-526412 A | 9/2015 |
| JP | 2016-503029 A | 2/2016 |
| WO | WO 01/34605 A1 | 5/2001 |
| WO | WO 2001/83485 A1 | 11/2001 |
| WO | WO 2005/089763 A1 | 9/2005 |
| WO | WO 2006/029223 A2 | 3/2006 |
| WO | WO 2006/033703 A1 | 3/2006 |
| WO | WO 2007/019344 A1 | 2/2007 |
| WO | WO 2007/019416 A1 | 2/2007 |
| WO | WO 2007/064902 A2 | 6/2007 |
| WO | WO 2008/027812 A2 | 3/2008 |
| WO | WO 2008/064157 A1 | 5/2008 |
| WO | WO 2012/088411 A1 | 6/2012 |
| WO | WO 2014/012511 A1 | 1/2014 |
| WO | WO 2014/093936 A1 | 6/2014 |
| WO | WO 2014/151729 A1 | 9/2014 |
| WO | WO 2014/151784 A1 | 9/2014 |
| WO | WO 2015/086499 A1 | 6/2015 |
| WO | WO 2015/130584 A2 | 9/2015 |
| WO | WO 2016/148114 A1 | 9/2016 |
| WO | WO 2019/099564 A1 | 5/2019 |
| WO | WO 2019/099578 | 5/2019 |

OTHER PUBLICATIONS

Dyminska, Imidazopyridines as a source of biological activity and their pharmacological potentials—Infrared and Raman spectroscopic evidence of their content in pharmaceuticals and plant materials. Bioorg Med Chem. 2015;23(18):6087-6099.

Haning et al., Comparison of different heterocyclic scaffolds as substrate analog PDE5 inhibitors. Bioorg Med Chem Lett. 2005;15(17):3900-3907.

Humphries et al., 8-Fluoroimidazo[1,2-a]pyridine: Synthesis, physicochemical properties and evaluation as a bioisosteric replacement for imidazo[1,2-a]pyrimidine in an allosteric modulator ligand of the GABAA receptor. Bioorganic & Medicinal Chemistry Letters. 2006:16;1518-1522.

Levy et al., The adenosine system selectively inhibits TLR-mediated TNF-alpha production in the human newborn. J Immunol. 2006;177(3):1956-1966.

Rival et al., Synthesis and antibacterial activity of some imidazo[1,2-a]pyrimidine derivatives. Chem Pharm Bull (Tokyo). 1992;40(5):1170-1176.

Strugnell et al., Understanding Modern Vaccines: Perspectives in Vaccinology. B. V. Netherlands. 2011;1(1).

[No. Author Listed], Stn Database Printout for RN: 847387-52-4. CN: Benzamide, N-(3-imidazo[1,2-a]pyrimidin-2-ylphenyl)-3-methyl-. Entered into STN Database Mar. 2, 20058. Last Accessed Jul. 8, 2022. 33 pages.

[No. Author Listed], Stn Database Printout for RN: 847387-80-8. CN: Benzamide, N-(5-imidazo[1,2-a]pyrimidin-2-yl-2-methylphenyl)-4-methoxy-. Entered into STN Database Mar. 2, 20058. Last accessed Jul. 8, 2022. 17 pages.

[No. Author Listed], Stn Database Printout for RN: 847388-04-9. CN: Benzamide, N-(5-imidazo[1,2-a]pyrimidin-2-yl-2-methoxyphenyl)-3-methoxy-. Entered into STN Database Mar. 2, 20058. Last accessed Jul. 8, 2022. 17 pages.

[No. Author Listed], Stn Database Printout for RN: 862810-49-9. CN: Benzeneacetamide, N-(5-imidazo[1,2-a]pyrimidin-2-yl-2-methylphenyl)-3-methyl-. Entered into STN Database Sep. 9, 2005. Last accessed Jul. 8, 2022. 17 pages.

[No. Author Listed], Stn Database Printout for RN: 862810-99-9. CN: Benzeneacetamide, N-(5-imidazo[1,2-a]pyrimidin-2-yl-2-methoxypheynyl)-. Entered into STN Database Sep. 9, 2005. Last accessed Jul. 8, 2022. 17 pages.

[No. Author Listed], Stn Database Printout for RN: 862811-22-1. CN: Benzamide, N-(4-imidazo[1,2-a]pyrimidin-2-ylphenyl)-3,5-dimethoxy-. Entered into STN Database Sep. 9, 2005. Last accessed Jul. 8, 2022. 17 pages.

[No. Author Listed], Stn Database Printout for RN: 923112-75-8. CN: Benzamide, 4-methyl-N-[4-(7-methylimidazo[1,2-a]pyrimidin-2-yl)phyenyl]-. Entered into STN Database Feb. 2, 20076. Last accessed Jul. 8, 2022. 17 pages.

[No. Author Listed], Stn Database Printout for RN: 923234-58-6. CN: Benzeneacetamide, 4-methoxy-N-[4-(7-methylimidazo[1,2-a]pyrimidin-2-yl)phyenyl]-. Entered into STN Database Feb. 2, 20076. Last accessed Jul. 8, 2022. 17 pages.

[No. Author Listed] Database Stn Registry file, RN:863020-21-7, 863020-23-9, 863020-29-5, [online], Entered STN: Sep. 13, 2005, [retrieved on Sep. 16, 2022].

[No. Author Listed] Database Stn Registry file, RN: 862810-06-8, 862810-83-1, 862810-91-1, 862811-03-8, [online], Entered STN: Sep. 9, 2005, [retrieved on Sep. 16, 2022].

[No. Author Listed] Database Stn Registry file, RN: 847387-50-2, 847387-51-3, 847387-61-5, 847387-73-9, 847387-98-8, 847387-99-9, 847388-07-2, [online], Entered STN: Mar. 28, 2005, [retrieved on Sep. 16, 2022].

[No. Author Listed] Stn Database Printout for PubChem CID: 7080171. CN: 2-bromo-N-(3-imidazo[1,2-a]pyrimidin-2-ylphenyl)benzamide. Entered into STN Database Jul. 2, 20069. Last accessed Nov. 26, 2022. 1 page.

[No. Author Listed] Stn Database Printout for PubChem CID: 6622603. CN: N-(3-(imidazo[1,2-a]pyrimidin-2-yl)phenyl)-2-(trifluoromethyl)benzamide. Entered into STN Database Jun. 5, 2006. Last accessed Nov. 2, 20226. 1 page.

Gao et al., Synthesis and Evaluation of Conjugates of Novel TLR7 Inert Ligands as Self-Adjuvanting Immunopotentiators. ACS Med Chem Lett. Jan. 30, 2015;6(3):249-53. doi: 10.1021/ml5003647.

Jordan, Tamoxifen: a most unlikely pioneering medicine. Nat Rev Drug Discov. Mar. 2003;2(3):205-13.

Young et al., Duplex high-throughput flow cytometry screen identifies two novel formylpeptide receptor family probes. Cytometry A. Mar. 2009;75(3):253-63. doi: 10.1002/cyto.a.20645.

* cited by examiner

IMIDAZOPYRIMIDINE COMPOUNDS AND USES THEREOF

RELATED APPLICATIONS

This application is a National Stage Filing under 35 U.S.C. § 371 of International Application No. PCT/US2018/061117, filed Nov. 14, 2018, which claims the benefit under 35 U.S.C. § 119(e) to U.S. Provisional Application No. 62/586,124, filed Nov. 14, 2017, the entire contents of each of which are incorporated herein by reference.

GOVERNMENT SUPPORT

This disclosure was made with government support under HHSN272201400052C awarded by the National Institutes of Health (NIH) and National Institute of Allergy & Infectious Diseases (NIAID) Contract Adjuvant Discovery Program. The government has certain rights in this invention.

BACKGROUND

Human immunity is crucial to both health and illness, playing key roles in multiple major diseases including infectious diseases, allergy, auto-immunity, cancer and chronic diseases such as cardiovascular disease and diabetes. Animal and human studies suggest that certain small molecules act as immune activators.

SUMMARY

Some aspects of the present disclosure are based, at least in part, on the finding that imidazopyrimidine compounds induce robust activation of human leukocytes in vitro and act as adjuvants in vivo. Accordingly, provided herein are imidazopyrimidine compounds for use in enhancing human immune responses, including innate and adaptive immune responses. In some embodiments, the imidazopyrimidine compounds are used as adjuvants in vaccines. Adjuvants can enhance, prolong, and modulate immune responses to vaccinal antigens to maximize protective immunity. In some aspects, using imidazopyrimidine as vaccine adjuvants enable effective immunization in vulnerable populations (e.g., neonates, infants, the elderly, or immunocompromised individuals). In one aspect, described herein are compounds of Formula (I), and pharmaceutically acceptable salts, solvates, hydrates, polymorphs, co-crystals, tautomers, stereoisomers, isotopically labeled derivatives, and prodrugs thereof. The compounds described herein are enhancers and/or modifiers of an immune response (e.g., innate and/or adaptive immune response). The compounds described herein are adjuvants in a vaccine for a disease, e.g., proliferative disease, inflammatory disease, autoimmune disease, infectious disease, or chronic disease, or as stand alone anti-infective or immune response modifying agents, in a subject in need thereof. Also provided are pharmaceutical compositions, kits, methods, and uses including a compound described herein.

In one aspect, the present disclosure provides compounds of Formula (I):

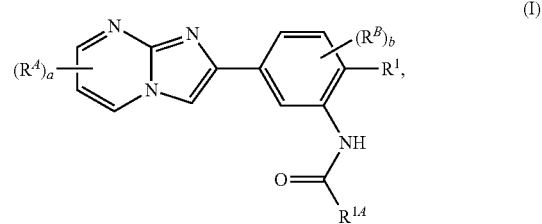

and pharmaceutically acceptable salts, solvates, hydrates, polymorphs, co-crystals, tautomers, stereoisomers, isotopically labeled derivatives, and prodrugs thereof, wherein $R^{1A}$, $R^A$, $R^B$, $R^1$, a, and b are defined herein.

Exemplary compounds of Formula (I) include, but are not limited to:

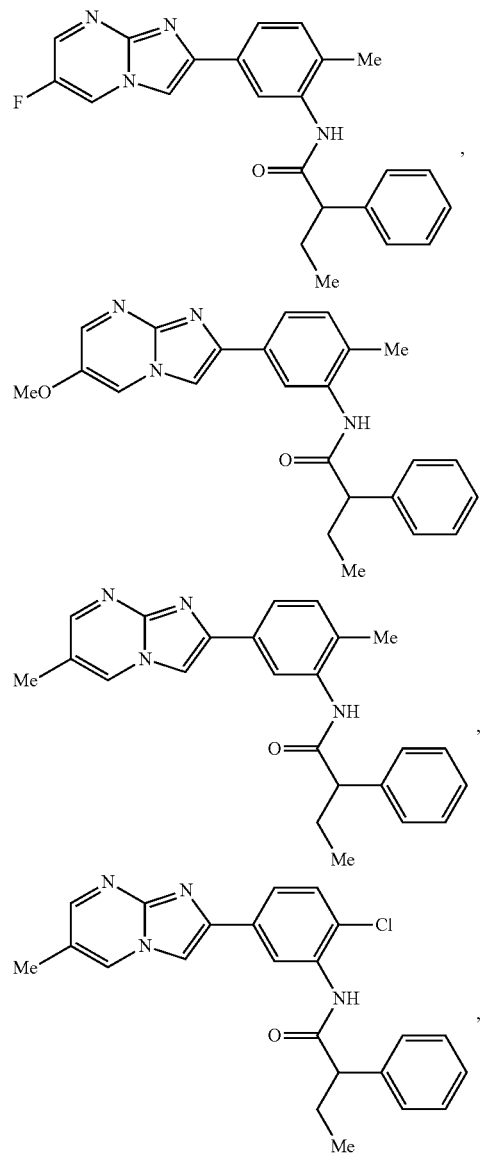

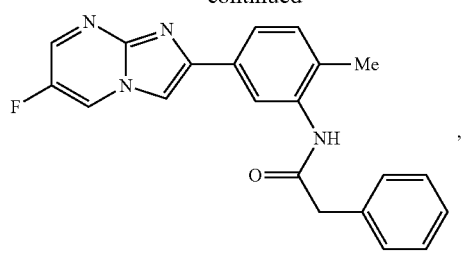,
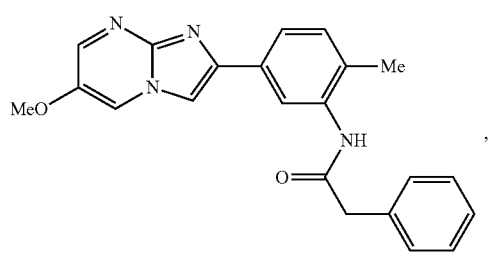,
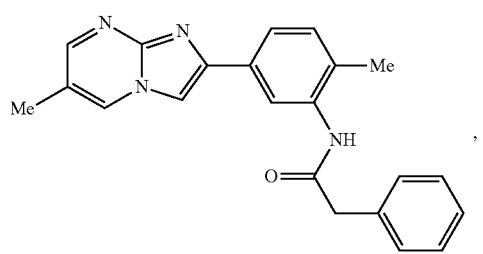,
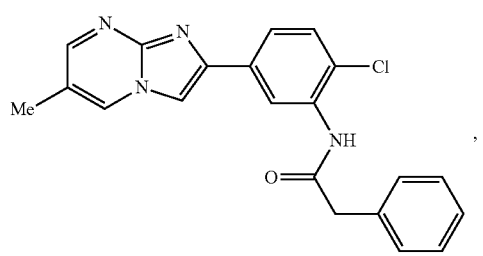,
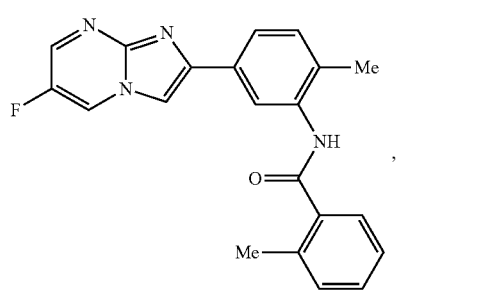,
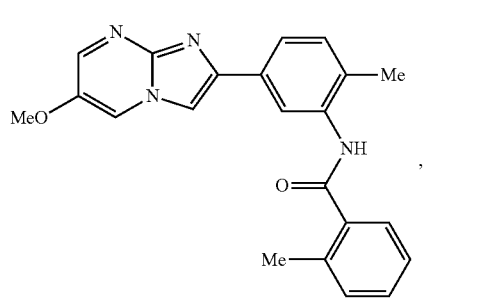,
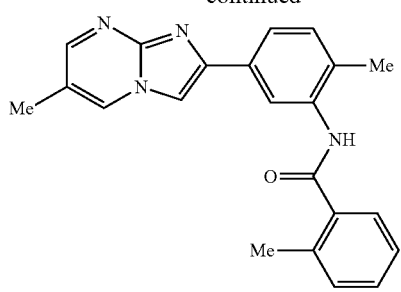,
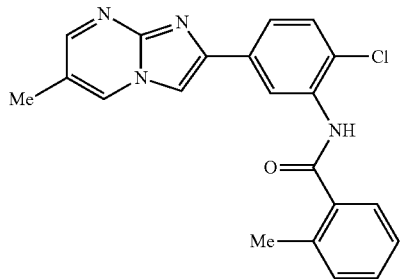,
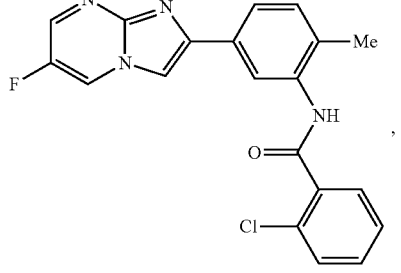,
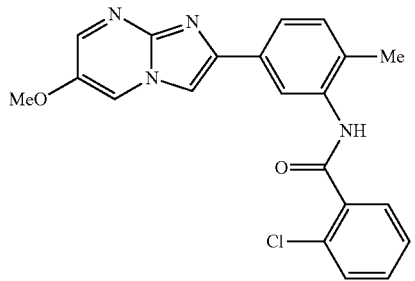,
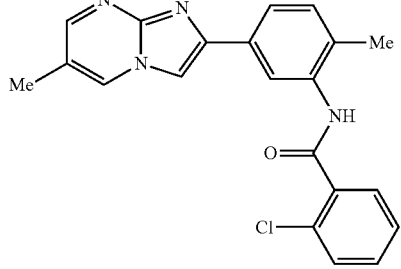,
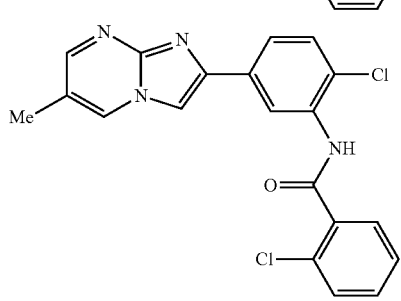,

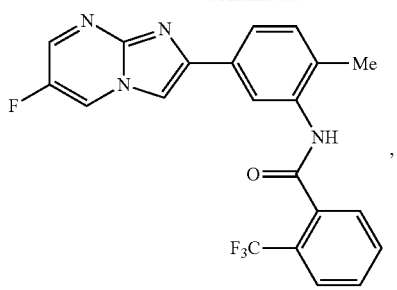
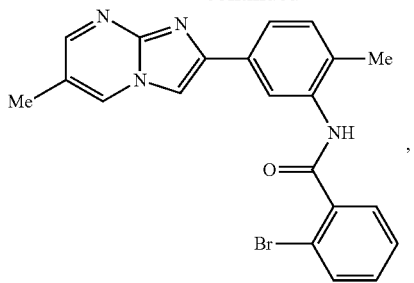
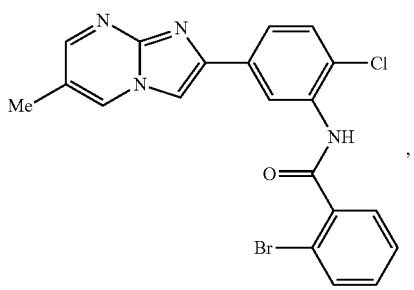
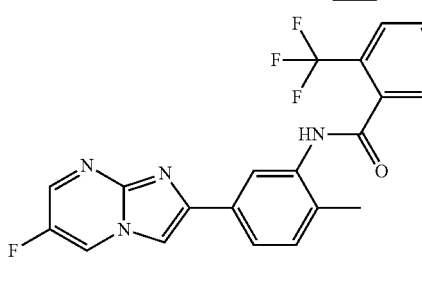
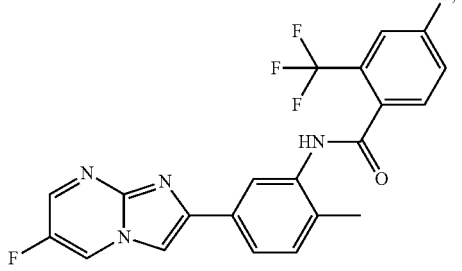
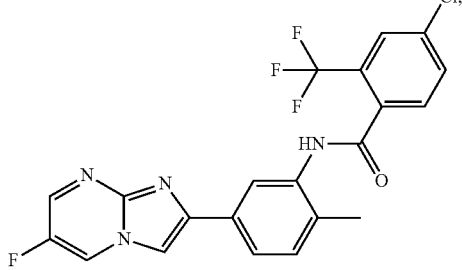
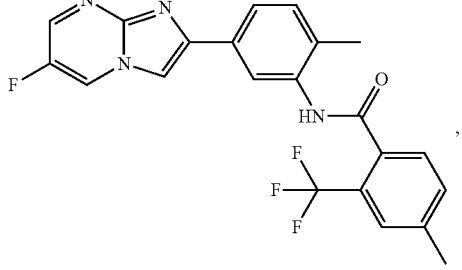

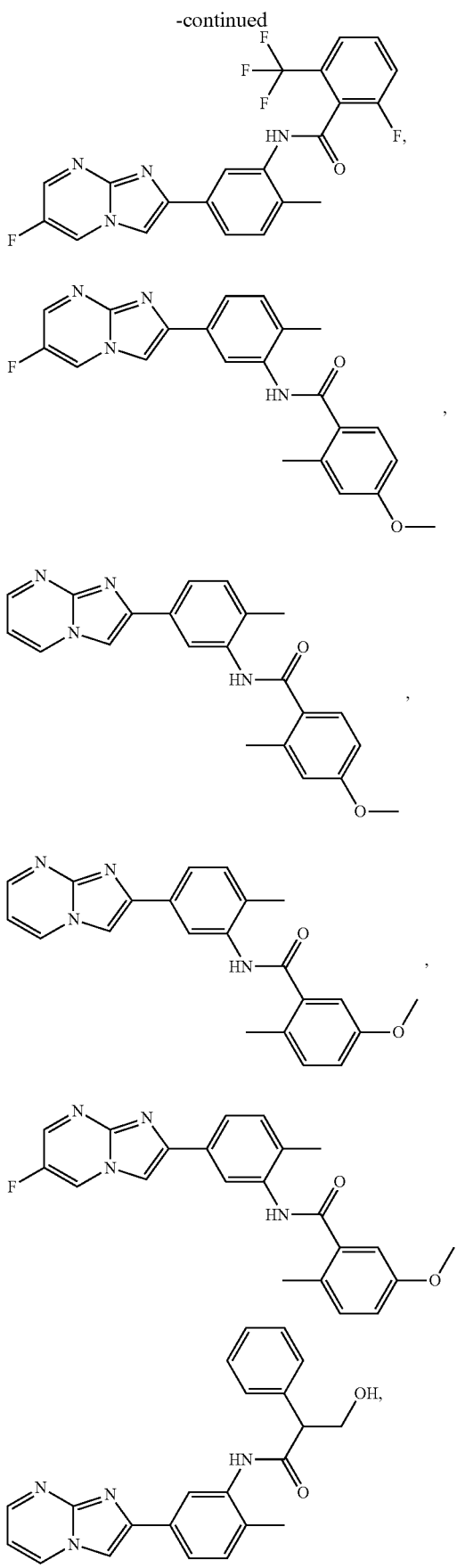

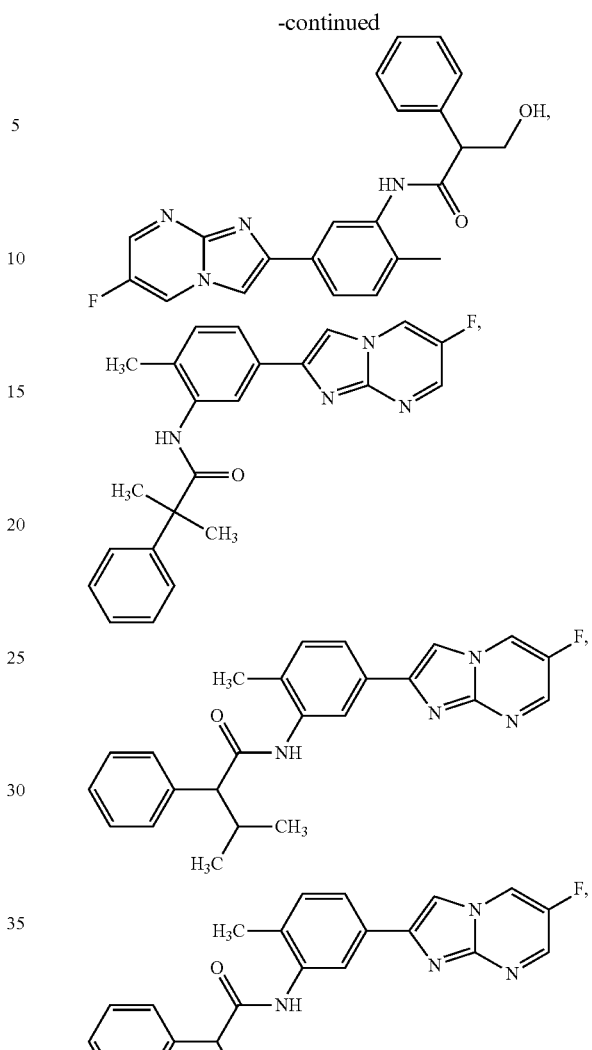

and pharmaceutically acceptable salts, solvates, hydrates, polymorphs, co-crystals, tautomers, stereoisomers, isotopically labeled derivatives, and prodrugs thereof.

In another aspect, described herein are pharmaceutical compositions including a compound described herein, and optionally a pharmaceutically acceptable excipient. In certain embodiments, a pharmaceutical composition described herein includes a therapeutically or prophylactically effective amount of a compound described herein. In certain embodiments, a pharmaceutical composition described herein further comprises an additional pharmaceutical agent. The pharmaceutical compositions may be useful as enhancers and/or modifiers of an immune response (e.g., innate and/or adaptive immune response), and/or adjuvants in a vaccine for a disease, e.g., proliferative disease, inflammatory disease, autoimmune disease, infectious disease, or chronic disease, or as stand alone anti-infective or immune response modifying agents.

In certain embodiments, the subject has any of the diseases described herein (e.g., infectious disease, auto-immune disease, allergy, cancer, or chronic disease). In some embodiments, the subject is at risk of developing any of the diseases described herein (e.g., infectious disease, auto-immune disease, allergy, cancer, or chronic disease). In some embodiments, administering the antigen and the imidazopyrimidine compound described herein to a subject having a disease treats the disease (therapeutic use). In some embodiments, administering the compound described herein to a subject at risk of developing a disease reduces the likelihood (e.g., by 20%, 30%, 40%, 50%, 60%, 70%, 80%, 90%, 95%, 99% or more) of the subject developing the disease (prophylactic use). In certain embodiments, the subject is a human. In some embodiments, the subject is a human neonate. In some embodiments, the subject is a human infant. In some embodiments, the human infant is a neonate that is less than or equal to 28 days of age. In some embodiments, the human infant is 0-28 days, 0-27 days, 0-26 days, 0-25 days, 0-24 days, 0-23 days, 0-22 days, 0-21 days, 0-20 days, 0-19 days, 0-18 days, 0-17 days, 0-16 days, 0-15 days, 0-14 days, 0-13 days, 0-12 days, 0-11 days, 0-10 days, 0-9 days, 0-8 days, 0-7 days, 0-6 days, 0-5 days, 0-4 days, 0-3 days, 0-2 days, 0-1 days, 0-12 hours, 0-6 hours, 0-2 hours, 0-1 hour, 1-28 days, 1-27 days, 1-26 days, 1-25 days, 1-24 days, 1-23 days, 1-22 days, 1-21 days, 1-20 days, 1-19 days, 1-18 days, 1-17 days, 1-16 days, 1-15 days, 1-14 days, 1-13 days, 1-12 days, 1-11 days, 1-10 days, 1-9 days, 1-8 days, 1-7 days, 1-6 days, 1-5 days, 1-4 days, 1-3 days, 1-2 days, 2-28 days, 2-27 days, 2-26 days, 2-25 days, 2-24 days, 2-23 days, 2-22 days, 2-21 days, 2-20 days, 2-19 days, 2-18 days, 2-17 days, 2-16 days, 2-15 days, 2-14 days, 2-13 days, 2-12 days, 2-11 days, 2-10 days, 2-9 days, 2-8 days, 2-7 days, 2-6 days, 2-5 days, 2-4 days, 2-3 days, 3-28 days, 3-27 days, 3-26 days, 3-25 days, 3-24 days, 3-23 days, 3-22 days, 3-21 days, 3-20 days, 3-19 days, 3-18 days, 3-17 days, 3-16 days, 3-15 days, 3-14 days, 3-13 days, 3-12 days, 3-11 days, 3-10 days, 3-9 days, 3-8 days, 3-7 days, 3-6 days, 3-5 days, 3-4 days, 4-28 days, 4-27 days, 4-26 days, 4-25 days, 4-24 days, 4-23 days, 4-22 days, 4-21 days, 4-20 days, 4-19 days, 4-18 days, 4-17 days, 4-16 days, 4-15 days, 4-14 days, 4-13 days, 4-12 days, 4-11 days, 4-10 days, 4-9 days, 4-8 days, 4-7 days, 4-6 days, 4-5 days, 5-28 days, 5-27 days, 5-26 days, 5-25 days, 5-24 days, 5-23 days, 5-22 days, 5-21 days, 5-20 days, 5-19 days, 5-18 days, 5-17 days, 5-16 days, 5-15 days, 5-14 days, 5-13 days, 5-12 days, 5-11 days, 5-10 days, 5-9 days, 5-8 days, 5-7 days, 5-6 days, 6-28 days, 6-27 days, 6-26 days, 6-25 days, 6-24 days, 6-23 days, 6-22 days, 6-21 days, 6-20 days, 6-19 days, 6-18 days, 6-17 days, 6-16 days, 6-15 days, 6-14 days, 6-13 days, 6-12 days, 6-11 days, 6-10 days, 6-9 days, 6-8 days, 6-7 days, 7-28 days, 7-27 days, 7-26 days, 7-25 days, 7-24 days, 7-23 days, 7-22 days, 7-21 days, 7-20 days, 7-19 days, 7-18 days, 7-17 days, 7-16 days, 7-15 days, 7-14 days, 7-13 days, 7-12 days, 7-11 days, 7-10 days, 7-9 days, 7-8 days, 9-28 days, 9-27 days, 9-26 days, 9-25 days, 9-24 days, 9-23 days, 9-22 days, 9-21 days, 9-20 days, 9-19 days, 9-18 days, 9-17 days, 9-16 days, 9-15 days, 9-14 days, 9-13 days, 9-12 days, 9-11 days, 9-10 days, 10-28 days, 10-27 days, 10-26 days, 10-25 days, 10-24 days, 10-23 days, 10-22 days, 10-21 days, 10-20 days, 10-19 days, 10-18 days, 10-17 days, 10-16 days, 10-15 days, 10-14 days, 10-13 days, 10-12 days, 10-11 days, 11-28 days, 11-27 days, 11-26 days, 11-25 days, 11-24 days, 11-23 days, 11-22 days, 11-21 days, 11-20 days, 11-19 days, 11-18 days, 11-17 days, 11-16 days, 11-15 days, 11-14 days, 11-13 days, 11-12 days, 12-28 days, 12-27 days, 12-26 days, 12-25 days, 12-24 days, 12-23 days, 12-22 days, 12-21 days, 12-20 days, 12-19 days, 12-18 days, 12-17 days, 12-16 days, 12-15 days, 12-14 days, 12-13 days, 13-28 days, 13-27 days, 13-26 days, 13-25 days, 13-24 days, 13-23 days, 13-22 days, 13-21 days, 13-20 days, 13-19 days, 13-18 days, 13-17 days, 13-16 days, 13-15 days, 13-14 days, 14-28 days, 14-27 days, 14-26 days, 14-25 days, 14-24 days, 14-23 days, 14-22 days, 14-21 days, 14-20 days, 14-19 days, 14-18 days, 14-17 days, 14-16 days, 14-15 days, 15-28 days, 15-27 days, 15-26 days, 15-25 days, 15-24 days, 15-23 days, 15-22 days, 15-21 days, 15-20 days, 15-19 days, 15-18 days, 15-17 days, 15-16 days, 16-28 days, 16-27 days, 16-26 days, 16-25 days, 16-24 days, 16-23 days, 16-22 days, 16-21 days, 16-20 days, 16-19 days, 16-18 days, 16-17 days, 17-28 days, 17-27 days, 17-26 days, 17-25 days, 17-24 days, 17-23 days, 17-22 days, 17-21 days, 17-20 days, 17-19 days, 17-18 days, 18-28 days, 18-27 days, 18-26 days, 18-25 days, 18-24 days, 18-23 days, 18-22 days, 18-21 days, 18-20 days, 18-19 days, 19-28 days, 19-27 days, 19-26 days, 19-25 days, 19-24 days, 19-23 days, 19-22 days, 19-21 days, 19-20 days, 20-28 days, 20-27 days, 20-26 days, 20-25 days, 20-24 days, 20-23 days, 20-22 days, 20-21 days, 21-28 days, 21-27 days, 21-26 days, 21-25 days, 21-24 days, 21-23 days, 21-22 days, 22-28 days, 22-27 days, 22-26 days, 22-25 days, 22-24 days, 22-23 days, 23-28 days, 23-27 days, 23-26 days, 23-25 days, 23-24 days, 24-28 days, 24-27 days, 24-26 days, 24-25 days, 25-28 days, 25-27 days, 25-26 days, 26-28 days, 26-27 days, or 27-28 days of age. In some embodiments, the human infant is less than 28 days of age at the time of administration (vaccination). In some embodiments, the human infant is less than 4 days of age at the time of administration (vaccination). In some embodiments, the human infant is less than 2 days of age at the time of administration (vaccination). In some embodiments, the human infant is less than 24 days of age at the time of administration (vaccination). In some embodiments, the administration (vaccination) occurs at birth. In some embodiments, a second administration occurs when the subject is less than or equal to 28 days of age. In some embodiments, a second administration occurs when the subject is less than 6 months of age. In some embodiments, the human subject is a human neonate (e.g., less than 28 days of age) that receives 1 or 2 doses of the vaccine described herein. In some embodiments, the human neonate receives one dose before 28-days of age (e.g., 2, 3, 4, 5, 6, 7, 8, 9, 10, 11, 12, 13, 14, 15, 16, 17, 18, 19, 20 days of age) and a second dose before or at 28-days of age. In some embodiments, the human subject receives one dose at 2 months, 4 months, 6 months, 9 months or 12 months of age, and a second dose after the first dose at 2 months, 4 months, 6 months, 9 months or 12 months of age. In some embodiments, a human subject receives a second dose before or equal to 12-months of age (e.g., 1, 2, 3, 4, 5, 6, 9, or 12 months of age). In some embodiments, a human subject receives a second dose after 6-months of age (e.g., 1 year, 2 years, 3 years of age). In some embodiments, the human subject is born prematurely or has low birth weight. "Born prematurely" means the human subject is born before 40-weeks of term. In some embodiments, the human subject is born before 37-weeks of term. In some embodiments, the human subject is born before 32 weeks of term. In some embodiments, the human subject is born before 24 weeks of term. In some embodiments, the human subject is born before 40 weeks, 39 weeks, 38 weeks, 37 weeks, 36 weeks, 35 weeks, 34 weeks, 33 weeks, 32 weeks, 31 weeks, 30 weeks, 29 weeks, 28 weeks, 27 weeks, 26 weeks, 25 weeks, or 24 weeks of term. In some embodiments, the human subject is more than 28-days old (e.g., 1 month, 2 months, 3 months, 4 months, 5 months, 6 months, 7 months, 8 months, 9 months, 10 months, 11 months, 12 months, 2 years, 3 years, 4 years, 5 years, 10 years, 11 years, 12 years, 13 years, 14 years, 15 years, 16 years, 17 years old). In some embodiments, the human subject is born with low birth weight (e.g., at least 20% lower than a normal birth weight). In some embodiments, the human subject has an undeveloped (e.g., an infant or a neonate), weak (an elderly individual), or compromised immune system. Immunocompromised subjects include, without limitation, subjects suffering from sepsis, HIV patients, and patients who received radiation (e.g., for the treatment of cancer). In some embodiments, the human subject is an adult (e.g., more than 18 years old). In some embodiments, the human subject is an elderly human (e.g., more than 60 years old). In some embodiments, the human neonate is 1, 2, 3, 4, 5, 6, 7, 8, 9, 10, 11, 12, 13, 14, 15, 16, 17, 18, 19, 20, 21, 22, 23, 24, 25, 26, 27, or 28 days of age at the time of administration of the compound described herein. In some embodiments, the human subject is an infant. In certain embodiments, the subject is an adult human. In certain embodiments, the subject is an elderly human. In certain embodiments, the subject is more than 65 years of age. In some embodiments, the subject is immune-compromised (e.g., due to primary or acquired immunodeficiency). In some embodiments, the human subject receives one or two doses of the vaccine described herein after 65-years of age. In certain embodiments, the subject is a non-human animal. In certain embodiments, the cell is in vitro. In certain embodiments, the cell is in vivo.

In still another aspect, described herein are kits including a container with a compound or pharmaceutical composition described herein. A kit described herein may include a single dose or multiple doses of the compound or pharmaceutical composition. The described kits may be useful in enhancing an immune response (e.g., innate and/or adaptive immune response) in a subject, biological sample, tissue, or cell, in treating a disease (e.g., proliferative disease, inflammatory disease, autoimmune disease, infectious disease, or chronic disease) in a subject in need thereof, and/or in preventing a disease (e.g., proliferative disease, inflammatory disease, autoimmune disease, infectious disease, or chronic disease) in a subject in need thereof. In certain embodiments, a kit described herein further includes instructions for using the compound or pharmaceutical composition included in the kit.

In another aspect, the present disclosure provides methods of enhancing an immune response (e.g., innate and/or adaptive immune response) in a subject in need thereof, the methods comprising administering to the subject a therapeutically effective amount of a compound or pharmaceutical composition described herein.

In another aspect, the present disclosure provides methods of enhancing an immune response (e.g., innate and/or adaptive immune response) in a biological sample, tissue, or cell, the methods comprising contacting the biological sample, tissue, or cell with an effective amount of a compound or pharmaceutical composition described herein.

In another aspect, the present disclosure provides methods of treating a disease (e.g., proliferative disease, inflammatory disease, autoimmune disease, infectious disease, or chronic disease) in a subject in need thereof, the methods comprising administering to the subject a therapeutically effective amount of a compound or pharmaceutical composition described herein. In another aspect, the present disclosure provides methods of preventing a disease in a subject in need thereof, the methods comprising administering to the subject a prophylactically effective amount of a compound or pharmaceutical composition described herein.

In yet another aspect, the present disclosure provides compounds and pharmaceutical compositions described herein for use in a method of the disclosure (e.g., enhancing an immune response (e.g., innate and/or adaptive immune response), a method of treating and/or preventing a disease (e.g., a proliferative disease).

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("C$_{1-10}$ alkyl"). In some embodiments, an alkyl group has 1 to 9 carbon atoms ("C$_{1-9}$ alkyl"). In some embodiments, an alkyl group has 1 to 8 carbon atoms ("C$_{1-8}$ alkyl"). In some embodiments, an alkyl group has 1 to 7 carbon atoms ("C$_{1-7}$ alkyl"). In some embodiments, an alkyl group has 1 to 6 carbon atoms ("C$_{1-6}$ alkyl"). In some embodiments, an alkyl group has 1 to 5 carbon atoms ("C$_{1-5}$ alkyl"). In some embodiments, an alkyl group has 1 to 4 carbon atoms ("C$_{1-4}$ alkyl"). In some embodiments, an alkyl group has 1 to 3 carbon atoms ("C$_{1-3}$ alkyl"). In some embodiments, an alkyl group has 1 to 2 carbon atoms ("C$_{1-2}$ alkyl"). In some embodiments, an alkyl group has 1 carbon atom ("C$_1$ alkyl"). In some embodiments, an alkyl group has 2 to 6 carbon atoms ("C$_{2-6}$ alkyl"). Examples of C$_{1-6}$ alkyl groups include methyl (C$_1$), ethyl (C$_2$), propyl (C$_3$) (e.g., n-propyl, isopropyl), butyl (C$_4$) (e.g., n-butyl, tert-butyl, sec-butyl, iso-butyl), pentyl (C$_5$) (e.g., n-pentyl, 3-pentanyl, amyl, neopentyl, 3-methyl-2-butanyl, tertiary amyl), and hexyl (C$_6$) (e.g., n-hexyl). Additional examples of alkyl groups include n-heptyl (C$_7$), n-octyl (C$_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted C$_{1-10}$ alkyl (such as unsubstituted C$_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted C$_{1-10}$ alkyl (such as substituted C$_{1-6}$ alkyl, e.g., —CF$_3$, Bn).

"Alkenyl" refers to a radical of a straight-chain or branched hydrocarbon group having from 2 to 20 carbon atoms, one or more carbon-carbon double bonds, and no triple bonds ("C$_{2-20}$ alkenyl"). In some embodiments, an alkenyl group has 2 to 10 carbon atoms ("C$_{2-10}$ alkenyl"). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted C$_{2-10}$ alkenyl. In certain embodiments, the alkenyl group is substituted C$_{2-10}$ alkenyl. In an alkenyl group, a C=C double bond for which the stereochemistry is not specified (e.g., —CH=CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("C$_{2-20}$ alkynyl"). In some embodiments, an alkynyl group has 2 to 10 carbon atoms ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C$_{2-10}$ alkynyl. In certain embodiments, the alkynyl group is substituted C$_{2-10}$ alkynyl.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$) R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$) R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O) (OR$^{ee}$)$_2$, —P(=O)(R$^{ee}$)$_2$, —OP(=O)(R$^{ee}$)$_2$, —OP(=O) (OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HCO$_3$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, B(C$_6$F$_5$)$_4$$^-$, BPh$_4$$^-$, Al(OC(CF$_3$)$_3$)$_4$$^-$, and carborane anions (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{aa}$, —P(=O)(OR$^{cc}$)$_2$, —P(=O)(R$^{aa}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^c$, —SO$_2$OR$^c$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and Rad are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{aa})_3{}^+X^-$, —$P(OR^{cc})_2$, —$P(OR)_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March Advanced Organic Chemistry 6th ed. (501-502). Exemplary leaving groups include, but are not limited to, halo (e.g., chloro, bromo, iodo) and activated substituted hydroxyl groups (e.g., —$OC(=O)SR^{aa}$, —$OC(=O)R^{aa}$, —$OCO_2R^{aa}$, —$OC(=O)N(R^{bb})_2$, —$OC(=NR^{bb})R^{aa}$, —$OC(=NR^{bb})OR^{aa}$, —$OC(=NR^{bb})N(R^{bb})_2$, —$OS(=O)R^{aa}$, —$OSO_2R^{aa}$, —$OP(R^{cc})_2$, —$OP(R^{cc})_3$, —$OP(=O)_2R^{aa}$, —$OP(=O)(R^{aa})_2$, —$OP(=O)(OR^{cc})_2$, —$OP(=O)_2N(R^{bb})_2$, and —$OP(=O)(NR^{bb})_2$, wherein $R^{aa}$, $R^{bb}$, and $R^{cc}$ are as defined herein).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

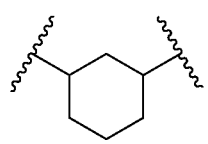 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

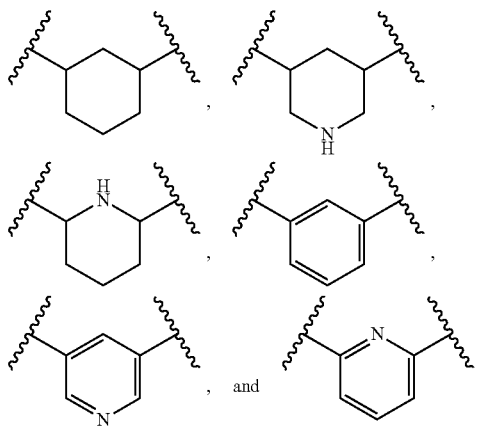

are all examples of a hydrocarbon chain. In contrast, in certain embodiments,

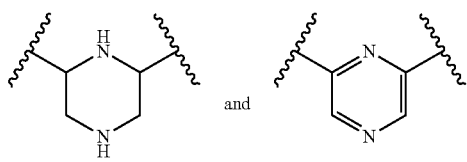 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

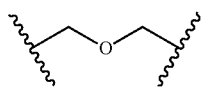 [SMILES: *COC*]

is a $C_3$ hydrocarbon chain wherein one chain atom is replaced with an oxygen atom.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses. When an effective amount of a composition is referred herein, it means the amount is prophylactically and/or therapeutically effective, depending on the subject and/or the disease to be treated. Determining the effective amount or dosage is within the abilities of one skilled in the art.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount effective to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

An "antigen" refers to an entity that is bound by an antibody or receptor, or an entity that induces the production of the antibody. In some embodiments, an antigen increases the production of antibodies that specifically bind the antigen. In some embodiments, an antigen comprises a protein or polypeptide. Such proteins or peptides are referred to herein as "immunogenic polypeptide." In some embodiments, the term "antigen" encompasses nucleic acids (e.g., DNA or RNA molecules) that encode immunogenic polypeptides. In some embodiments, the antigen is from a microbial pathogen. For example, the antigen may comprise parts (coats, capsules, cell walls, flagella, fimbriae, and toxins) of bacteria, viruses, fungi, and other microorganisms. In some embodiments, the antigen is a cancer-specific antigen.

Being "immunogenic" means that the composition elicits immune response when administered to a subject (e.g., a mammalian subject such as a human). As used herein, an "immune response" refers to a response by a cell of the immune system, such as a B cell, T cell (CD4 or CD8), regulatory T cell, antigen-presenting cell, dendritic cell, monocyte, macrophage, NKT cell, NK cell, basophil, eosinophil, or neutrophil, to a stimulus (e.g., to an antigen or an adjuvant). As used herein, an "immune response" refers to a response by a cell of the immune system, such as an antigen-presenting cell, dendritic cell, monocyte, macrophage, NKT cell, NK cell, or other innate lymphoid cells, basophil, eosinophil, or neutrophil, B cell, T cell (CD4 or CD8), regulatory T cell, to a stimulus (e.g., to an antigen or an adjuvant).

An "antigen-specific response" or "adaptive immune response" refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response.

In some embodiments, an antigen-specific immune response includes both a humoral and/or a cell-mediated immune response to the antigen. A "humoral immune response" is an antibody-mediated immune response and involves the induction and generation of antibodies that recognize and bind with some affinity for the antigen in the immunogenic composition of the invention, while a "cell-mediated immune response" is one mediated by T-cells and/or other white blood cells. A "cell-mediated immune response" is elicited by the presentation of antigenic epitopes in association with Class I or Class II molecules of the major histocompatibility complex (MHC), CD1 or other non-classical MHC-like molecules. This activates antigen-specific CD4+T helper cells or CD8+ cytotoxic lymphocyte cells ("CTLs"). CTLs have specificity for peptide antigens that are presented in association with proteins encoded by classical or non-classical MHCs and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide or other antigens in association with classical or non-classical MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to re-stimulation with antigen. Such assays are well known in the art. See, e.g., Erickson et al. (1993) J. Immunol. 151:4189-4199; and Doe et al. (1994) Eur. J. Immunol. 24:2369-2376.

In some embodiments, the immune response elicited by the composition described herein is an innate immune response. An "innate immune response" refers to the response by the innate immune system. The innate immune system uses a set of germline-encoded receptors ("pattern recognition receptor" or "PRR") for the recognition of conserved molecular patterns present in microorganisms. These molecular patterns occur in certain constituents of microorganisms including: lipopolysaccharides, peptidoglycans, lipoteichoic acids, phosphatidyl cholines, bacteria-specific proteins, including lipoproteins, bacterial DNAs, viral single and double-stranded RNAs, unmethylated CpG-DNAs, mannans and a variety of other bacterial and fungal cell wall components. Such molecular patterns can also occur in other molecules such as plant alkaloids. These targets of innate immune recognition are called Pathogen Associated Molecular Patterns (PAMPs) since they are produced by microorganisms and not by the infected host organism. In some embodiments, the innate immune response elicited by the composition described herein confers heterologous ("nonspecific") immunity to a broad range of pathogenic microbes by enhancing innate immune responses to subsequent stimuli, a phenomenon known as "trained immunity", a form of innate memory, e.g., as described in Netea et al. (Trained Immunity: An Ancient Way of Remembering. Cell Host Microbe. 2017 Mar. 8; 21(3):297-300, incorporated herein by reference).

An "adjuvant" refers to a pharmacological or immunological agent that modifies the effect of other agents, for example, of an antigen in a vaccine. Adjuvants are typically included in vaccines to enhance the recipient subject's immune response to an antigen. The use of adjuvants allows the induction of a greater immune response in a subject with the same dose of antigen, or the induction of a similar level of immune response with a lower dose of injected antigen. Adjuvants that are known to those of skill in the art, include, without limitation: aluminum salts, liposomes, lipopolysaccharide (LPS), molecular cages for antigen, components of bacterial cell walls, endocytosed nucleic acids such as double-stranded RNA (dsRNA), single-stranded DNA (ssDNA), and unmethylated CpG dinucleotide-containing DNA. Adjuvants are thought to function in several ways, for example, but not limited to, increasing the surface area of antigen, prolonging the retention of the antigen in the body thus allowing time for the lymphoid system to have access to the antigen, slowing the release of antigen, targeting antigen to macrophages, activating macrophages, activating leukocytes such as antigen-presenting cells (e.g., monocytes, macrophages, and/or dendritic cells), or otherwise eliciting broad activation of the cells of the immune system see, e.g., H. S. Warren et al, Annu. Rev. Immunol., 4:369 (1986), incorporated herein by reference. Heterologous immunity refers to the phenomenon whereby a history of an immune response against a stimulus or pathogen can provide a level of immunity to a second unrelated stimulus or pathogen (e.g., as described in Chen et al., Virology 2015 482: 89-97, incorporated herein by reference). For example, an antigen that induces cross-reactive memory CD8+ T cells against multiple unrelated viruses such as influenza A and Epstein-Barr Virus (EBV), as described in Watkin et al., J Allerg Clin Immunol 2017 October; 140(4) 1206-1210, incorporated herein by reference. In some embodiments, the compounds described herein induce and/or enhance the heterologous protection.

The ability of an adjuvant to induce and increase a specific type of immune response and the identification of that ability is thus a key factor in the selection of particular adjuvants for vaccine use against a particular pathogen. Adjuvants that are known to those of skill in the art, include, without limitation: aluminum salts (referred to herein as "alum"), liposomes, lipopolysaccharide (LPS) or its derivatives such as monophosphoryl lipid A (MPLA), molecular cages for antigen, components of bacterial cell walls, endocytosed nucleic acids such as double-stranded RNA (dsRNA), single stranded RNA (ssRNA), single-stranded DNA (ssDNA), and unmethylated CpG dinucleotide-containing DNA. Typical adjuvants include water and oil emulsions, e.g., Freund's adjuvant and MF59, and chemical compounds such as aluminum hydroxide or alum. At present, currently licensed vaccines in the United states contain only a limited number of adjuvants, such as alum that enhances production of TH 2 cells and MPLA which activates innate immunity via Toll-like receptor 4 (TLR4). Many of the most effective adjuvants include bacteria or their products, e.g., microorganisms such as the attenuated strain of *Mycobacterium bovis*, Bacillus Calmette-Guérin (BCG); microorganism components, e.g., alum-precipitated diphtheria toxoid, bacterial lipopolysaccharide and endotoxins or their derivatives such as MPLA.

As used herein, the term "infectious disease" refers to an illness caused by a pathogenic biological agent that results from transmission from an infected person, animal, or reservoir to a susceptible host, either directly or indirectly, through an intermediate plant or animal host, vector, or inanimate environment. See Last J M. ed. A dictionary of epidemiology. 4th ed., New York: Oxford University Press, 1988. Infectious disease is also known as transmissible disease or communicable disease. In certain embodiments, infectious diseases may be asymptomatic for much or even all of their course in a given host. Infectious pathogens include some viruses, bacteria, fungi, protozoa, multicellular parasites, and aberrant proteins known as prions.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva). In some embodiments, the cancer treated using the composition and methods of the present disclosure is melanoma.

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosus, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

A "chronic disease" refers to a disease lasting for three or more months. Exemplary chronic diseases include, but are not limited to, arthritis, cardiovascular disease such as heart disease, stroke, cancer (e.g., breast cancer or colon cancer), chronic respiratory diseases, diabetes, epilepsy, seizures, obesity, and oral health problems.

A "vaccine" or "vaccine composition" refers to a composition that activates or enhances a subject's immune response to an antigen after the vaccine is administered to the subject.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

(FIGS. 1A-1C) Individual scatter plots from 3 unique adult PBMC samples/donors, run in duplicate (x and y axes). (FIG. 1D) Venn diagram comparing hits between 3 unique adult donors, with 24 hits identified that passed analysis threshold for at least 2 donors and ~10 hits common to all with a rZ>3 for each donor.

(FIG. 2A) Human adult (top) and elderly (bottom) PBMCs stimulated for 18 hours with the TLR7/8 agonist R848 and 24 confirmed hit compounds from TNF AlphaLISA screen. TNF (left panels) and IL-1β (right panels) were assessed in cell-free supernatants by ELISA. Data are shown as median and interquartile range of N=5. (FIG. 2B) Compound 037 and 038, both small molecules within the same class, were identified as the most potent inducers of innate immune cytokines.

(FIG. 3A) TNF production measured by ELISA after stimulation of human adult peripheral blood mononuclear cells (PBMCs) with R848 or compound 037 at seven different concentrations (0.05 µM-33 µM) for 18 hours (N=8-12). (FIG. 3B) TNF production measured by ELISA after stimulation of PBMCs with compound 037 and R848 at a concentration of 10 μM. Compound R848 is a small molecule imidazoquinoline that activates human leukocytes via PRRs (TLR7/8 and inflammasome).

(FIG. 5A) Human adult PBMCs were stimulated for 18 hours with compound 037 or R848 at 33 μM. Production of human TNF was assessed in cell-free supernatants by ELISA (N=5). (FIG. 5B) in comparison to the positive control compound R848, 037 does not substantially activate THP1 cells, as measured by NF-κB-driven expression of luciferase (N=4). Results are shown as the median, the 25th and 75th percentiles (boxes) and the 5th and 95th percentiles (whiskers) **$p<0.01$ determined by repeated measure one-way ANOVA with Dunnett's multiple comparison test on log-transformed data and comparing each compound with DMSO (control condition).

DETAILED DESCRIPTION OF CERTAIN EMBODIMENTS

Figure 1A:
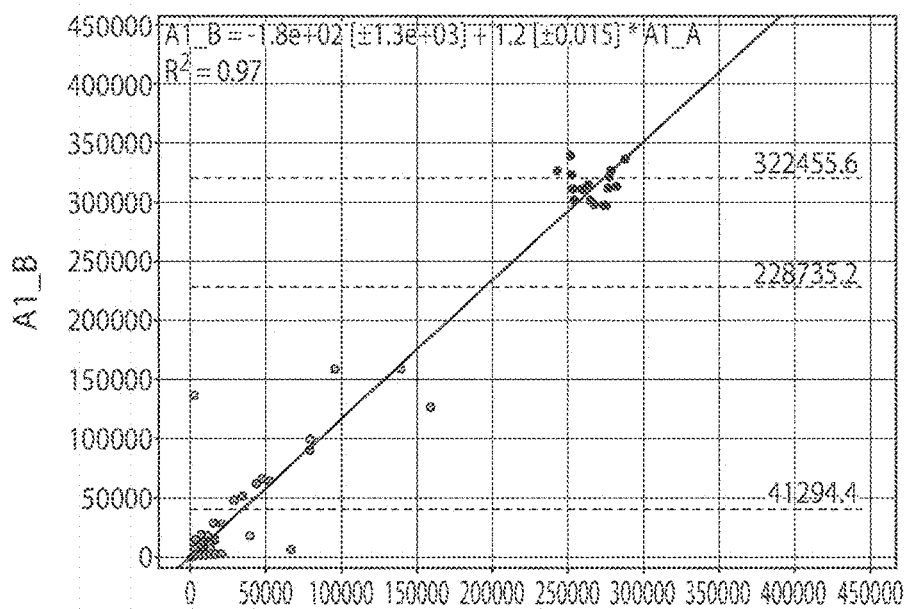
FIGS. 1A-1D are scatter plots showing the stimulation of adult peripheral blood mononuclear cells (PBMCs) with hit compounds from a TNF AlphaLISA screen. The PBMCs were stimulated for 18 hours.

Described herein are compounds of Formula (I), and pharmaceutically acceptable salts, solvates, hydrates, polymorphs, co-crystals, tautomers, stereoisomers, isotopically labeled derivatives, and prodrugs thereof. The compounds described herein are enhancers and/or modifiers of an immune response (e.g., innate and/or adaptive immune response), and/or adjuvants in a vaccine for a disease, e.g., proliferative disease, inflammatory disease, autoimmune disease, infectious disease, or chronic disease, or as stand alone anti-infective or immune response modifying agents. The compounds may be useful in treating or preventing a disease (e.g., proliferative disease, inflammatory disease, autoimmune disease, infectious disease, or chronic disease) in a subject in need thereof. Also provided are pharmaceutical compositions, kits, and uses including a compound described herein.

Compounds

One aspect of the present disclosure relates to the compounds described herein. The compounds described herein are enhancers and/or modifiers of an immune response (e.g., innate and/or adaptive immune response), and/or adjuvants in a vaccine for a disease, e.g., proliferative disease, inflammatory disease, autoimmune disease, infectious disease, or chronic disease, or as stand alone anti-infective or immune response modifying agents. In certain embodiments, a compound described herein is an immunomodulator. In certain embodiments, a compound described herein is a compound of Formula (I), or a pharmaceutically acceptable salt, solvate, hydrate, polymorph, co-crystal, tautomer, stereoisomer, isotopically labeled derivative, or prodrug thereof.

In one aspect, the present disclosure provides compounds of Formula (I):

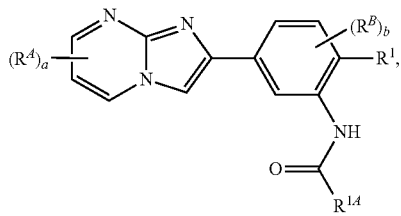

and pharmaceutically acceptable salts, solvates, hydrates, polymorphs, co-crystals, tautomers, stereoisomers, isotopically labeled derivatives, and prodrugs thereof, wherein:

$R^{1A}$ is substituted or unsubstituted phenyl or substituted or unsubstituted benzyl, or substituted or unsubstituted 6-membered heteroaryl;

$R^1$ is hydrogen, halogen, substituted or unsubstituted $C_{1-6}$ alkyl, —$OR^a$, or —$N(R^{a1})_2$;

each instance of $R^A$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^{a1})_2$, —$SR^a$, —CN, —C(=O)$R^a$, —C(=O)$OR^a$, —C(=O)$N(R^{a1})_2$, or —$NO_2$;

each instance of $R^B$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^{a1})_2$, —$SR^a$, —CN, —C(=O)$R^a$, —C(=O)$OR^a$, —C(=O)$N(R^{a1})_2$, or —$NO_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom;

each instance of $R^{a1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or two instances of Rai are joined to form a substituted or unsubstituted, heterocyclic ring, or substituted or unsubstituted, heteroaryl ring;

a is 0, 1, 2, or 3; and b is 0, 1, 2, or 3;

wherein the compound is not of the formula:

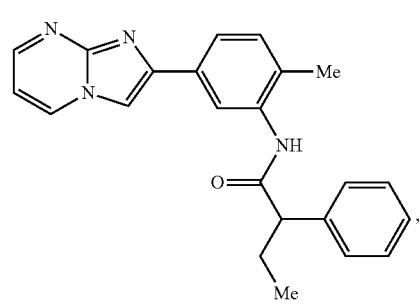

(037)

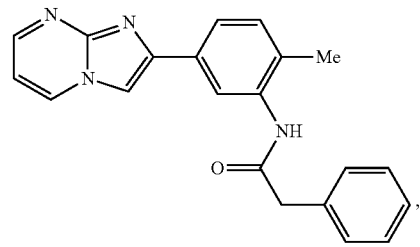

(FRF-02-103)

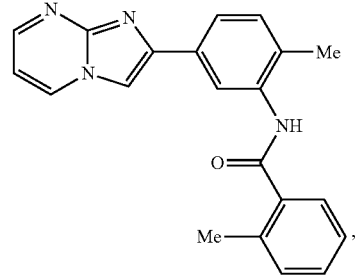

(37.17)

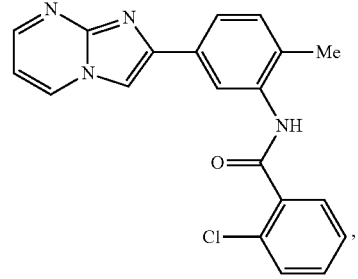

(37.33)

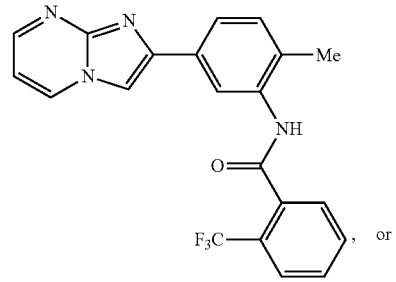

(37.37)

, or

-continued (37.16)

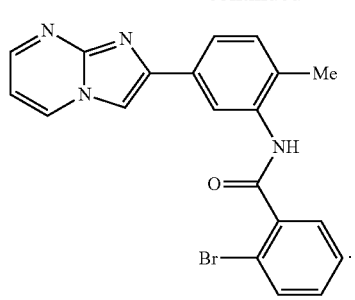

Formula (I) includes substituent R¹ on the phenyl ring. In certain embodiments, R¹ is hydrogen. In certain embodiments, R$^{A1}$ is halogen (e.g., F, Cl, Br, or I). In certain embodiments, R¹ is substituted or unsubstituted C$_{1-6}$ alkyl (e.g., substituted or unsubstituted Me or substituted or unsubstituted Et). In certain embodiments, R¹ is Me. In certain embodiments, R¹ is Et. In certain embodiments, R¹ is —OR$^a$ (e.g., —OH, —O (substituted or unsubstituted C$_{1-6}$ alkyl) (e.g., —OMe, —OEt, —OPr, —OBu, or —OBn). In certain embodiments, R¹ is —N(R$^{a1}$)$_2$ (e.g., —NH$_2$, —NH (substituted or unsubstituted C$_{1-6}$ alkyl) (e.g., —NHMe), or —N (substituted or unsubstituted C$_{1-6}$ alkyl)-(substituted or unsubstituted C$_{1-6}$ alkyl) (e.g., —NMe$_2$)).

Formula (I) includes substituent R$^{14}$. In certain embodiments, R$^{14}$ is substituted or unsubstituted phenyl. In certain embodiments, R$^{14}$ is of the formula:

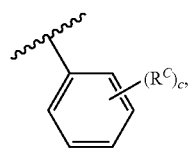

wherein each instance of R$^C$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^{a1}$)$_2$, —SR$^a$, —CN, —C(=O)R$^a$, —C(=O)OR$^a$, —C(=O)N(R$^{a1}$)$_2$, or —NO$_2$; and c is 0, 1, 2, 3, 4, or 5. In certain embodiments, at least one instance of R$^C$ is halogen. In certain embodiments, at least one instance of R$^C$ is F. In certain embodiments, at least one instance of R$^C$ is Br. In certain embodiments, at least one instance of R$^C$ is Cl. In certain embodiments, at least one instance of R$^C$ is I. In certain embodiments, at least one instance of R$^C$ is substituted or unsubstituted alkyl (e.g., C$_{1-6}$ alkyl). In certain embodiments, at least one instance of R$^C$ is substituted or unsubstituted Me. In certain embodiments, at least one instance of R$^C$ is Me. In certain embodiments, at least one instance of R$^C$ is substituted methyl (e.g., —CF$_3$ or Bn). In certain embodiments, at least one instance of R$^C$ is —CF$_3$. In certain embodiments, at least one instance of R$^A$ is substituted or unsubstituted alkenyl (e.g., substituted or unsubstituted C$_{2-6}$ alkenyl). In certain embodiments, at least one instance of R$^C$ is substituted or unsubstituted alkynyl (e.g., substituted or unsubstituted C$_{2-6}$ alkynyl). In certain embodiments, at least one instance of R$^A$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of R$^C$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of R$^C$ is substituted or unsubstituted aryl (e.g., substituted or unsubstituted, 6- to 10-membered aryl). In certain embodiments, at least one instance of R$^C$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of R$^C$ is —OR$^a$ (e.g., —OH or —O (substituted or unsubstituted C$_{1-6}$ alkyl) (e.g., —OMe)). In certain embodiments, at least one instance of R$^C$ is —OMe. In certain embodiments, at least one instance of R$^C$ is —N(R$^{a1}$)$_2$ (e.g., —NH$_2$, —NH (substituted or unsubstituted C$_{1-6}$ alkyl) (e.g., —NHMe), or —NMe$_2$). In certain embodiments, at least one instance of R$^C$ is —SR$^a$ (e.g., —SH, —S (substituted or unsubstituted C$_{1-6}$ alkyl) (e.g., —SMe, —SEt, —SPr, —SBu, or —SBn), or —S (substituted or unsubstituted phenyl) (e.g., —SPh)). In certain embodiments, at least one instance of R$^C$ is —CN. In certain embodiments, at least one instance of R$^A$ is —C(=O)R$^a$ (e.g., —C(=O)(substituted or unsubstituted alkyl) or —C(=O)(substituted or unsubstituted phenyl)). In certain embodiments, at least one instance of R$^C$ is —C(=O)OR$^a$ (e.g., —C(=O)OH, —C(=O)O (substituted or unsubstituted alkyl) (e.g., —C(=O)OMe), or —C(=O)O (substituted or unsubstituted phenyl)).

In certain embodiments, at least one instance of R$^A$ is —C(=O)N(R$^{a1}$)$_2$ (e.g., —C(=O)NH$_2$, —C(=O)NH (substituted or unsubstituted alkyl), —C(=O)NH (substituted or unsubstituted phenyl), —C(=O)N (substituted or unsubstituted alkyl)-(substituted or unsubstituted alkyl), or —C(=O)N (substituted or unsubstituted phenyl)-(substituted or unsubstituted alkyl)). In certain embodiments, at least one instance of R$^C$ is —NO$_2$.

In certain embodiments, R$^{14}$ is of the formula:

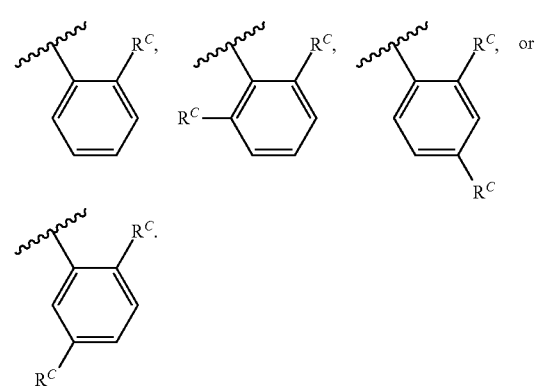

In certain embodiments, R$^{14}$ is of the formula:

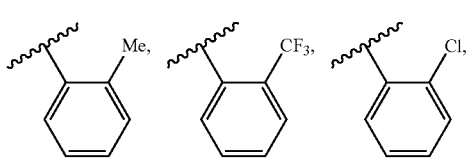

-continued

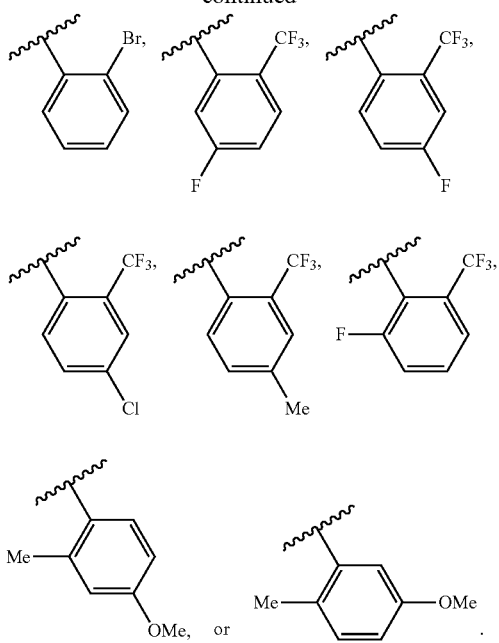

In certain embodiments, $R^{14}$ is substituted or unsubstituted benzyl. In certain embodiments, $R^{14}$ is of the formula:

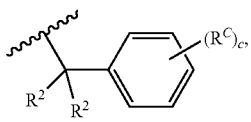

wherein each instance of $R^2$ is independently hydrogen, halogen, substituted or unsubstituted $C_{1-6}$ alkyl, —$OR^a$, or —$N(R^{a1})_2$; each instance of $R^C$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^{a1})_2$, —$SR^a$, —CN, —C(=O)$R^a$, —C(=O)$OR^a$, —C(=O)N($R^{a1}$)$_2$, or —$NO_2$; and c is 0, 1, 2, 3, 4, or 5. In certain embodiments, $R^{14}$ is of the formula:

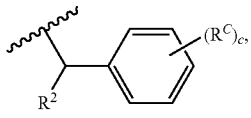

wherein $R^2$ is hydrogen, halogen, substituted or unsubstituted $C_{1-6}$ alkyl, —$OR^a$, or —$N(R^{a1})_2$; each instance of $R^C$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^{a1})_2$, —$SR^a$, —CN, —C(=O)$R^a$, —C(=O)$OR^a$, —C(=O)N($R^{a1}$)$_2$, or —$NO_2$; and c is 0, 1, 2, 3, 4, or 5. In certain embodiments, $R^{14}$ is of the formula:

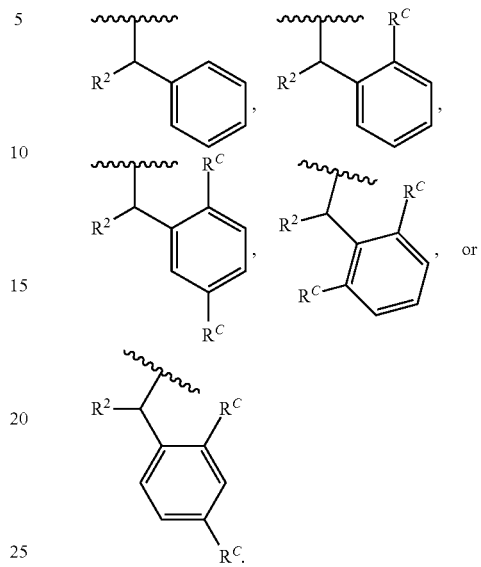

In certain embodiments, at least one instance of $R^2$ is hydrogen. In certain embodiments, at least one instance of $R^2$ is halogen (e.g., F, Cl, Br, or I). In certain embodiments, at least one instance of $R^2$ is substituted or unsubstituted $C_{1-6}$ alkyl (e.g., substituted or unsubstituted Me or substituted or unsubstituted Et). In certain embodiments, at least one instance of $R^2$ is Me. In certain embodiments, at least one instance of $R^2$ is substituted or unsubstituted Me. In certain embodiments, $R^2$ is —$CH_2OH$. In certain embodiments, at least one instance of $R^2$ is Et. In certain embodiments, at least one instance of $R^2$ is —$OR^a$ (e.g., —OH, —O (substituted or unsubstituted $C_{1-6}$ alkyl) (e.g., —OMe, —OEt, —OPr, —OBu, or —OBn). In certain embodiments, at least one instance of $R^2$ is —$N(R^{a1})_2$ (e.g., —$NH_2$, —NH (substituted or unsubstituted $C_{1-6}$ alkyl) (e.g., —NHMe), or —N (substituted or unsubstituted $C_{1-6}$ alkyl)-(substituted or unsubstituted $C_{1-6}$ alkyl) (e.g., —$NMe_2$)). In certain embodiments, $R^{14}$ is of the formula:

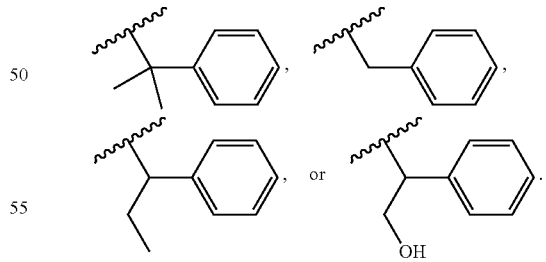

In certain embodiments, $R^{14}$ is substituted or unsubstituted 6-membered heteroaryl.

In certain embodiments, $R^{14}$ is substituted or unsubstituted pyridine, substituted or unsubstituted pyrimidine, or substituted or unsubstituted pyrazine.

Formula (I) may include one or more instances of $R^4$ on the imidazopyrimidine ring. When Formula (I) includes two or more instances of $R^4$, any two instances of $R^4$ may be the same or different from each other. In certain embodiments, a is 0. In certain embodiments, a is 1. In certain embodiments, a is 2. In certain embodiments, a is 3. In certain embodiments, at least one instance of $R^A$ is halogen. In certain embodiments, at least one instance of $R^A$ is F. In certain embodiments, at least one instance of $R^A$ is Br, Cl, or I. In certain embodiments, at least one instance of $R^A$ is substituted or unsubstituted alkyl (e.g., substituted or unsubstituted $C_{1-6}$ alkyl). In certain embodiments, at least one instance of $R^A$ is Me. In certain embodiments, at least one instance of $R^A$ is substituted methyl (e.g., —$CF_3$ or Bn). In certain embodiments, at least one instance of $R^A$ is Et. In certain embodiments, at least one instance of $R^{A1}$ is substituted ethyl. In certain embodiments, at least one instance of $R^A$ is n-Pr. In certain embodiments, at least one instance of $R^A$ is i-Pr. In certain embodiments, at least one instance of $R^A$ is substituted propyl (e.g., perfluoropropyl). In certain embodiments, at least one instance of $R^A$ is Me, Et, or n-Pr. In certain embodiments, at least one instance of $R^A$ is substituted or unsubstituted alkenyl (e.g., substituted or unsubstituted $C_{2-6}$ alkenyl). In certain embodiments, at least one instance of $R^A$ is substituted or unsubstituted alkynyl (e.g., substituted or unsubstituted $C_{2-6}$ alkynyl). In certain embodiments, at least one instance of $R^A$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^A$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^A$ is substituted or unsubstituted aryl (e.g., substituted or unsubstituted, 6- to 10-membered aryl). In certain embodiments, at least one instance of $R^A$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^A$ is —$OR^a$ (e.g., —OH or —O (substituted or unsubstituted $C_{1-6}$ alkyl) (e.g., —OMe)). In certain embodiments, at least one instance of $R^A$ is —OMe. In certain embodiments, at least one instance of $R^A$ is —$N(R^{a1})_2$ (e.g., —$NH_2$, —NH (substituted or unsubstituted $C_{1-6}$ alkyl) (e.g., —NHMe), or —$NMe_2$). In certain embodiments, at least one instance of $R^A$ is —$SR^a$ (e.g., —SH, —S (substituted or unsubstituted $C_{1-6}$ alkyl) (e.g., —SMe, —SEt, —SPr, —SBu, or —SBn), or —S (substituted or unsubstituted phenyl) (e.g., —SPh)). In certain embodiments, at least one instance of $R^A$ is —CN. In certain embodiments, at least one instance of $R^A$ is —C(=O)$R^a$ (e.g., —C(=O)(substituted or unsubstituted alkyl) or —C(=O)(substituted or unsubstituted phenyl)). In certain embodiments, at least one instance of $R^A$ is —C(=O)$OR^a$ (e.g., —C(=O)OH, —C(=O)O (substituted or unsubstituted alkyl) (e.g., —C(=O)OMe), or —C(=O)O (substituted or unsubstituted phenyl)). In certain embodiments, at least one instance of $R^A$ is —C(=O)N$(R^{a1})_2$ (e.g., —C(=O)$NH_2$, —C(=O)NH (substituted or unsubstituted alkyl), —C(=O)NH (substituted or unsubstituted phenyl), —C(=O)N (substituted or unsubstituted alkyl)-(substituted or unsubstituted alkyl), or —C(=O)N (substituted or unsubstituted phenyl)-(substituted or unsubstituted alkyl)). In certain embodiments, at least one instance of $R^A$ is —$NO_2$.

Formula (I) may include one or more instances of $R^B$ on the phenyl ring. When Formula (I) includes two or more instances of $R^B$, any two instances of $R^B$ may be the same or different from each other. In certain embodiments, b is 0. In certain embodiments, b is 1. In certain embodiments, b is 2. In certain embodiments, b is 3. In certain embodiments, at least one instance of $R^B$ is halogen. In certain embodiments, at least one instance of $R^B$ is F. In certain embodiments, at least one instance of $R^B$ is Br, Cl, or I. In certain embodiments, at least one instance of $R^B$ is substituted or unsubstituted alkyl (e.g., substituted or unsubstituted $C_{1-6}$ alkyl). In certain embodiments, at least one instance of $R^B$ is Me. In certain embodiments, at least one instance of $R^B$ is substituted methyl (e.g., —$CF_3$ or Bn). In certain embodiments, at least one instance of $R^B$ is Et. In certain embodiments, at least one instance of $R^B$ is substituted ethyl. In certain embodiments, at least one instance of $R^B$ is n-Pr. In certain embodiments, at least one instance of $R^B$ is i-Pr. In certain embodiments, at least one instance of $R^B$ is substituted propyl (e.g., perfluoropropyl). In certain embodiments, at least one instance of $R^B$ is Me, Et, or n-Pr. In certain embodiments, at least one instance of $R^B$ is substituted or unsubstituted alkenyl (e.g., substituted or unsubstituted $C_{2-6}$ alkenyl). In certain embodiments, at least one instance of $R^B$ is substituted or unsubstituted alkynyl (e.g., substituted or unsubstituted $C_{2-6}$ alkynyl). In certain embodiments, at least one instance of $R^B$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^B$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^B$ is substituted or unsubstituted aryl (e.g., substituted or unsubstituted, 6- to 10-membered aryl). In certain embodiments, at least one instance of $R^B$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^B$ is —$OR^a$ (e.g., —OH or —O (substituted or unsubstituted $C_{1-6}$ alkyl) (e.g., —OMe)). In certain embodiments, at least one instance of $R^B$ is —OMe. In certain embodiments, at least one instance of $R^B$ is —$N(R^{a1})_2$ (e.g., —$NH_2$, —NH (substituted or unsubstituted $C_{1-6}$ alkyl) (e.g., —NHMe), or —$NMe_2$). In certain embodiments, at least one instance of $R^B$ is —$SR^a$ (e.g., —SH, —S (substituted or unsubstituted $C_{1-6}$ alkyl) (e.g., —SMe, —SEt, —SPr, —SBu, or —SBn), or —S (substituted or unsubstituted phenyl) (e.g., —SPh)). In certain embodiments, at least one instance of $R^B$ is —CN. In certain embodiments, at least one instance of $R^B$ is —C(=O)$R^a$ (e.g., —C(=O)(substituted or unsubstituted alkyl) or —C(=O)(substituted or unsubstituted phenyl)). In certain embodiments, at least one instance of $R^B$ is —C(=O)$OR^a$ (e.g., —C(=O)OH, —C(=O)O (substituted or unsubstituted alkyl) (e.g., —C(=O)OMe), or —C(=O)O (substituted or unsubstituted phenyl)). In certain embodiments, at least one instance of $R^B$ is —C(=O)N$(R^{a1})_2$ (e.g., —C(=O)$NH_2$, —C(=O)NH (substituted or unsubstituted alkyl), —C(=O)NH (substituted or unsubstituted phenyl), —C(=O)N (substituted or unsubstituted alkyl)-(substituted or unsubstituted alkyl), or —C(=O)N (substituted or unsubstituted phenyl)-(substituted or unsubstituted alkyl)). In certain embodiments, at least one instance of $R^B$ is —NO$_2$.

Formula (I) may include one or more instances of $R^a$. In certain embodiments, at least one instance of $R^a$ is hydrogen. In certain embodiments, at least one instance of $R^a$ is substituted or unsubstituted acyl (e.g., —C(=O)Me). In certain embodiments, at least one instance of $R^a$ is substituted or unsubstituted alkyl (e.g., C$_{1-6}$ alkyl). In certain embodiments, at least one instance of $R^a$ is substituted or unsubstituted alkenyl (e.g., substituted or unsubstituted C$_{2-6}$ alkenyl). In certain embodiments, at least one instance of $R^a$ is substituted or unsubstituted alkynyl (e.g., substituted or unsubstituted C$_{2-6}$ alkynyl). In certain embodiments, at least one instance of $R^a$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^a$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^a$ is substituted or unsubstituted aryl (e.g., substituted or unsubstituted, 6- to 10-membered aryl). In certain embodiments, at least one instance of $R^a$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^a$ is a nitrogen protecting group when attached to a nitrogen atom (e.g., Bn, Boc, Cbz, Fmoc, trifluoroacetyl, triphenylmethyl, acetyl, or Ts). In certain embodiments, at least one instance of $R^a$ is an oxygen protecting group when attached to an oxygen atom (e.g., silyl, TBDPS, TBDMS, TIPS, TES, TMS, MOM, THP, t-Bu, Bn, allyl, acetyl, pivaloyl, or benzoyl). In certain embodiments, at least one instance of $R^a$ is a sulfur protecting group when attached to a sulfur atom.

Formula (I) may include one or more instances of Rai. In certain embodiments, at least one instance of Rai is hydrogen. In certain embodiments, at least one instance of Rai is substituted or unsubstituted acyl (e.g., —C(=O)Me). In certain embodiments, at least one instance of Rai is substituted or unsubstituted alkyl (e.g., C$_{1-6}$ alkyl). In certain embodiments, at least one instance of Rai is substituted or unsubstituted alkenyl (e.g., substituted or unsubstituted C$_{2-6}$ alkenyl). In certain embodiments, at least one instance of Rai is substituted or unsubstituted alkynyl (e.g., substituted or unsubstituted C$_{2-6}$ alkynyl). In certain embodiments, at least one instance of Rai is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of Rai is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of Rai is substituted or unsubstituted aryl (e.g., substituted or unsubstituted, 6- to 10-membered aryl). In certain embodiments, at least one instance of $R^{a1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of Rai is a nitrogen protecting group when attached to a nitrogen atom (e.g., Bn, Boc, Cbz, Fmoc, trifluoroacetyl, triphenylmethyl, acetyl, or Ts). In certain embodiments, two instances of Rai are joined to form a substituted or unsubstituted, heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, two instances of Rai are joined to form a substituted or unsubstituted, heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, the compound of Formula (I) is of the formula:

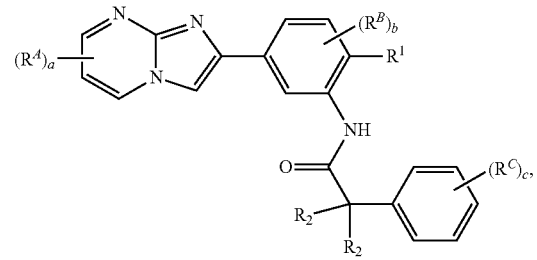

or a pharmaceutically acceptable salt, solvate, hydrate, polymorph, co-crystal, tautomer, stereoisomer, isotopically labeled derivative, or prodrug thereof, wherein:

each instance of $R^2$ is independently hydrogen, halogen, substituted or unsubstituted C$_{1-6}$ alkyl, —OR$^a$, or —N(R$^{a1}$)$_2$;

each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^{a1}$)$_2$, —SR$^a$, —CN, —C(=O)R$^a$, —C(=O)OR$^a$, —C(=O)N(R$^{a1}$)$_2$, or —NO$_2$; and c is 0, 1, 2, 3, 4, or 5.

In certain embodiments, the compound of Formula (I) is of the formula:

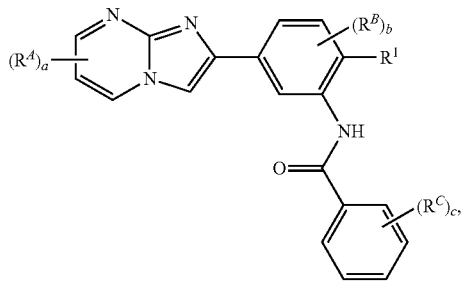

or a pharmaceutically acceptable salt, solvate, hydrate, polymorph, co-crystal, tautomer, stereoisomer, isotopically labeled derivative, or prodrug thereof, wherein:

each instance of $R^C$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^{a1})_2$, —$SR^{aa}$, —CN, —C(=O)$R^a$, —C(=O)$OR^a$, —C(=O)N(Rai)$_2$, or —$NO_2$; and c is 0, 1, 2, 3, 4, or 5.

In certain embodiments, the compound of Formula (I) is of the formula:

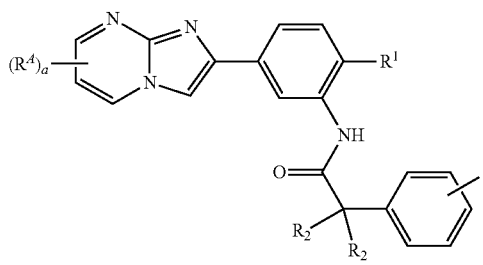

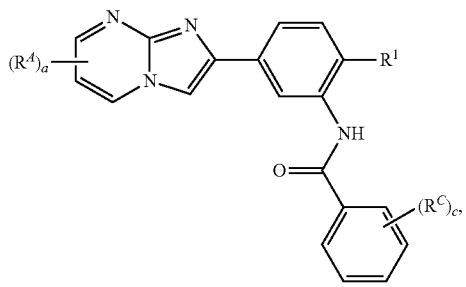

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

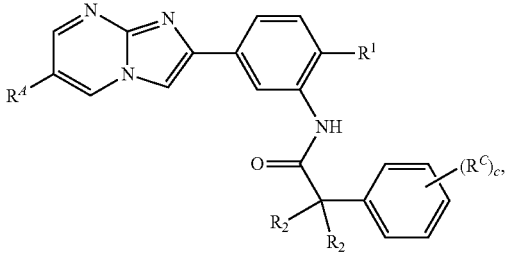

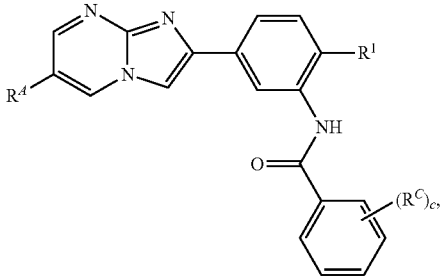

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

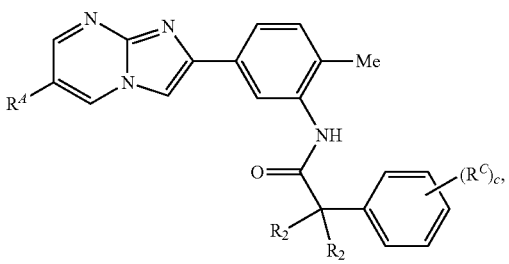

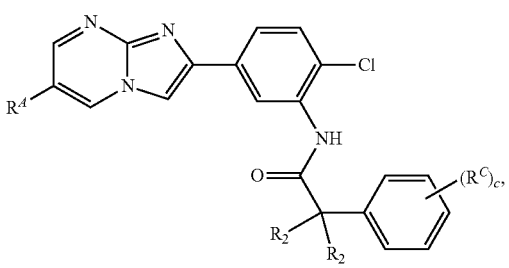

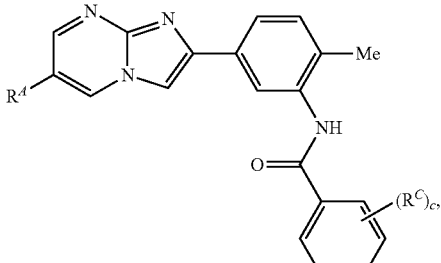

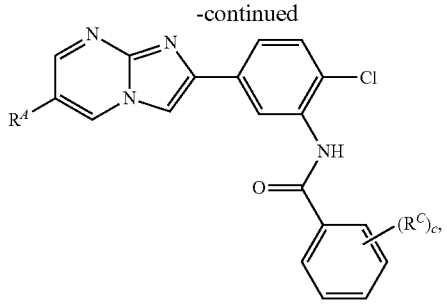

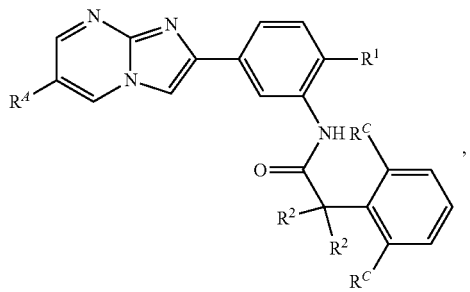

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

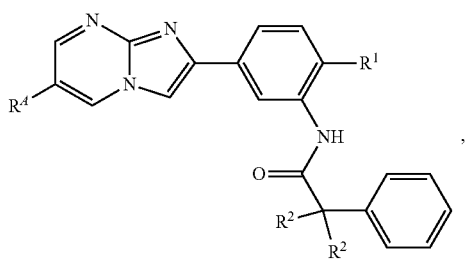

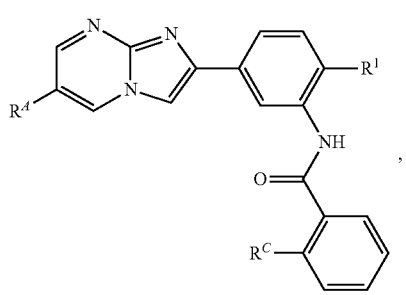

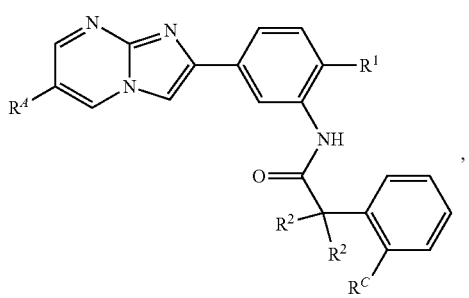

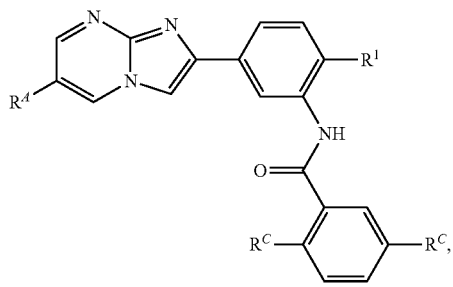

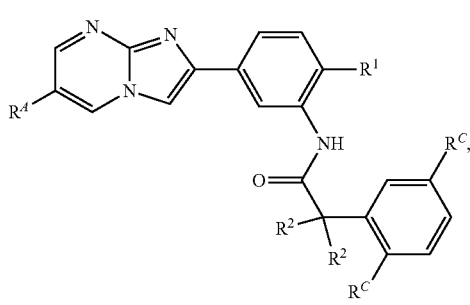

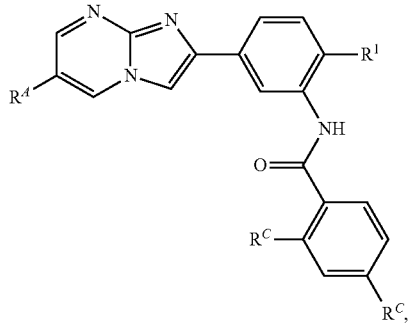

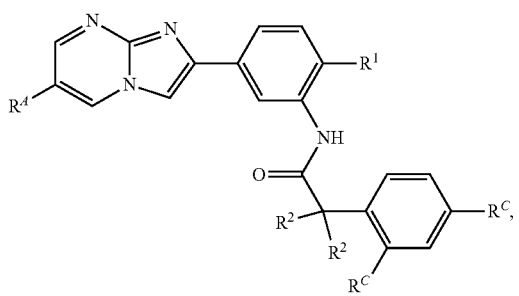

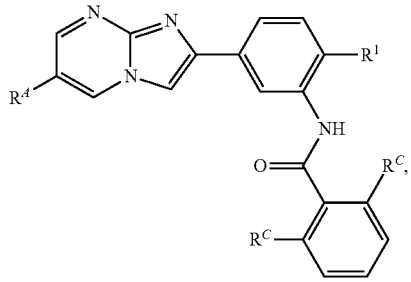

or a pharmaceutically acceptable salt, solvate, hydrate, polymorph, co-crystal, tautomer, stereoisomer, isotopically labeled derivative, or prodrug thereof.

In certain embodiments, the compound of Formula (I) is not of the formula:
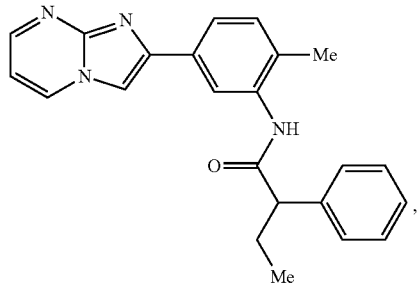
(037)
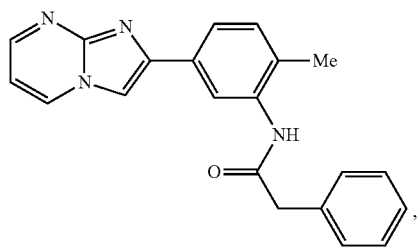
(FRF-02-103)
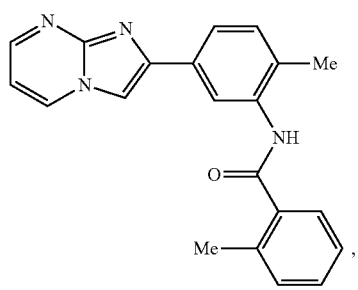
(31.17)
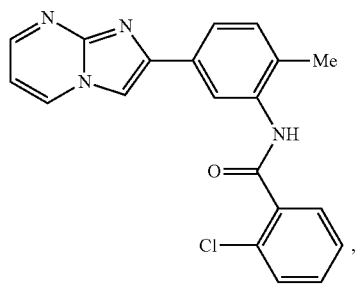
(37.33)
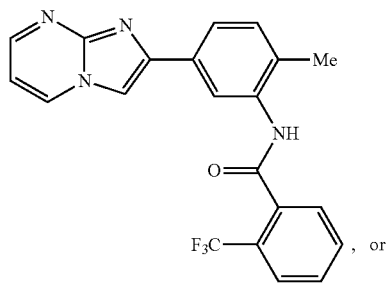
(37.37), or
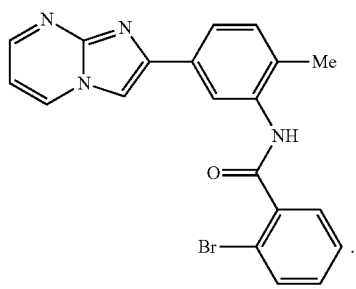
(37.16)
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
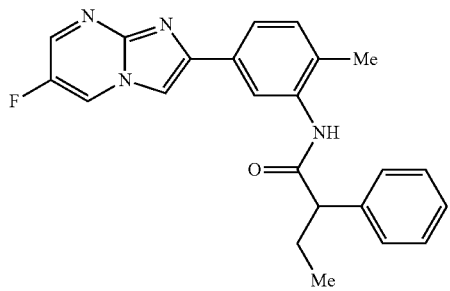
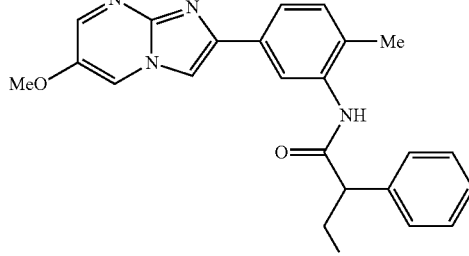
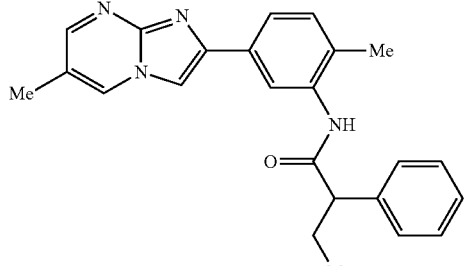

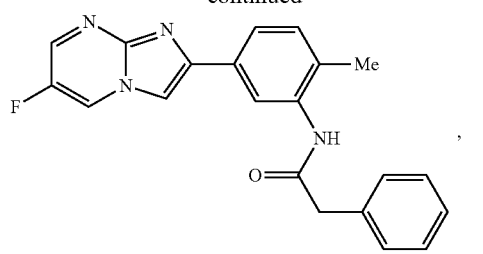
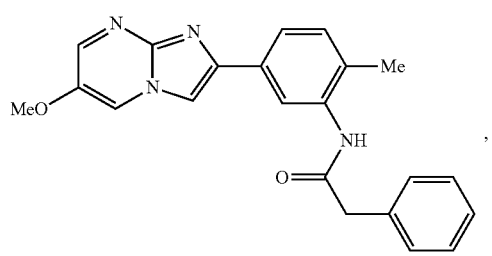
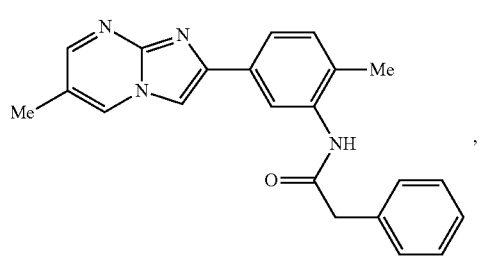
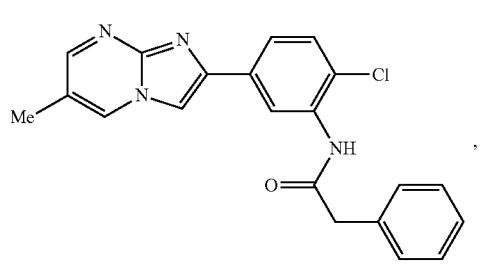
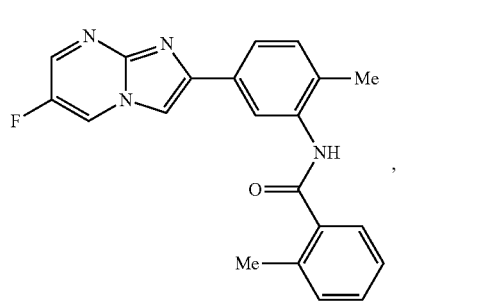
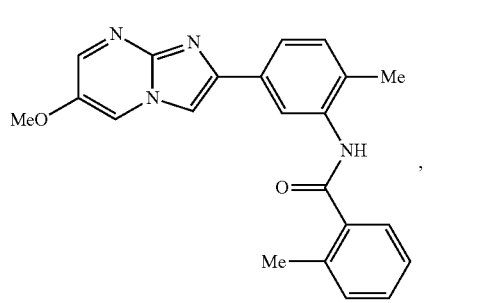
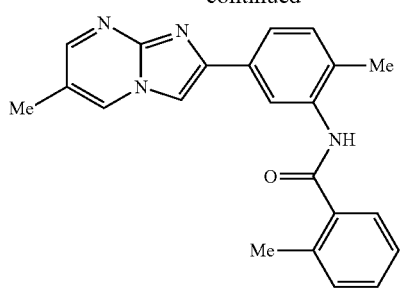
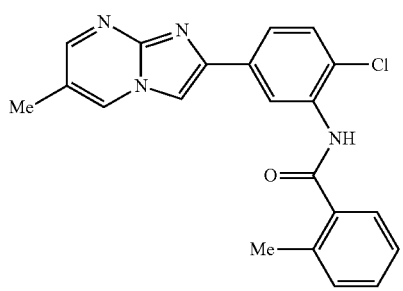
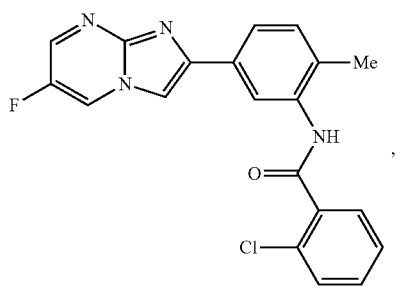
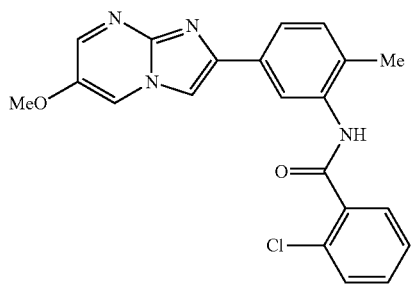
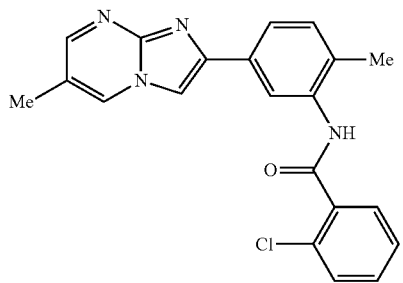
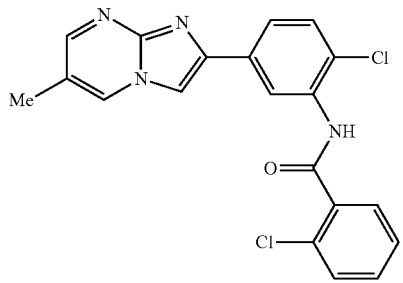

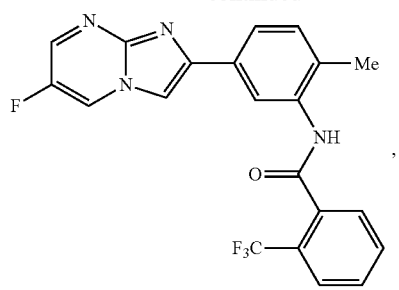
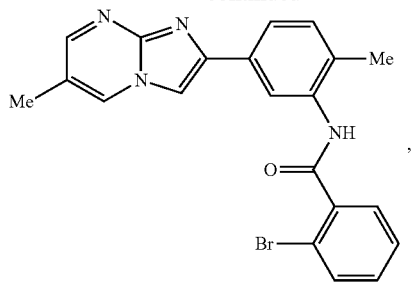
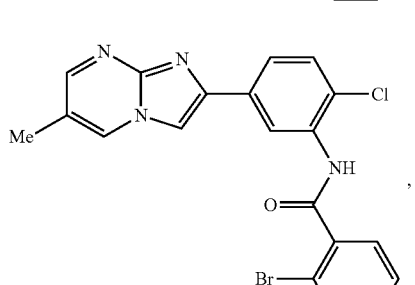
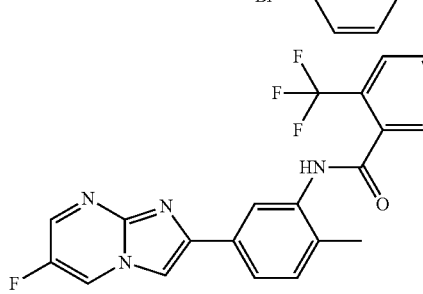
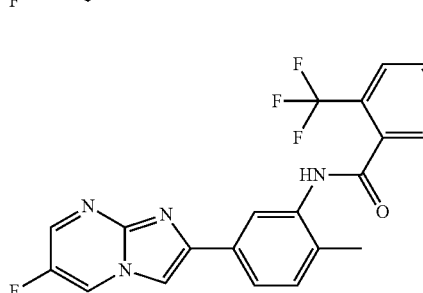
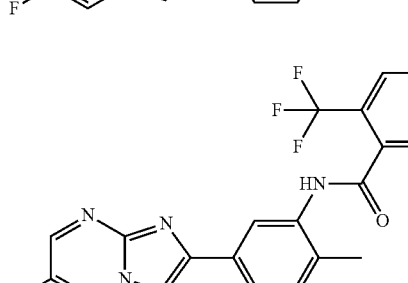
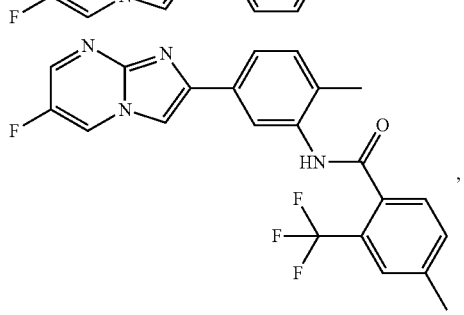

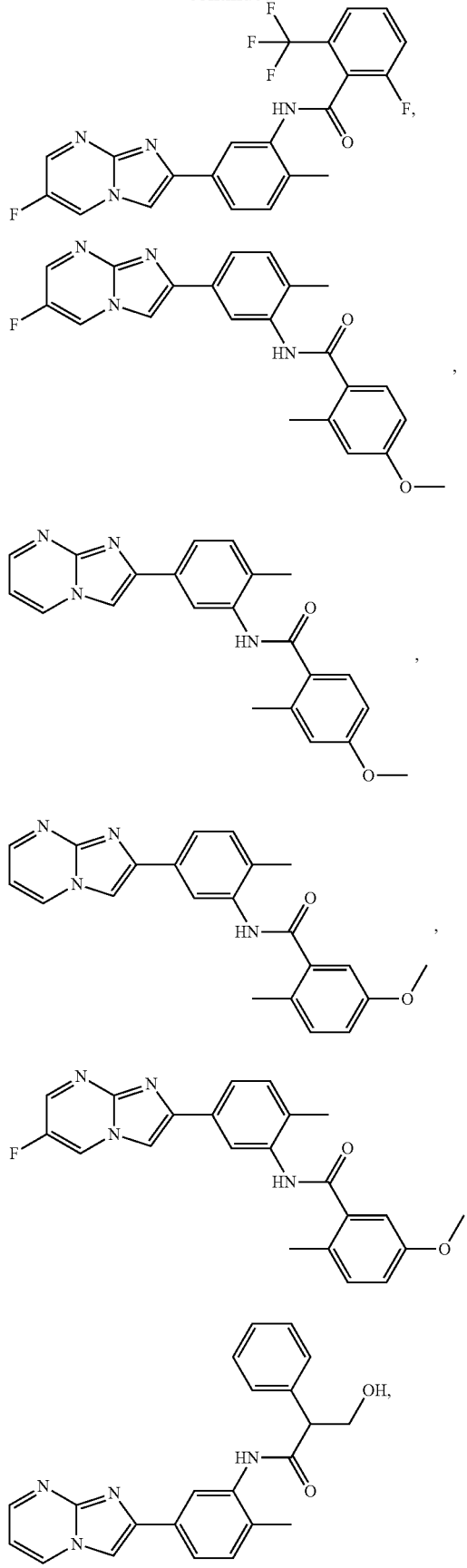

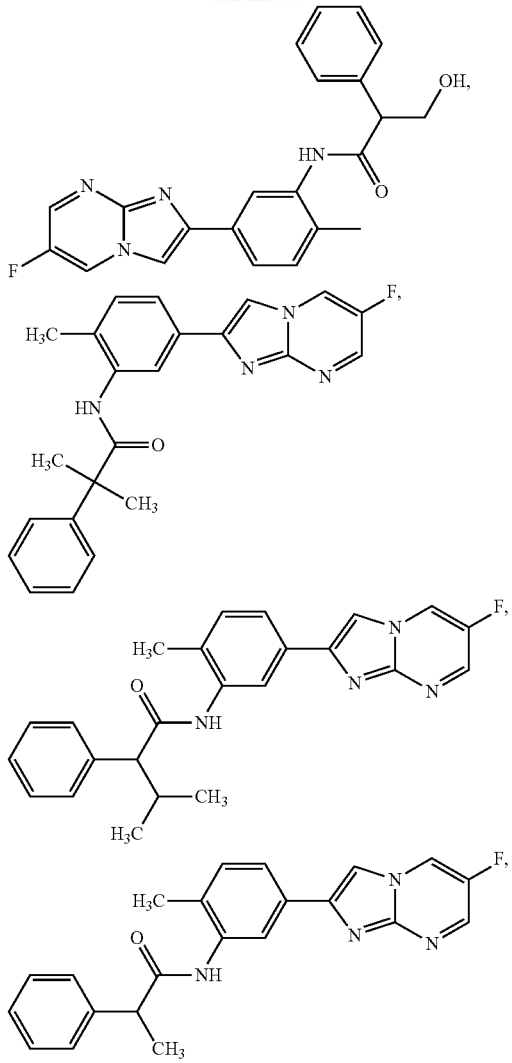

or a pharmaceutically acceptable salt, solvate, hydrate, polymorph, co-crystal, tautomer, stereoisomer, isotopically labeled derivative, or prodrug thereof.

Pharmaceutical Compositions, Kits, and Administration

The present disclosure also provides pharmaceutical compositions comprising a compound described herein and optionally a pharmaceutically acceptable excipient. In certain embodiments, a compound described herein is of Formula (I).

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for enhancing an immune response (e.g., innate and/or adaptive immune response). In certain embodiments, a therapeutically effective amount is an amount effective for treating a disease (e.g., proliferative disease). In certain embodiments, a therapeutically effective amount is an amount effective for serving as an adjuvant in a vaccine for a disease, e.g., proliferative disease, inflammatory disease, autoimmune disease, infectious disease, or chronic disease, or as stand alone anti-infective or immune response modifying agents. In certain embodiments, a prophylactically effective amount is an amount effective for preventing a disease (e.g., proliferative disease, inflammatory disease, autoimmune disease, infectious disease, or chronic disease). In certain embodiments, a prophylactically effective amount is an amount effective for enhancing an immune response (e.g., innate and/or adaptive immune response), and preventing a disease (e.g., proliferative disease, inflammatory disease, autoimmune disease, infectious disease, or chronic disease).

In certain embodiments, the effective amount is an amount effective for enhancing an immune response (e.g., innate and/or adaptive immune response) by at least 10%, at least 20%, at least 30%, at least 40%, at least 50%, at least 60%, at least 70%, at least 80%, at least 90%, at least 95%, or at least 98%. In certain embodiments, the effective amount is an amount effective for enhancing an immune response (e.g., innate and/or adaptive immune response) by not more than 10%, not more than 20%, not more than 30%, not more than 40%, not more than 50%, not more than 60%, not more than 70%, not more than 80%, not more than 90%, not more than 95%, or not more than 98%.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. The use of the compounds described herein in veterinary vaccine is also within the scope of the present disclosure. "A companion animal," as used herein, refers to pets and other domestic animals. Non-limiting examples of companion animals include dogs and cats; livestock such as horses, cattle, pigs, sheep, goats, and chickens; and other animals such as mice, rats, guinea pigs, and hamsters. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat, guinea pig, and hamster), dog, pig, rabbit, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the cell is present in vitro. In certain embodiments, the cell is present in vivo.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical Mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject. In certain embodiments, the compound or composition is administered intradermally, intramuscularly, intravaginally, intravenously, intranasally, orally, subcutaneously, topically, and/or sublingually. In certain embodiments, the compound or composition is administered as a prophylactic. In certain embodiments, the compound or composition is administered as a combination therapy with another immunomodulatory agent, an immunomodulating antibody, an immunomodulating biologic, or an inhibitor of molecular pathways that limits immune responses. In certain embodiments, the immunomodulatory agent is a pattern recognition receptor agonist (e.g., an Alum, or a Toll-like receptor (TLR) Agonist). In certain embodiments, the immunomodulating antibody or immunomodulating biologic is a cytokine, chemokine or colony stimulating factor.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in enhancing an immune response (e.g., innate and/or adaptive immune response) in a subject, biological sample, tissue, or cell), serving as an adjuvant in a vaccine for a disease, e.g., proliferative disease, inflammatory disease, autoimmune disease, infectious disease, or chronic disease, improve bioavailability, improve safety, reduce drug resistance, reduce and/or modify metabolism, inhibit excretion, and/or modify distribution in a subject, biological sample, tissue, or cell, or as stand alone anti-infective or immune response modifying agents. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, inflammatory disease, autoimmune disease, infectious disease, or chronic disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine 1131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is a binder or inhibitor of an HMT (e.g., EZH1, EZH2, DOT1). In certain embodiments, the additional pharmaceutical agent is a protein kinase inhibitor (e.g., tyrosine protein kinase inhibitor). In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, inflammatory disease, autoimmune disease, infectious disease, or chronic disease) in a subject in need thereof. In certain embodiments, the kits are useful for preventing a disease (e.g., proliferative disease, inflammatory disease, autoimmune disease, infectious disease, or chronic disease) in a subject in need thereof. In certain embodiments, the kits are useful as enhancers and/or modifiers of an immune response (e.g., innate and/or adaptive immune response), and/or adjuvants in a vaccine for a disease, (e.g., proliferative disease, inflammatory disease, autoimmune disease, infectious disease, or chronic disease) in a subject, biological sample, tissue, or cell, or as stand alone anti-infective or immune response modifying agents.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, inflammatory disease, autoimmune disease, infectious disease, or chronic disease) in a subject in need thereof. In certain embodiments, the kits and instructions provide for preventing a disease (e.g., proliferative disease, inflammatory disease, autoimmune disease, infectious disease, or chronic disease) in a subject in need thereof. In certain embodiments, the kits and instructions provide for enhancing of an immune response (e.g., innate and/or adaptive immune response) in a subject, biological sample, tissue, or cell. In certain embodiments, the kits and instructions provide for use of the compounds as adjuvants in a vaccine for a disease, (e.g., proliferative disease, inflammatory disease, autoimmune disease, infectious disease, or chronic disease) in a subject, biological sample, tissue, or cell, or as stand alone anti-infective or immune response modifying agents. A kit described herein may include one or more additional pharmaceutical agents described herein as a separate composition.

Methods of Treatment and Uses

The compounds described herein are capable of enhancing an immune response (e.g., innate and/or adaptive immune response). The present disclosure thus also provides methods of enhancing an immune response (e.g., innate and/or adaptive immune response) in a subject, biological sample, tissue, or cell. The present disclosure further provides methods for the compounds as adjuvants in a vaccine for treatment of a wide range of diseases, such as proliferative diseases, inflammatory diseases, autoimmune diseases, infectious diseases, and chronic diseases in a subject in need thereof, or as stand alone anti-infective or immune response modifying agents.

In another aspect, the present disclosure provides methods of enhancing an immune response (e.g., innate and/or adaptive immune response), the methods comprising administering to the subject an effective amount of a compound or pharmaceutical composition described herein.

In another aspect, the present disclosure provides methods of enhancing an immune response (e.g., innate and/or adaptive immune response) in a biological sample, tissue, or cell, the methods comprising contacting the biological sample, tissue, or cell with an effective amount of a compound or pharmaceutical composition described herein.

In certain embodiments, the immune response (e.g., innate and/or adaptive immune response) is enhanced by a compound, pharmaceutical composition, kit, use, or method described herein by at least 1%, at least 3%, at least 10%, at least 20%, at least 30%, at least 40%, at least 50%, at least 60%, at least 70%, at least 80%, or at least 90%. In certain embodiments, the immune response (e.g., innate and/or adaptive immune response) in a subject, biological sample, tissue, or cell is enhanced by a compound, pharmaceutical composition, kit, use, or method described herein by not more than 1%, not more than 3%, not more than 10%, not more than 20%, not more than 30%, not more than 40%, not more than 50%, not more than 60%, not more than 70%, not more than 80%, or not more than 90%.

Another aspect of the present disclosure relates to methods of using the compounds as adjuvants in a vaccine for treating a disease in a subject in need thereof, the methods comprising administering to the subject a therapeutically effective amount of a compound or pharmaceutical composition described herein. Some aspects of the present disclosure provide the vaccine as a subunit vaccine, an attenuated vaccine, or a conjugate vaccine. In some embodiments, a vaccine stimulates the subject's immune system to recognize an antigen as foreign, and enhances the subject's immune response if the subject is later exposed to the pathogen, whether attenuated, inactivated, killed, or not. Vaccines may be prophylactic, for example, preventing or ameliorating a detrimental effect of a future exposure to a pathogen, or therapeutic, for example, activating the subject's immune response to a pathogen after the subject has been exposed to the pathogen. In some embodiments, a vaccine composition is used to protect or treat an organism against a disease (e.g., an infectious disease or cancer). In some embodiments, the vaccine is a subunit vaccine (e.g., a recombinant subunit vaccine), an attenuated vaccine (e.g., containing an attenuated pathogen such as a bacterial cell or a viral genome), a live vaccine (e.g., containing a live attenuated pathogen such as a bacterium or virus), or a conjugated vaccine (e.g., a vaccine containing an antigen that is not very immunogenic covalently attached to an antigen that is more immunogenic). One non-limiting example of a conjugated vaccine comprises a LPS attached to a strong protein antigen. Another aspect of the present disclosure relates to methods of using the compounds as stand alone anti-infective or immune response modifying agents in a subject in need thereof, the methods comprising administering to the subject a therapeutically effective amount of a compound or pharmaceutical composition described herein.

In certain embodiments, a disease described herein is a proliferative disease. In certain embodiments, a disease described herein is cancer. In certain embodiments, a disease described herein is hyperplasia (e.g., germinal center (GC) hyperplasia). In certain embodiments, a disease described herein is brain cancer, breast cancer, or prostate cancer. In certain embodiments, a disease described herein is a benign neoplasm. In certain embodiments, a disease described herein is or is associated with pathological angiogenesis. In certain embodiments, a disease described herein is an inflammatory disease. In certain embodiments, a disease described herein is an autoimmune disease. In certain embodiments, a disease described herein is an infectious disease. In certain embodiments, a disease described herein is an infection by a microbial pathogen (e.g., from a mycobacterium, bacterium, fungus, a virus, parasite, or prion). In certain embodiments, a disease described herein is a microbial infectious disease. In certain embodiments, the infectious disease is a viral infectious disease. In certain embodiments, the viral infectious disease being treated or prevented is an infection with influenza. In certain embodiments, the infectious disease is sepsis. In certain embodiments, the infectious disease is a pediatric infectious disease. In certain embodiments, the infectious disease is a disease of newborns, infants and/or school age children. In certain embodiments, the infectious disease is allergy.

In certain embodiments, the infectious disease is a bacterial infectious disease. In certain embodiments, the bacterial infectious disease being treated or prevented is an infection with a Gram-positive bacteria. Exemplary Gram-positive bacteria include, but are not limited to, *Staphylococcus* spp., *Streptococcus* spp., *Micrococcus* spp., *Peptococcus* spp., *Peptostreptococcus* spp., *Enterococcus* spp., *Bacillus* spp., *Clostridium* spp., *Lactobacillus* spp., *Listeria* spp., *Erysipelothrix* spp., *Propionibacterium* spp., *Eubacterium* spp., *Corynebacterium* spp., Capnocytophaga spp., *Bifidobacterium* spp., and *Gardnerella* spp. Exemplary Gram-positive bacteria include, but are not limited to, *Staphylococcus* spp., *Streptococcus* spp., *Micrococcus* spp., *Peptococcus* spp., *Peptostreptococcus* spp., *Enterococcus* spp., *Bacillus* spp., *Clostridium* spp., *Lactobacillus* spp., *Listeria* spp., *Erysipelothrix* spp., *Propionibacterium* spp., *Eubacterium* spp., and *Corynebacterium* spp. In certain embodiments, the Gram-positive bacteria is a bacteria of the phylum Firmicutes. In certain embodiments, the Gram-positive bacteria is *Streptococcus*.

In certain embodiments, the bacterial infection being treated or prevented is an infection with a Gram-negative bacteria. Exemplary Gram-negative bacteria species include, but are not limited to, *Escherichia, Citrobacter, Enterobacter, Klebsiella, Proteus, Serratia, Shigella, Salmonella, Morganella, Providencia, Edwardsiella, Erwinia, Hafnia, Yersinia, Acinetobacter, Vibrio, Aeromonas, Pseudomonas, Haemophilus, Pasteurella, Campylobacter, Helicobacter, Branhamella, Moraxella, Neisseria, Veillonella, Fusobacterium, Bacteroides, Actinobacillus, Aggregatibacter, Agrobacterium, Porphyromonas, Prevotella, Ruminobacter, Roseburia, Caulobacter, Francisella, Borrelia, Treponema, Brucella, Bordetella,* and *Rickettsia.* In some embodiments, the bacterial infectious agent is *Bacillus anthracis* (causing anthrax), *Bordetella pertussis* (causing whooping cough), *Corynebacterium diphtheriae* (causing diphtheria), *Clostridium tetani* (causing tetanus), *Haemophilus influenzae* type b, pneumococcus (causing pneumococcal infections), Staphylococci spp. (including Group A or B streptococci), *Mycobacterium tuberculosis, Neiserria meningitidis* (causing meningococcal disease), *Salmonella typhi* (causing typhoid), *Vibrio cholerae* (causing Cholera), or *Yersinia pestis* (causing plague). In some embodiments, the bacterial infectious agent is anthrax, diphtheria, tetanus,

*Bordetella* spp., *Haemophilus influenzae* type b, *Neiserria* spp., *Vibrio* spp., cholera, *Yersinia* spp., Staphylococci spp., Streptococci spp., or *Salmonella* spp. In some embodiments, the bacterial infectious disease is anthrax, diphtheria, tetanus, pertussis, *Haemophilus influenzae* type b, pneumococcal infection, meningococcal disease, cholera, plague, Staphylococcal disease, Group A or B streptococcal or pneumococcal infection, or typhoid.

In certain embodiments, the Gram-negative bacteria is *Bordetella pertussis*. In certain embodiments, the bacterial infectious disease is pertussis. In some embodiments, the antigen is a lipopolysaccharide endotoxin (LPS) from a Gram-negative bacterium. Non-limiting examples of Gram-negative bacterial species include: *Neisseria* species including *Neisseria gonorrhoeae* and *Neisseria meningitidis*, Branhamella species including Branhamella *catarrhalis*, *Escherichia* species including *Escherichia coli*, *Enterobacter* species, *Proteus* species including *Proteus mirabilis*, *Pseudomonas* species including *Pseudomonas aeruginosa*, *Pseudomonas mallei*, and *Pseudomonas pseudomallei*, *Klebsiella* species including *Klebsiella pneumoniae*, *Salmonella* species, *Shigella* species, *Serratia* species, *Acinetobacter* species; *Haemophilus* species including *Haemophilus influenzae* and *Haemophilus ducreyi*; *Brucella* species, *Yersinia* species including *Yersinia pestis* and *Yersinia enterocolitica*, *Francisella* species including *Francisella tularensis*, *Pasteurella* species including *Pasteurella multocida*, *Vibrio cholerae*, *Flavobacterium* species, *meningosepticum*, *Campylobacter* species including *Campylobacter jejuni*, *Bacteroides* species (oral, pharyngeal) including *Bacteroides fragilis*, *Fusobacterium* species including *Fusobacterium nucleatum*, *Calymmatobacterium granulomatis*, *Streptobacillus* species including *Streptobacillus moniliformis*, *Legionella* species including *Legionella pneumophila*.

Other types of bacteria include acid-fast bacilli, spirochetes, and actinomycetes.

Examples of acid-fast bacilli include *Mycobacterium* species including *Mycobacterium tuberculosis* and *Mycobacterium leprae*. Examples of spirochetes include *Treponema* species including *Treponema pallidum*, *Treponenia pertenue*, *Borrelia* species including *Borrelia burgdorferi* (Lyme disease), and *Borrelia recurrentis*, and Leptospira species. Examples of actinomycetes include: *Actinomyces* species including *Actinomyces israelii*, and *Nocardia* species including *Nocardia asteroides*.

In certain embodiments, the bacteria is *Escherichia* spp., *Enterobacter* spp. (e.g., *Enterobacter cloacae*), *Salmonella* spp. (e.g., *Salmonella enteritidis, Salmonella typhi*), *Shigella* spp., *Pseudomonas* spp. (e.g., *Pseudomonas aeruginosa, Pseudomonas pachastrellae, Pseudomonas stutzeri*), *Moraxella* spp. (e.g., *Moraxella catarrhalis*), *Neisseria* spp. (e.g., *Neisseria gonorrhoeae, Neisseria meningitidis*), *Helicobacter* spp., (e.g., *Helicobacter pylori*) *Stenotrophomonas* spp., *Vibrio* spp. (e.g., *Vibrio cholerae*), *Legionella* spp. (*Legionella pneumophila*), *Hemophilus* spp. (e.g., *Hemophilus influenzae*), *Klebsiella* spp. (e.g., *Klebsiella pneumoniae*), *Proteus* spp. (e.g., *Proteus mirabilis*), *Serratia* spp. (*Serratia marcescens*), *Streptococcus* spp., *Staphylococcus* spp., *Corynebacterium* spp., *Listeria* spp., and *Clostridium* spp., *Bacillus* spp. (e.g., *Bacillus anthracis*) *Bordetella* spp. (e.g., *Bordetella pertussis*); *Borrelia* spp. (e.g., *Borrelia burgdorferi*); *Brucella* spp. (e.g., *Brucella abortus, Brucella canis, Brucella melitensis, Brucella suis*); *Campylobacter* spp. (e.g., *Campylobacter jejuni*); *Chlamydia* spp. and *Chlamydophila* spp. (e.g., *Chlamydia pneumoniae, Chlamydia trachomatis, Chlamydophila psittaci*); *Clostridium* spp. (e.g., *Clostridium botulinum, Clostridium difficile, Clostridium perfringens, Clostridium tetani*); *Corynebacterium* spp. (e.g., *Corynebacterium diphtheriae*); *Enterococcus* spp. (e.g., *Enterococcus faecalis, Enterococcus faecium*); *Escherichia* spp. (e.g., *Escherichia coli*, Enterotoxic *E. coli*, enteropathogenic *E. coli; E. coli* O157:H7); *Francisella* spp. (e.g., *Francisella tularensis*); *Haemophilus* spp. (e.g., *Haemophilus influenzae*); *Helicobacter* spp. (e.g., *Helicobacter pylori*); *Legionella* spp. (e.g., *Legionella pneumophila*); Leptospira spp. (e.g., Leptospira interrogans); *Listeria* spp. (e.g., *Listeria monocytogenes*); *Mycobacterium* spp. (e.g., *Mycobacterium leprae, Mycobacterium tuberculosis, Mycobacterium ulcerans*); *Mycoplasma* spp. (e.g., *Mycoplasma pneumoniae*); *Neisseria* spp. (e.g., *Neisseria gonorrhoeae, Neisseria meningitidis*); *Pseudomonas* spp. (e.g., *Pseudomonas aeruginosa*); *Rickettsia* spp. (e.g., *Rickettsia rickettsii*); *Salmonella* spp. (e.g., *Salmonella typhi, Salmonella typhimurium*); *Shigella* spp. (e.g., *Shigella sonnei*); *Staphylococcus* spp. (e.g., *Staphylococcus aureus, Staphylococcus epidermidis, Staphylococcus saprophyticus*); *Streptococcus* spp. (e.g., *Streptococcus agalactiae, Streptococcus pneumoniae, Streptococcus pyogenes*); *Treponema* spp. (e.g., *Treponema pallidum*); *Pseudodiomarina* spp. (e.g., *P. maritima*); *Marinobacter* spp. (e.g., *Marinobacter hydrocarbonoclasticus, Marinobacter vinifirmus*) *Alcanivorax* spp. (e.g., *alcanivorax dieselolei*); *Acetinobacter* spp. (e.g., *A. venetianus*); *Halomonas* spp. (e.g., *H. shengliensis*); *Labrenzia* spp.; *Microbulifer* spp. (e.g., *M. schleiferi*); *Shewanella* spp. (e.g., *S. algae*); *Vibrio* spp. (e.g., *Vibrio cholerae, Vibrio alginolyticus, Vibrio hepatarius*); and *Yersinia* spp. (e.g., *Yersinia pestis*).

In certain embodiments, the infectious disease is cancer. In certain embodiments, the infectious disease is a fibrotic disease, a cardiovascular disease, a graft rejection, or graft-versus-host disease. In certain embodiments, the bacterial infectious disease is anthrax, diphtheria, tetanus, pertussis, *Haemophilus influenzae* type b, pneumococcal infections, meningococcal disease, cholera, plague, Staphylococcal disease, a Group A streptococcal infection, a Group A pneumococcal infection, a group B streptococcal infection, a group B pneumococcal infection, or typhoid. In certain embodiments, the infectious disease is a mycobacterial infectious disease. In certain embodiments, the mycobacterial infectious disease is a tuberculosis infection or a non-tuberculous mycobacterial infection.

In certain embodiments, the infectious disease is a viral infectious disease. In certain embodiments, the viral infectious disease is an infection by Retroviruses, human immunodeficiency viruses including HIV-1, HDTV-III, LAVE, HTLV-III/LAV, HIV-III, HIV-LP, Cytomegaloviruses (CMV), Picornaviruses, polio viruses, hepatitis A virus, enteroviruses, human Coxsackie viruses, rhinoviruses, echoviruses, Calciviruses, Togaviruses, equine encephalitis viruses, rubella viruses, Flaviruses, dengue viruses, encephalitis viruses, yellow fever viruses, Coronaviruses, Rhabdoviruses, vesicular stomatitis viruses, rabies viruses, Filoviruses, ebola virus, Paramyxoviruses, parainfluenza viruses, mumps virus, measles virus, respiratory syncytial virus (RSV), Orthomyxoviruses, influenza viruses, Bungaviruses, Hantaan viruses, phleboviruses and Nairo viruses, Arena viruses, hemorrhagic fever viruses, reoviruses, orbiviruses, rotaviruses, Birnaviruses, Hepadnaviruses, Hepatitis B virus, parvoviruses, Papovaviridae, papilloma viruses, polyoma viruses, Adenoviruses, Herpesviruses including herpes simplex virus 1 and 2, varicella zoster virus, Poxviruses, variola viruses, vaccinia viruses, Irido viruses, African swine fever virus, delta hepatitis virus, non-A, non-B hepatitis virus, Hepatitis C, Norwalk viruses, astroviruses, and unclassified viruses. In certain embodiments, the viral infectious disease is an infection by adenovirus, poliomyelitis, Ebola, herpes viruses (e.g., herpes simplex virus), cytomegalovirus and varicella-zoster, measles, mumps, rubella, hepatitis A, hepatitis B, hepatitis C, human papilloma virus, Influenza, rabies, Japanese encephalitis, rotavirus, human immunodeficiency virus, respiratory syncytial virus, smallpox, yellow fever, or Zika Virus. In certain embodiments, the viral infectious disease is polio, chickenpox, or shingles. In certain embodiments, the viral infectious disease is an infection by human immunodeficiency virus (HIV) or respiratory syncytial virus (RSV). In certain embodiments, the infectious disease is a parasitic infectious disease. In certain embodiments, the parasitic infectious disease is an infection by malaria, *Leishmania*, another protozoan, or a helminth. In certain embodiments, the parasitic infectious disease is an infection by *Plasmodium* species, such as *Plasmodium* species including *Plasmodium falciparum, Plasmodium malariae, Plasmodium ovale*, and *Plasmodium vivax* and *Toxoplasma gondii*. Blood-borne and/or tissues parasites include *Plasmodium* species, *Babesia* species including *Babesia microli* and *Babesia divergens, Leishmania* species including *Leishmania tropica, Leishmania species, Leishmania braziliensis, Leishmania donovani, Trypanosoma* species including *Trypanosoma ganibiense, Trypanosoma rhodesiense* (African sleeping sickness), and *Trypanosoma cruzi* (Chagas' disease). In certain embodiments, the parasitic infectious disease is malaria or leishmaniasis.

In certain embodiments, the infectious disease is a fungal infectious disease. In certain embodiments, the fungal infectious disease is *Cryptococcus* species including *Cryptococcus neoformans, Histoplasma* species including *Histoplasma capsulatum, Coccidioides* species including *Coccidioides immitis, Paracoccidioides* species including *Paracoccidioides brasiliensis, Blastomyces* species including *Blastomyces dermatitidis, Chlamydia* species including *Chlamydia trachomatis, Candida* species including *Candida albicans, Sporothrix* species including *Sporothrix schenckii, Aspergillus* species, and fungi of mucormycosis. In some embodiments, the fungus is fungus is *Candida* spp., *Aspergillus* spp., *Cryptococcus* spp., *Mucormycete, Blastomyces dermatitidis* (causing blastomycosis), or endemic mycosis causing fungus such as *Histoplasma capsulatum* (causing histoplasmosis), or *Sporothrix schenckii* (causing sporotrichosis). In certain embodiments, the vaccine provides heterologous protection against a range of pathogens. Other medically relevant microorganisms have been described extensively in the literature, e.g., see C. G. A Thomas, Medical Microbiology, Bailliere Tindall, Great Britain 1983, incorporated herein by reference. In certain embodiments, a disease described herein is a chronic disease. In certain embodiments, the chronic disease is arthritis, cardiovascular disease such as heart disease, stroke, cancer (e.g., breast cancer or colon cancer), chronic respiratory diseases, diabetes, epilepsy, seizures, obesity, or an oral health problem.

In still another aspect, the present disclosure provides methods of preventing a disease to be treated with a compound or pharmaceutical composition described herein in a subject in need thereof, the methods comprising administering to the subject a prophylactically effective amount of a compound or pharmaceutical composition described herein.

In another aspect, the present disclosure provides the compounds described herein for use in a method described herein (e.g., a method of enhancing an immune response (e.g., innate and/or adaptive immune response), a method of treating a disease (e.g., proliferative disease, inflammatory disease, autoimmune disease, infectious disease, or chronic disease), and a method of treating and/or preventing a disease by using the compounds as medicaments or adjuvants in a vaccine for the disease (e.g., proliferative disease, inflammatory disease, autoimmune disease, infectious disease, or chronic disease), or as stand alone anti-infective or immune response modifying agents. In certain embodiments, the present disclosure provides the compounds described herein for use as immunomodulators. In certain embodiments, the medicament is an immunomodulator.

In another aspect, the present disclosure provides the compounds described herein for use in treating and/or preventing a proliferative disease in a subject. In another aspect, the present disclosure provides the compounds described herein for use as a medicament.

In still another aspect, the present disclosure provides the pharmaceutical compositions described herein for use in a method described herein (e.g., a method of enhancing an immune response (e.g., innate and/or adaptive immune response), a method of treating a disease (e.g., proliferative disease, inflammatory disease, autoimmune disease, infectious disease, or chronic disease), and a method of treating and/or preventing a disease by using the compounds as medicaments or adjuvants in a vaccine for the disease (e.g., proliferative disease, inflammatory disease, autoimmune disease, infectious disease, or chronic disease), or as stand alone anti-infective or immune response modifying agents.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Preparation of the Compounds Described Herein

The compounds provided herein can be prepared from readily available starting materials using the following general methods and procedures. For example, compounds of Formula (I) can be prepared according to Scheme 1. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Preparation of Examples

Scheme 1-preparation of example 1

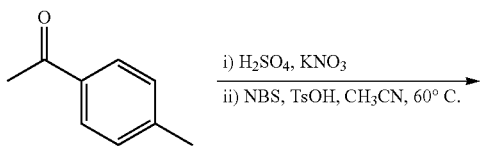

83

-continued

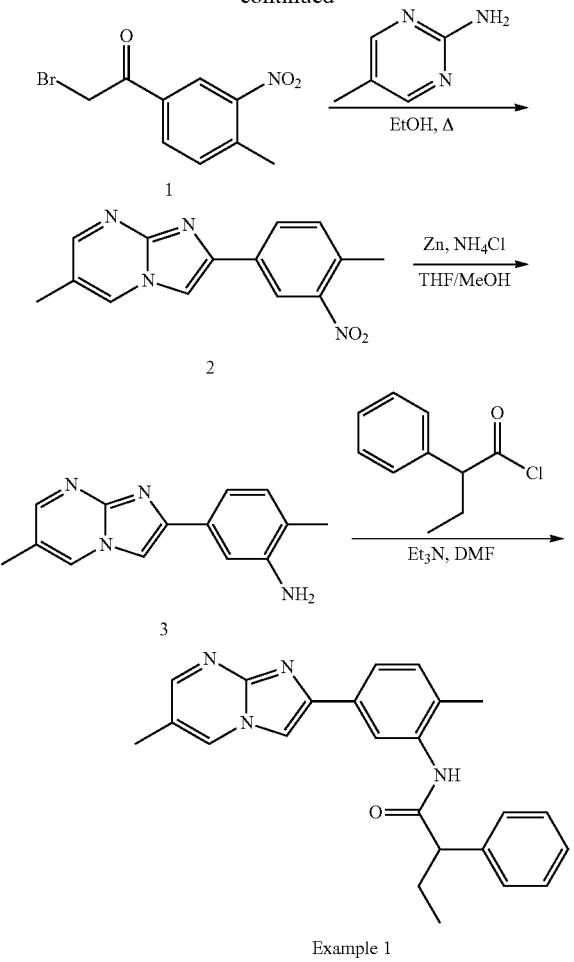

Example 1

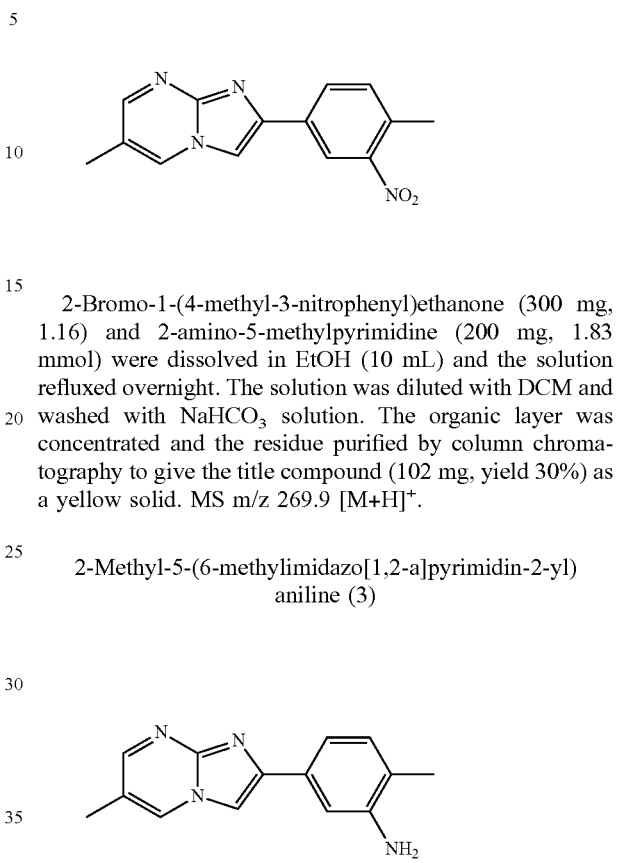

2-Bromo-1-(4-methyl-3-nitrophenyl)ethanone (1)

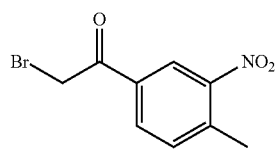

4'-Methylacetophenone (1 g, 7.5 mmol) was dissolved in conc. H$_2$SO$_4$ (10 mL) and the solution was cooled to 0° C. KNO$_3$ (1 g, 9.9 mmol) was added in portions, and the mixture was stirred at 0° C. for 2 hours, then poured onto crushed ice (100 g), and extracted with EtOAc (2×50 mL). The organic phase was washed with brine and concentrated to give 1.3 g of a yellow solid. The nitro intermediate (200 mg, 1.1 mmol) was dissolved in acetonitrile (2 mL). NBS (237 mg, 1.3 mmol) and p-TsOH (200 mg, 1.1) were added. The reaction mixture was heated at 60° C. for 4 hours, then diluted with EtOAc (20 mL) and washed with sat. Na$_2$S$_2$O$_3$ solution and brine. The organic layer was concentrated to give the title compound (260 mg, yield 91%) as a yellow solid. $^1$H NMR (400 MHz, CDCl$_3$): δ 8.56 (s, 1H), 8.12 (d, 1H), 7.52 (d, 1H), 4.46 (s, 2H), 2.70 (s, 3H).

84

6-Methyl-2-(4-methyl-3-nitrophenyl)imidazo[1,2-a]pyrimidine (2)

2-Bromo-1-(4-methyl-3-nitrophenyl)ethanone (300 mg, 1.16) and 2-amino-5-methylpyrimidine (200 mg, 1.83 mmol) were dissolved in EtOH (10 mL) and the solution refluxed overnight. The solution was diluted with DCM and washed with NaHCO$_3$ solution. The organic layer was concentrated and the residue purified by column chromatography to give the title compound (102 mg, yield 30%) as a yellow solid. MS m/z 269.9 [M+H]$^+$.

2-Methyl-5-(6-methylimidazo[1,2-a]pyrimidin-2-yl)aniline (3)

6-Methyl-2-(4-methyl-3-nitrophenyl)imidazo[1,2-a]pyrimidine (600 mg, 2.24 mmol) was dissolved in THF and methanol (3:1, 4 mL). Zinc powder (2.3 g, 35.4 mmol) and NH$_4$C$_1$ (2 g, 37.0 mmol) were added to the solution and the mixture was stirred for 1 hour. The solid was filtered, and the filtrate was concentrated, dissolved in EtOAc, and then washed with water. The organic phase was concentrated to give compound the title compound (400 mg, 75% yield) as a yellow solid. MS m/z 238.7 [M+H]$^+$.

2-Bromo-1-(4-chloro-3-nitrophenyl)ethan-1-one (4)

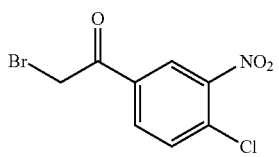 [SMILES: O=C(CBr)c1ccc(Cl)c([N+](=O)[O-])c1]

2-Bromo-1-(4-chloro-3-nitrophenyl)ethan-1-one was prepared using a similar procedure to that described for 1, from 4'-chloroacetophenone. $^1$H NMR (400 MHz, DMSO-d6): δ 8.62 (s, 1H), 8.26 (d, 1H), 8.00 (d, 1H), 5.02 (s, 2H).

Anilines 5-8 were prepared by similar methods to 3, from the corresponding aminopyrimidine and either 1 or 4.

| Aniline | Name | ¹H NMR (d₆-DMSO) | m/z [M + 1]⁺ | Starting materials |
|---|---|---|---|---|
| 5 | 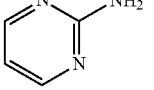 5-(Imidazo[1,2-a]pyrimidin-2-yl)-2-methylaniline | (500 MHz) 8.92 (m, 1H), 8.48 (m, 1H), 8.16 (s, 1H), 7.32 (d, 1H), 7.09 (d, 1H), 7.00 (m, 2H), 4.95 (s, 2H), 2.09 (s, 3H) | 224.91 | and 1 |
| 6 | 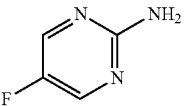 5-(6-Fluoromidazo[1,2-a]pyrimidin-2-yl)-2-methylaniline | (500 MHz) 9.18 (m, 1H), 8.65 (d, 1H), 8.18 (s, 1H), 7.31 (d, 1H), 7.09 (m, 1H), 7.00 (d, 1H), 4.95 (s, 2H), 2.09 (s, 3H) | 242.98 | and 1 |
| 7 | 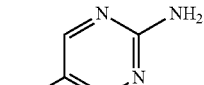 5-(6-Fluoromidazo[1,2-a]pyrimidin-2-yl)-2-methylaniline | (500 MHz) 8.66 (d, 1H), 8.36 (d, 1H), 8.05 (s, 1H), 7.27 (d, 1H), 7.05 (m, 1H), 6.98 (d, 1H), 4.92 (s, 2H), 3.85 (s, 3H), 2.08 (s, 3H) | 254.68 | and 1 |
| 8 | 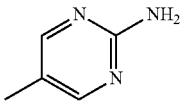 2-Chloro-5-(6-methylimidazo[1,2-a]pyrimidin-2-yl)aniline | | 259.1 | and 4 |

Example 1 FRF-02-144-1

N-(2-Methyl-5-(6-methylimidazo[1,2-a]pyrimidin-2-yl)phenyl)-2-phenylbutanamide

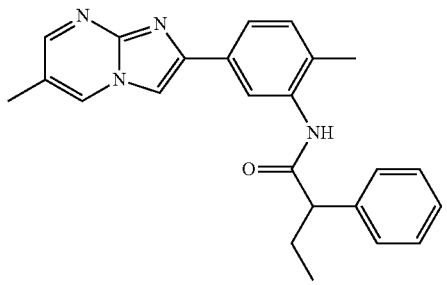 [SMILES: CCC(C(=O)Nc1cc(-c2cn3cc(C)cnc3n2)ccc1C)c1ccccc1]

2-Methyl-5-(6-methylimidazo[1,2-a]pyrimidin-2-yl)aniline (75 mg, 0.32 mmol) was dissolved in DMF (5 mL). Triethylamine (0.09 mL, 0.64 mmol) and 2-phenylbutanoyl chloride (150 mg, 0.82 mmol) were added and the mixture was stirred for 1 hour. The reaction mixture was diluted with EtOAc (20 mL) and washed with sat. NaHCO₃ solution (20 mL). The organic phase was concentrated and purified by flash chromatography to give the title compound (26 mg, 21% yield). ¹H NMR (400 MHz, DMSO-d6): δ 9.59 (s, 1H), 8.72 (s, 1H), 8.41 (d, 1H), 8.23 (s, 1H), 7.90 (s, 1H), 7.68 (d, 1H), 7.44 (m, 2H), 7.37 (m, 2H), 7.27 (m, 2H), 3.69 (m, 1H), 2.30 (s, 3H), 2.11 (s, 3H), 2.10 (m, 1H), 1.74 (m, 1H), 0.94 (t, 3H). MS m/z 385.3 [M+H]⁺.

Example 2 FRF-02-119

N-(5-(6-Fluoroimidazo[1,2-a]pyrimidin-2-yl)-2-methylphenyl)-2-phenylbutanamide

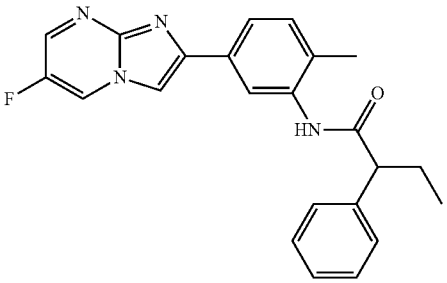 [SMILES: CCC(C(=O)Nc1cc(-c2cn3cc(F)cnc3n2)ccc1C)c1ccccc1]

2-Phenylbutanoic acid (16 mg, 0.099 mmol), diisopropylethylamine (29 uL, 0.165 mmol) and HATU (38 mg, 0.0099 mmol) were dissolved in DMF (6 mL). After 20 minutes, 5-(6-fluoroimidazo[1,2-a]pyrimidin-2-yl)-2-methylaniline (20 mg, 0.082 mmol) was added. After stirring for 18 hours, further portions of 2-phenylbutanoic acid (8 mg), diisopropylethylamine (15 uL) and HATU (18.5 mg) were added, and the mixture stirred for a further 4 hours. The mixture was diluted with DCM, washed with brine, concentrated and the residue purified by column chromatography on silica gel (0 to 5% MeOH in DCM) to give the title compound (19 mg, 56% yield). ¹H NMR (500 MHz, DMSO-d6): δ 9.57 (s, 1H), 9.18 (m, 1H), 8.69 (d, 1H), 8.33 (s, 1H), 7.93 (d, 1H), 7.70

(m, 1H), 7.45 (m, 2H), 7.36 (m, 2H), 7.27 (m, 2H), 3.70 (m, 1H), 2.12 (s, 3H), 2.09 (m, 1H), 1.74 (m, 1H), 0.94 (t, 3H). MS m/z 389.16 [M+H]⁺.

Examples 3-31 shown below were prepared by similar methods to Examples 1 and 2, from the corresponding aniline and either the acid chloride or carboxylic acid.

| Example (and FRF number) | Name | | ¹H NMR (d₆-DMSO) | m/z [M + 1]⁺ | Starting materials | |
|---|---|---|---|---|---|---|
| 3 FRF-02-162-1 | 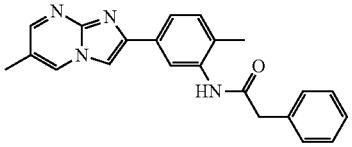 N-(2-Methyl-5-(6-methylimidazo[1,2-a]pyrimidin-2-yl)phenyl)-2-phenylacetamide | | (400 MHz) 9.60 (s, 1H), 8.73 (s, 1H), 8.40 (s, 1H), 8.22 (s, 1H), 8.00 (s, 1H), 7.69 (d, 1H), 7.38 (m, 4H), 7.28 (m, 2H), 3.71 (s, 2H), 2.30 (s, 3H), 2.20 (s, 3H) | 357.4 | 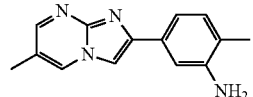 and 2-phenylacetyl chloride | |
| 4 FRF-02-162-2 | 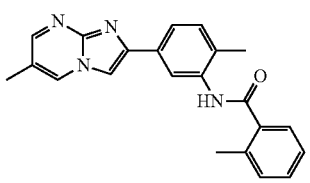 2-Methyl-N-(2-methyl-5-(6-methylimidazo[1,2-a]pyrimidin-2-yl)phenyl)benzamide | | (400 MHz) 9.86 (s, 1H), 8.76 (s, 1H), 8.42 (d, 1H), 8.27 (s, 1H), 8.05 (s, 1H), 7.77 (d, 1H), 7.56 (d, 1H), 7.41 (m, 1H), 7.34 (m, 3H), 2.48 (s, 3H), 2.32 (s, 3H), 3 protons masked by DMSO | 357.4 | 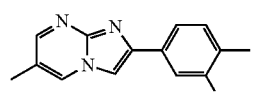 and 2-methylbenzoyl chloride | |
| 5 FRF-02-144-2 | 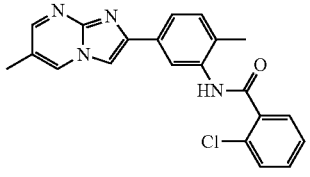 [SMILES: Cc1cnc2nc(-c3ccc(C)c(NC(=O)c4ccccc4Cl)c3)cn2c1] 2-Chloro-N-(2-methyl-5-(6-methylimidazo[1,2-a]pyrimidin-2-yl)phenyl)benzamide | | (400 MHz) 10.08 (s, 1H), 8.76 (s, 1H), 8.43 (s, 1H), 8.28 (s, 1H), 8.08 (s, 1H), 7.77 (d, 1H), 7.68 (d, 1H), 7.59 (d, 1H), 7.49 (m, 2H), 7.35 (d, 1H), 2.33 (s, 3H), 2.32 (s, 3H) | 377.3 | 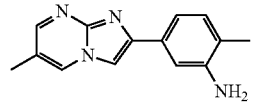 and 2-chlorobenzoyl chloride | |
| 6 FRF-02-144-3 | 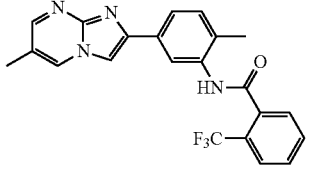 N-(2-Methyl-5-(6-methylimidazo[1,2-a]pyrimidin-2-yl)phenyl)-2-(trifluoromethyl)benzamide | | (400 MHz) 10.13 (s, 1H), 8.77 (s, 1H), 8.46 (d, 1H), 8.27 (s, 1H), 8.06 (s, 1H), 7.88 (d, 1H), 7.77 (m, 4H), 7.35 (d, 1H), 2.31 (s, 6H) | 411.2 | 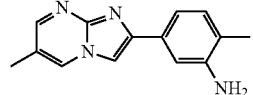 and (trifluoromethyl)benzoyl chloride | |
| 7 FRF-02-118 | 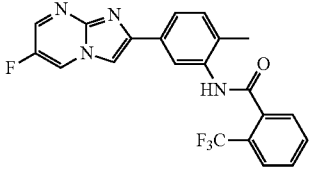 N-(5-(6-Fluoroimidazo[1,2-a]pyrimidin-2-yl)-2-methylphenyl)-2-(trifluoromethyl)benzamide | | (500 MHz) 10.13 (s, 1H), 9.23 (m, 1H), 8.72 (d, 1H), 8.37 (s, 1H), 8.09 (d, 1H), 7.87 (d, 1H), 7.82 (m, 3H), 7.77 (m, 1H), 7.38 (d, 1H), 2.32 (s, 3H) | 414.86 | 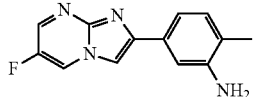 and (trifluoromethyl)benzoyl chloride | |

| Example (and FRF number) | Name | <sup></sup>1H NMR (d<sub>6</sub>-DMSO) | m/z [M + 1]+ | Starting materials |
|---|---|---|---|---|
| 8 FRF-02-117 | 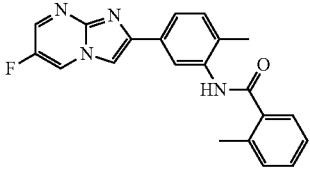 N-(5-(6-Fluoroimidazo[1,2-a]pyrimidin-2-yl)-2-methylphenyl)-2-methylbenzamide | (500 MHz) 9.87 (s, 1H), 9.23 (m, 1H), 8.72 (d, 1H), 8.38 (s, 1H), 8.08 (d, 1H), 7.79 (d, 1H), 7.57 (d, 1H), 7.40 (m, 1H), 7.37 (d, 1H), 7.33 (m, 2H), 2.48 (s, 3H), 2.33 (s, 3H) | 361.22 | 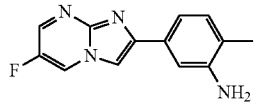 and 2-methylbenzoyl chloride |
| 9 FRF-02-116 | 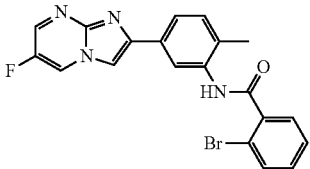 2-Bromo-N-(5-(6-fluoroimidazo[1,2-a]pyrimidin-2-yl)-2-methylphenyl-benzamide | (500 MHz) 10.07 (s, 1H), 9.23 (m, 1H), 8.72 (d, 1H), 8.38 (s, 1H), 8.12 (d, 1H), 7.79 (m, 1H), 7.75 (d, 1H), 7.65 (m, 1H), 7.53 (m, 1H), 7.44 (m, 1H), 7.37 (d, 1H), 2.36 (s, 3H) | 425.3 | 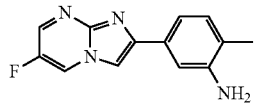 and 2-bromobenzoyl chloride |
| 10 FRF-02-115 | 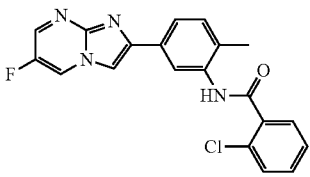 2-Chloro-N-(5-(6-fluoroimidazo[1,2-a]pyrimidin-2-yl)-2-methylphenyl)benzamide | (500 MHz) 10.09 (s, 1H), 9.23 (m, 1H), 8.72 (d, 1H), 8.38 (s, 1H), 8.11 (s, 1H), 7.79 (m, 1H), 7.68 (m, 1H), 7.59 (d, 1H), 7.52 (m, 2H), 7.38 (d, 1H), 2.35 (s, 3H) | 381.25 | 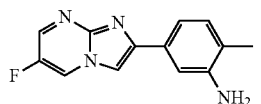 and 2-chlorobenzoyl chloride |
| 11 FRF-02-137 | 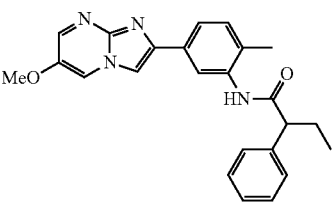 N-(5-(6-Methoxyimidazo[1,2-a]pyrimidin-2-yl)-2-methylphenyl)-2-phenylbutanamide | (500 MHz) 9.56 (s, 1H), 8.64(d, 1H), 8.39 (d, 1H), 8.20 (s, 1H), 7.88 (s, 1H), 7.65 (m, 1H), 7.45 (m, 2H), 7.36 (m, 2H), 7.26 (m, 2H), 3.85 (s, 3H), 3.69 (m, 1H), 2.11 (s, 3H), 2.09 (m, 1H), 1.74 (m, 1H), 0.94 (t, 3H) | 401.4 | 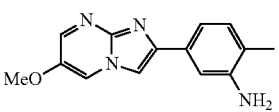 and 2-phenylbutanoic acid |
| 12 FRF-02-135 | 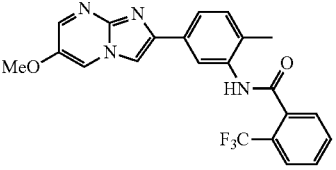 N-(5-(6-Methoxyimidazo[1,2-a]pyrimidin-2-yl)-2-methylphenyl)-2-(trifluoromethyl)benzamide | (500 MHz) 10.11 (s, 1H), 8.68 (d, 1H), 8.42 (d, 1H), 8.23 (s, 1H), 8.04 (s, 1H), 7.87 (d, 1H), 7.81 (m, 2H), 7.74 (m, 2H), 7.35 (d, 1H), 3.86 (s, 3H), 2.31 (s, 3H) | 426.9 | 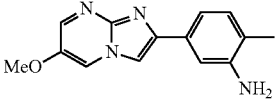 and 2-trifluoromethyl)benzoyl chloride |

| Example (and FRF number) | Name | ¹H NMR (d₆-DMSO) | m/z [M + 1]⁺ | Starting materials |
|---|---|---|---|---|
| 13 FRF-02-134 | N-(5-(6-Methoxyimidazo[1,2-a]pyrimidin-2-yl)-2-methylphenyl)-2-methylbenzamide | (500 MHz) 9.85 (s, 1H), 8.68 (d, 1H), 8.41 (d, 1H), 8.24 (s, 1H), 8.03 (s, 1H), 7.75 (m, 1H), 7.57 (d, 1H), 7.40 (m, 1H), 7.33 (m, 3H), 3.86 (s, 3H), 2.48 (s, 3H), 2.34 (s, 3H) | 372.98 | and 2-methylbenzoyl chloride |
| 14 FRF-02-132 | 2-Bromo-N-(5-(6-methoxyimidazo[1,2-a]pyrimidin-2-yl)-2-methylphenyl)benzamide | (500 MHz) 10.05 (s, 1H), 8.68 (d, 1H), 8.42 (d, 1H), 8.24 (s, 1H), 8.07 (s, 1H), 7.75 (m, 2H), 7.65 (m, 1H), 7.53 (m, 1H), 7.44 (m, 1H), 7.34 (m, 1H), 3.86 (s, 3H), 2.34 (s, 3H) | 439.09 | and 2-bromobenzoyl chloride |
| 15 FRF-02-131 | 2-Chloro-N-(5-(6-methoxyimidazo[1,2-a]pyrimidin-2-yl)-2-methylphenyl)benzamide | (500 MHz) 10.06 (s, 1H), 8.68 (d, 1H), 8.42 (d, 1H), 8.24 (s, 1H), 8.06 (s, 1H), 7.75 (m, 1H), 7.67 (m, 1H), 7.59 (d, 1H), 7.51 (m, 2H), 7.35 (d, 1H), 3.86 (s, 3H), 2.33 (s, 3H) | 393.22 | and 2-chlorobenzoyl chloride |
| 16 FRF-02-166 | 5-Fluoro-N-(5-(6-fluoroimidazo[1,2-a]pyrimidin-2-yl)-2-methylphenyl)-2-(trifluoromethyl)benzamide | (500 MHz) 10.19 (s, 1H), 9.24 (m, 1H), 8.72 (d, 1H), 8.36 (s, 1H), 8.12 (s, 1H), 7.97 (m, 1H), 7.80 (m, 2H), 7.59 (m, 1H), 7.38 (d, 1H), 2.32 (s, 3H) | 433.3 | and 5-fluoro-2-(trifluoromethyl)benzoic acid |
| 17 FRF-02-167 | 4-Fluoro-N-(5-(6-fluoroimidazo[1,2-a]pyrimidin-2-yl)-2-methylphenyl)-2-(trifluoromethyl)benzamide | (500 MHz) 10.15 (s, 1H), 9.23 (m, 1H), 8.72 (d, 1H), 8.37 (s, 1H), 8.10 (s, 1H), 7.92 (m, 1H), 7.81 (m, 2H), 7.72 (m, 1H), 7.38 (d, 1H), 2.31 (s, 3H) | 433.28 | and 4-fluoro-2-(trifluoromethyl)benzoic acid |

| Example (and FRF number) | Name | ¹H NMR (d₆-DMSO) | m/z [M + 1]⁺ | Starting materials |
|---|---|---|---|---|
| 18 FRF-02-169 | 4-Chloro-N-(5-(6-fluoroimidazo[1,2-a]pyrimidin-2-yl)-2-methylphenyl)-2-(trifluoromethyl)benzamide | (500 MHz) 10.17 (s, 1H), 9.23 (m, 1H), 8.72 (d, 1H), 8.36 (s, 1H), 8.10 (s, 1H), 7.98 (d, 1H), 7.94 (m, 1H), 7.87 (d, 1H), 7.80 (m, 1H), 7.37 (d, 1H), 2.31 (s, 3H) | 449.17 | and 4-chloro-2-(trifluoromethyl)benzoic acid |
| 19 FRF-02-171 | N-(5-(6-Fluoroimidazo[1,2-a]pyrimidin-2-yl)-2-methylphenyl)-4-methyl-2-(trifluoromethyl)benzamide | (500 MHz) 10.05 (s, 1H), 9.23 (m, 1H), 8.71 (d, 1H), 8.36 (s, 1H), 8.07 (s, 1H), 7.79 (m, 1H), 7.69 (m, 2H), 7.62 (d, 1H), 7.36 (d, 1H), 2.46 (s, 3H), 2.31 (s, 3H) | 428.93 | and 4-methyl-2-(trifluoromethyl)benzoic acid |
| 20 FRF-02-174-1 | N-(2-Chloro-5-(6-methylimidazo[1,2-a]pyrimidin-2-yl)phenyl)-2-phenylbutanamide | (400 MHz) 9.78 (s, 1H), 8.74 (s, 1H), 8.44 (d, 1H), 8.32 (s, 1H), 8.22 (s, 1H), 7.78 (d, 1H), 7.54 (d, 1H), 7.44 (m, 2H), 7.36 (m, 2H), 7.27 (m, 1H), 3.80 (m, 1H), 2.31 (s, 3H), 2.09 (m, 1H), 1.74 (m, 1H), 0.93 (t, 3H) | 405.3 | and 2-phenylbutanoyl chloride |
| 21 FRF-02-174-2 | N-(2-Chloro-5-(6-methylimidazo[1,2-a]pyrimidin-2-yl)phenyl)-2-(trifluoromethyl)benzamide | (400 MHz) 10.43 (s, 1H), 8.79 (s, 1H), 8.46 (s, 1H), 8.38 (s, 1H), 8.26 (s, 1H), 7.81 (m, 5H), 7.63 (d, 1H), 2.32 (s, 3H) | 431.3 | and 2-(trifluoromethyl)benzoyl chloride |
| 22 FRF-02-175 | 2-Fluoro-N-(5-(6-fluoroimidazo[1,2-a]pyrimidin-2-yl)-2-methylphenyl)-6-(trifluoromethyl)benzamide | (500 MHz) 10.37 (s, 1H), 9.21 (m, 1H), 8.72 (d, 1H), 8.38 (s, 1H), 8.06 (s, 1H), 7.76 (m, 4H), 7.38 (d, 1H), 2.30 (s, 3H) | 432.93 | and 2-fluoro-6-(trifluoromethyl)benzoic acid |

| Example (and FRF number) | Name | ¹H NMR (d₆-DMSO) | m/z [M + 1]⁺ | Starting materials |
|---|---|---|---|---|
| 23 FRF-02-176 | 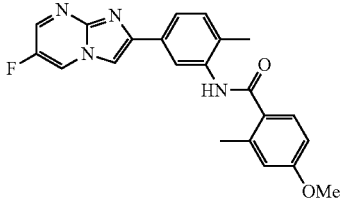 N-(5-(6-Fluoroimidazo[1,2-a]pyrimidin-2-yl)-2-methylphenyl)-4-methoxy-2-methylbenzamide | (500 MHz) 9.70 (s, 1H), 9.22 (m, 1H), 8.71 (d, 1H), 8.37 (s, 1H), 8.06 (s, 1H), 7.77 (m, 1H), 7.57 (d, 1H), 7.35 (d, 1H), 6.87 (m, 2H), 3.81 (s, 3H), 2.47 (s, 3H), 2.31 (s, 3H) | 391.05 | 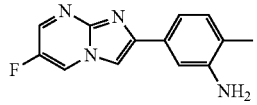 and 4-methoxy-2-methylbenzoic acid |
| 24 FRF-02-182 | 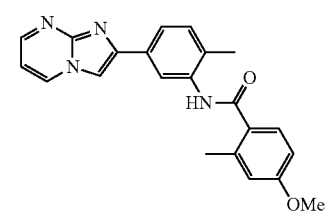 N-(5-(Imidazo[1,2-a]pyrimidin-2-yl)-2-methylphenyl)-4-methoxy-2-methylbenzamide | | 373.3 | 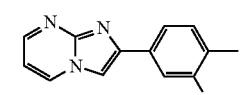 and 4-methoxy-2-methylbenzoic acid |
| 25 FRF-02-183 | 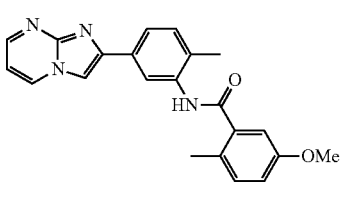 N-(5-(Imidazo[1,2-a]pyrimidin-2-yl)-2-methylphenyl)-5-methoxy-2-methylbenzamide | | 373.1 | 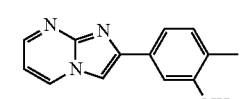 and 5-methoxy-2-methylbenzoic acid |
| 26 FRF-02-187 | 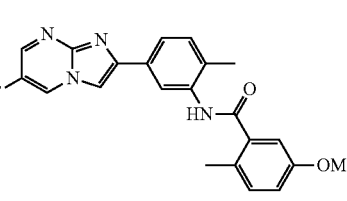 N-(5-(6-(Fluoroimidazo[1,2-a]pyrimidin-2-yl)-2-methylphenyl)-5-methoxy-2-methylbenzamide | (500 MHz) 9.84 (s, 1H), 9.23 (m, 1H), 8.71 (d, 1H), 8.38 (s, 1H), 8.08 (s, 1H), 7.79 (m, 1H), 7.36 (d, 1H), 7.23 (d, 1H), 7.13 (s, 1H), 6.98 (m, 1H), 3.81 (s, 3H), 2.39 (s, 3H), 2.32 (s, 3H) | 391.05 | 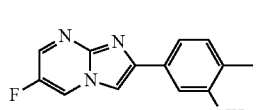 and 5-methoxy-2-methylbenzoic acid |
| 27 FRF-02-193 | 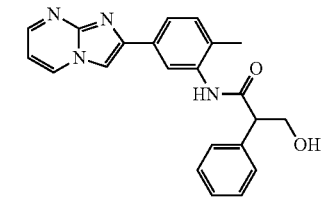 3-Hydroxy-N-(5-imidazo[1,2-a]pyrimidin-2-yl)-2-methylphenyl)-2-phenylpropanamide | | 373.4 | 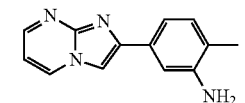 and 3-hydroxy-2-phenylpropanoic acid |

| Example (and FRF number) | Name | ¹H NMR (d₆-DMSO) | m/z [M + 1]⁺ | Starting materials |
|---|---|---|---|---|
| 28 FRF-02-194 | 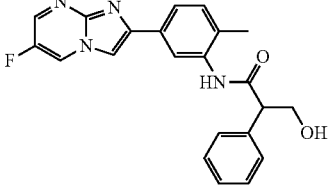<br>N-(5-(6-Fluoroimidazo[1,2-a]pyrimidin-2-yl)-2-methylphenyl)-3-hydroxy-2-phenylpropanamide | | 391.26 | 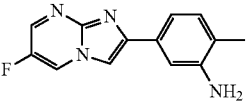<br>and 3-hydroxy-2-phenylpropanoic acid |
| 29 FRF-03-081 | 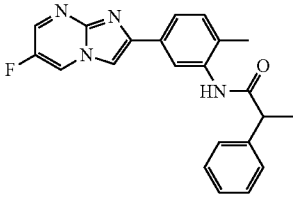<br>N-(5-(6-Fluoroimidazo[1,2-a]pyrimidin-2-yl)-2-methylphenyl)-2-phenylpropanamide | (500 MHz) 9.51 (s, 1H), 9.19 (m, 1H), 8.71 (d, 1H), 8.33 (s, 1H), 7.98 (s, 1H), 7.70 (m, 1H), 7.46 (m, 2H), 7.37 (m, 2H), 7.28 (m, 2H), 3.97 (q, 1H), 2.12 (s, 3H), 1.47 (d, 3H) | 375.1 | 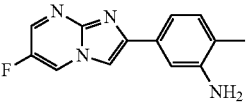<br>and 2-phenylpropanoic acid |
| 30 FRF-03-082 | 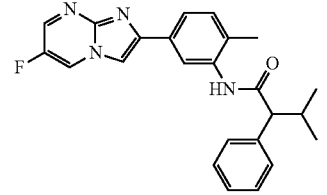<br>N-(5-(6-Fluoroimidazo[1,2-a]pyrimidin-2-yl)-2-methylphenyl)-3-methyl-2-phenylbutanamide | | 403.4 | 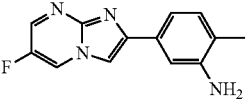<br>and 3-methyl-2-phenylbutanoic acid |
| 31 FRF-03-084-1 | 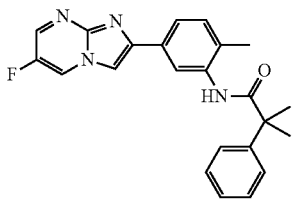<br>N-(5-(6-Fluoroimidazo[1,2-a]pyrimidin-2-yl)-2-methylphenyl)-2-methyl-2-phenylpropanamide | (500 MHz) 9.19 (m, 1H), 8.76 (s, 1H), 8.70 (d, 1H), 8.34 (s, 1H), 7.83 (s, 1H), 7.72 (d, 1H), 7.47 (m, 2H), 7.41 (m, 2H), 7.28 (m, 2H), 2.04 (s, 3H), 1.62 (s, 3H) | 389.2 | 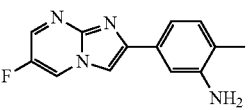<br>and 2-methyl-2-phenylpropanoic acid |

Biological Assays of the Compounds Described Herein

Example 1. Immunomodulatory Activity of Imidazopyrimidine Compounds

Human immunity is crucial to both health and illness, playing key roles in infectious, allergic, autoimmune, oncologic and chronic diseases. In this context there is growing interest in development of approaches to modulate the human immune system to prevent and/or treat illness. Infectious diseases are the leading cause of morbidity and mortality in early life. Immunization is a key strategy for preventing infectious diseases. However, immunization of newborns and infants may result in sub-optimal responses, often requires multiple booster doses and can be limited by waning immunity. Adjuvantation is a key approach to enhance vaccine-induced immunity. Adjuvants can enhance, prolong, and modulate immune responses to vaccinal antigens to maximize protective immunity, and may potentially enable effective immunization in vulnerable populations (e.g., in the very young and the elderly or for diseases lacking effective vaccines). Vaccine adjuvants also hold great potential as cancer immunotherapeutics. Small molecules that may be used as adjuvants have been reported. Utility in redirecting immune responses away from allergy (e.g., restoring a Th1/Th2 balance) has also been demonstrated for some molecules (e.g., as described in J Immunol Mar. 15, 1998, 160 (6) 2555-2559; and Adv Drug Deliv Rev. 2009 Mar. 28; 61(3):256-62, incorporated herein by reference).

Described herein is a novel molecular approach to shape human immune responses using formulations of imidazopyrimidine small molecules to induce robust activation of human leukocytes in vitro and as adjuvants in vivo. The parental compound identified to have the immune enhancing and adjuvant activity was named "Compound 037" as it was the 37$^{th}$ compound ordered into the Levy Lab (Boston Children's Hospital) for hit verification.

Figure 1B:
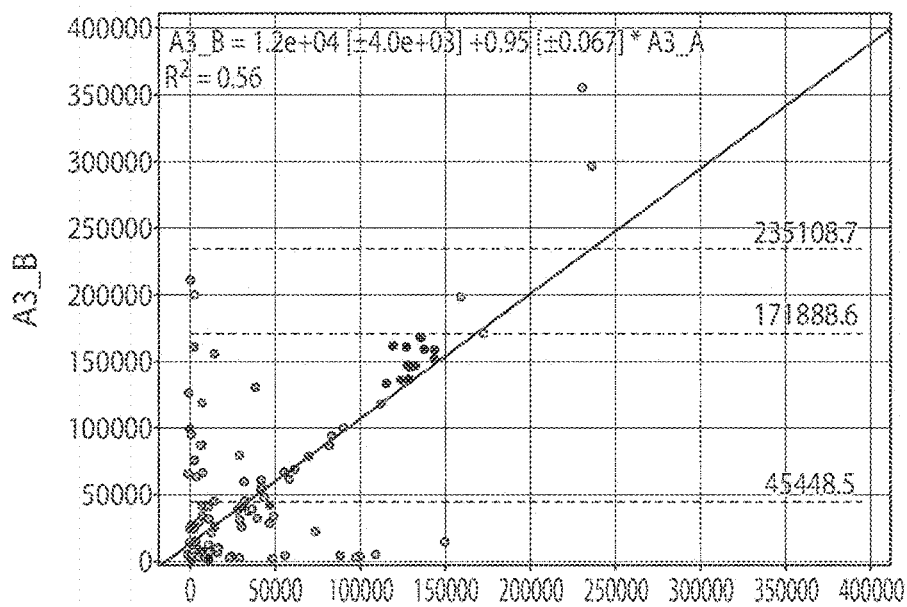
Figure 1C:
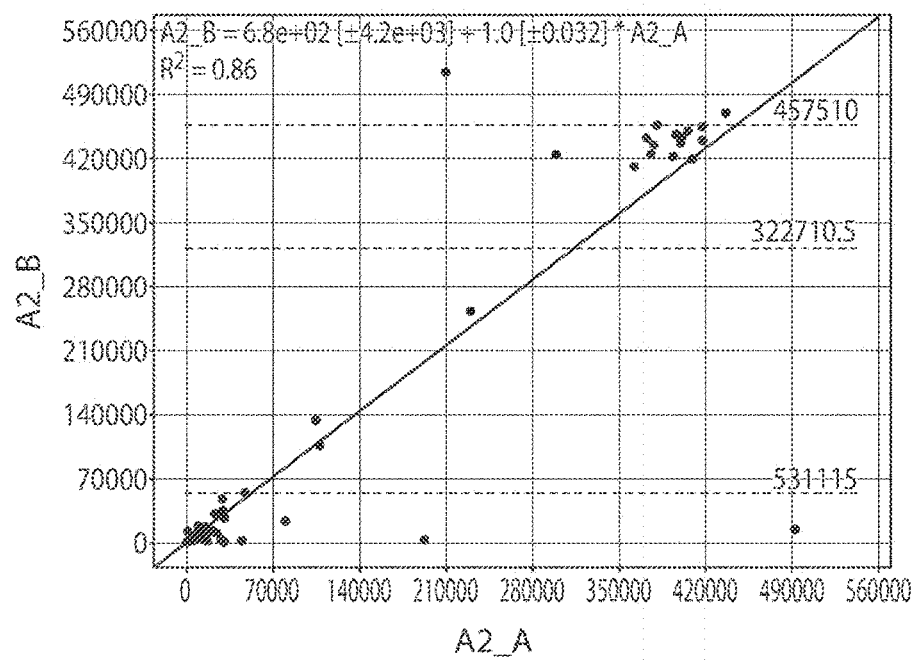

To identify immunomodulators/adjuvants that robustly activate human immune cells, ~200,000 small molecules were tested against THP1 NF-κB reporter cells in a screen. As there is evidence that cell culture lines such as THP1 cells may not model responses of natural primary human leukocytes, a smaller-scale novel high throughput screening methodology was also employed, in which ~9,000 commercially available compounds (focusing on small molecule library plates that had relatively high # of hits form the THP1 screen) were screened using primary human blood mononuclear cells (PBMC) from three different adult human donors (TNFαLISA Assay) (FIGS. 1A-1C).

TNF AlphaLISA screen was comprised of three parts: 1) human peripheral blood collection and PBMC isolation—human adult peripheral blood was collected with written consent. PBMCs were isolated from the blood using Ficoll density gradient. PBMCs were stored at 50 million cells per vial in 1 ml RPMI containing 20% autologous plasma and 10% DMSO at −80° C. until use; 2) TNFαLISA Assay—On Day 1, PBMCs were thawed in 37° C. water bath for 3 min and washed twice with PBS. Trypan blue viable cell count was obtained and cells were resuspended to viable 6.67×105 cells/ml in DMEM with 10% autologous plasma. Cells were dispensed in 30 μl per well in Corning 2712 black 384-well cell culture plates (final concentration was 20,000 cells/well). Controls were added to cells manually and the test compounds were added by robotic pin transfer. Plates were then incubated at 37° C./5% CO$_2$ humidity-controlled incubator for 18 hours. On Day 2 of the assay, plates were centrifuged and 2 μl supernatants were collected into Perkin Elmer Alpha plates. Perkin Elmer Human TNFα kits (cat #AL208F) were used to detect the presence of TNFα in supernatants. Plates were run on the EnVision instrument (Perkin Elmer) to detect light emission at 615 nm; 3) Hit Calling Method—test compounds that resulted in a robust Z score greater than 2 in both duplicates and of at least 2 of the 3 human samples of PBMCs were considered hits.

Based on antibody-coated fluorometric excitation/emission beads, the Alpha technology (PerkinElmer) enables the detection and screening of target molecules, in this case TNFα, in a no-wash, highly sensitive, quantitative assay compatible with high throughput screening.

The chemical libraries screened included known bioactive and commercial libraries from various sources including commercial libraries such as ChemDiv, ChemBridge, and Asinex (see attached pdf of all libraries). All libraries were owned and provided by the Institute of Chemistry and Cell Biology (ICCB)—Longwood (Harvard Medical School). Compound 037 was identified in the PBMC TNFαLISA screen.

Figure 1D:
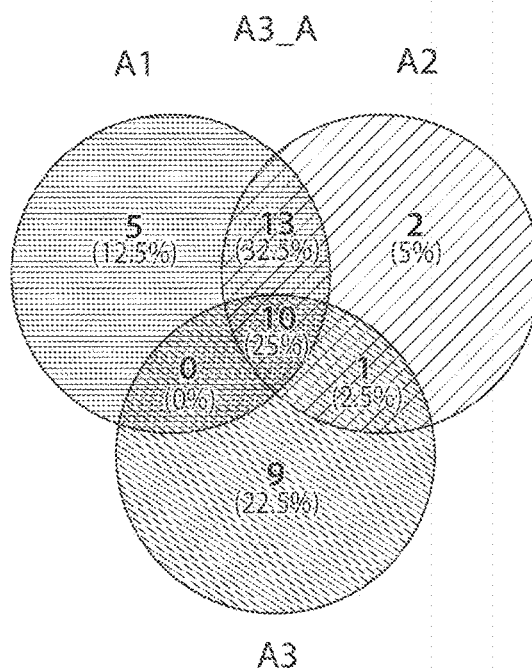
Figure 2A:
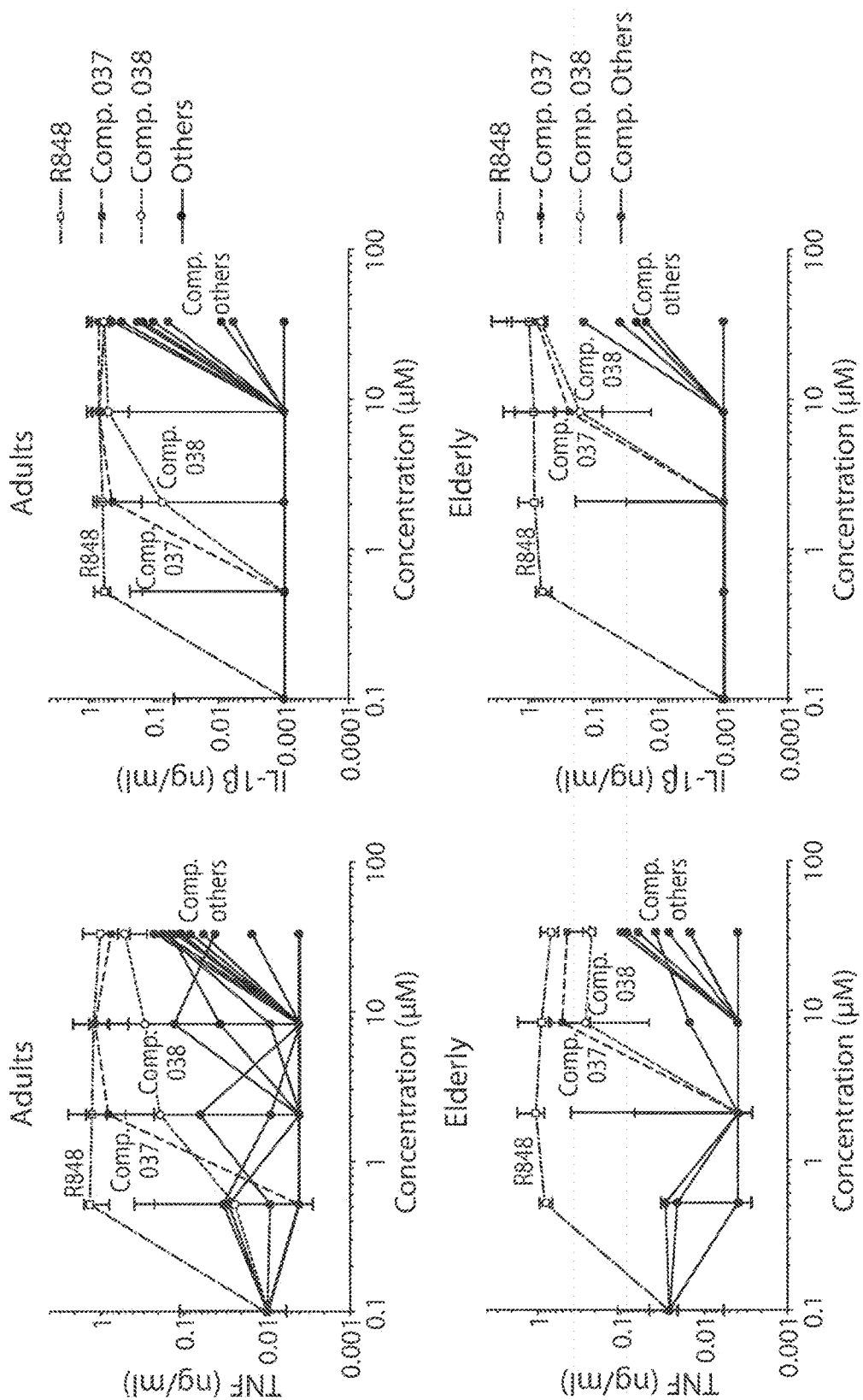
FIGS. 2A-2B demonstrate that compounds 037 and 038 induce TNF and IL-1β from adult and elderly PBMCs.
Figure 2B:
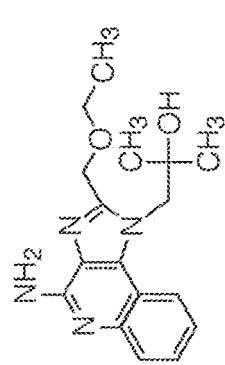
Figure 2B:
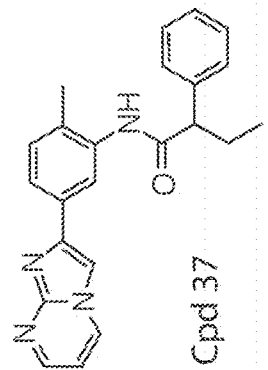
Figure 2B:
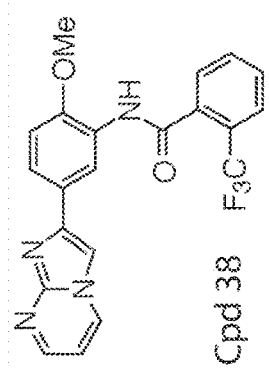
Figures 3A, 3B:
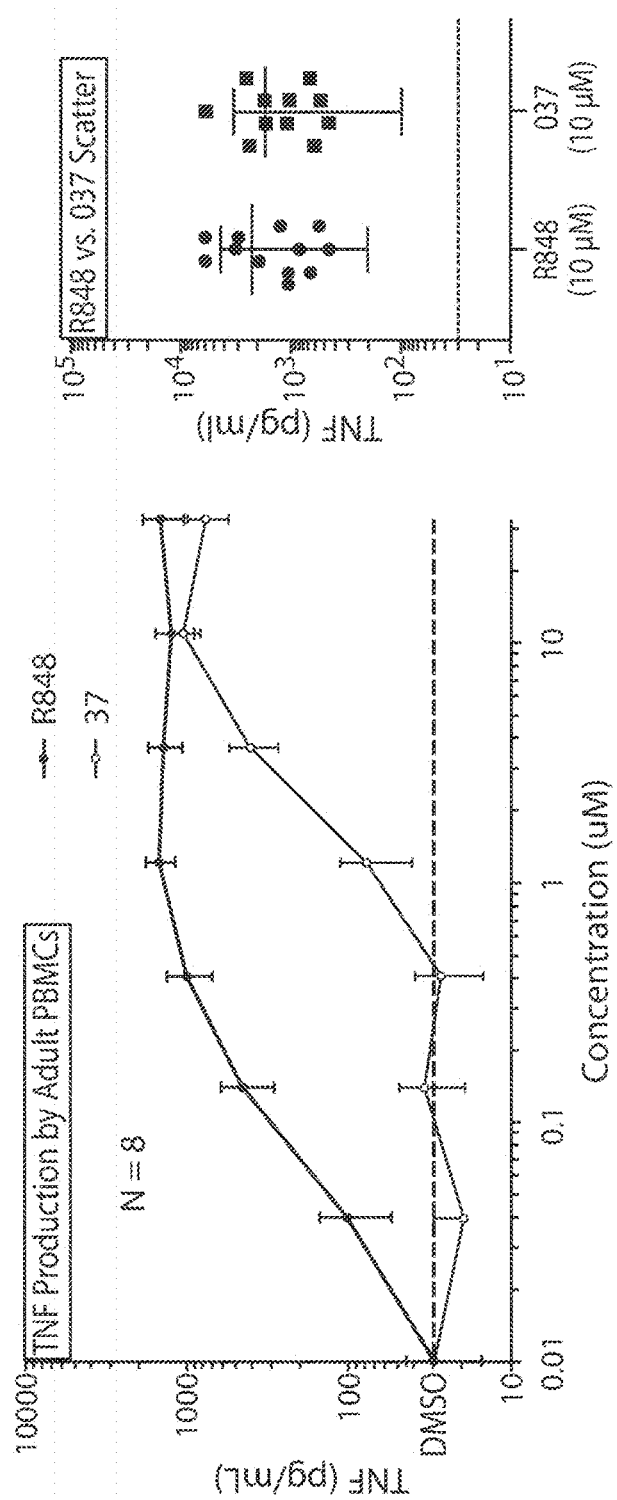
FIGS. 3A-3B depict the potency and efficacy of the 037 compound as compared to R848.
Figure 4:
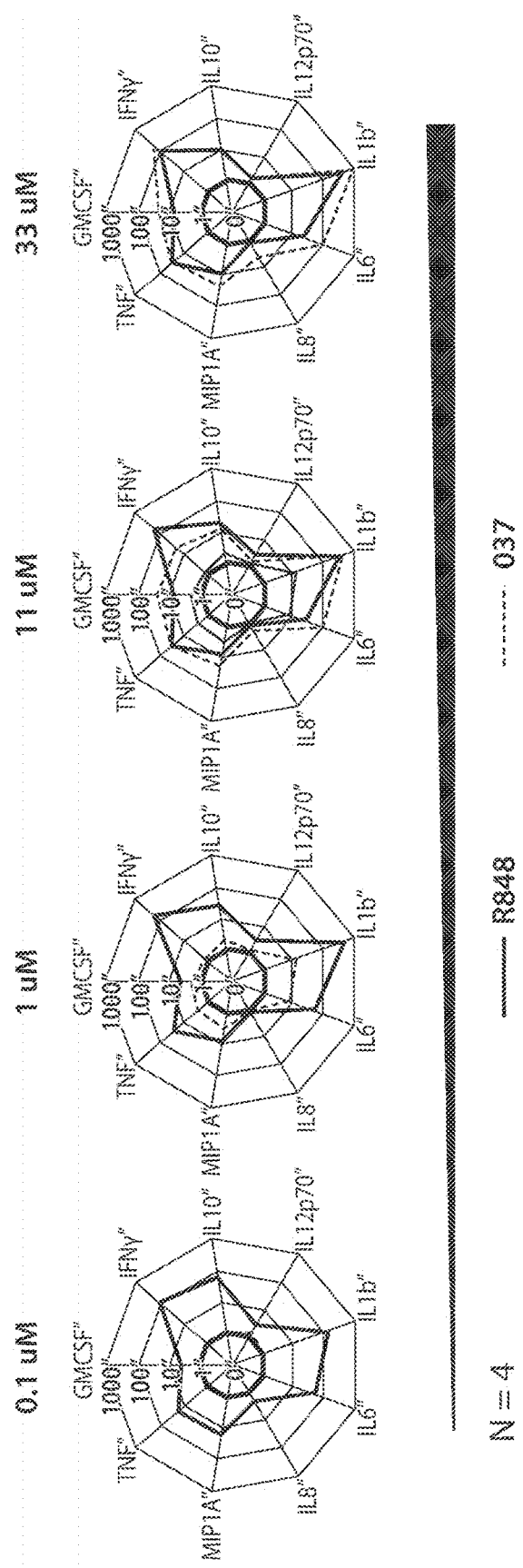
FIG. 4 are radar plots demonstrating that compound 037 induced a broad concentration-dependent cytokine response with distinct potency, efficacy and cytokine pattern as compared with R848. Shown is a 9-plex multiplex cytokine assay after stimulation of adult peripheral blood mononuclear cells (PBMCs) with compound 037 or R848 at four different concentrations (0.1 μM-33 μM). Radar plots of immune polarizing cytokine production from human adult PBMCs stimulated for 18 hours in 10% autologous plasma, represented as fold-change over RPMI unstimulated control (N=4).
Figure 5B:
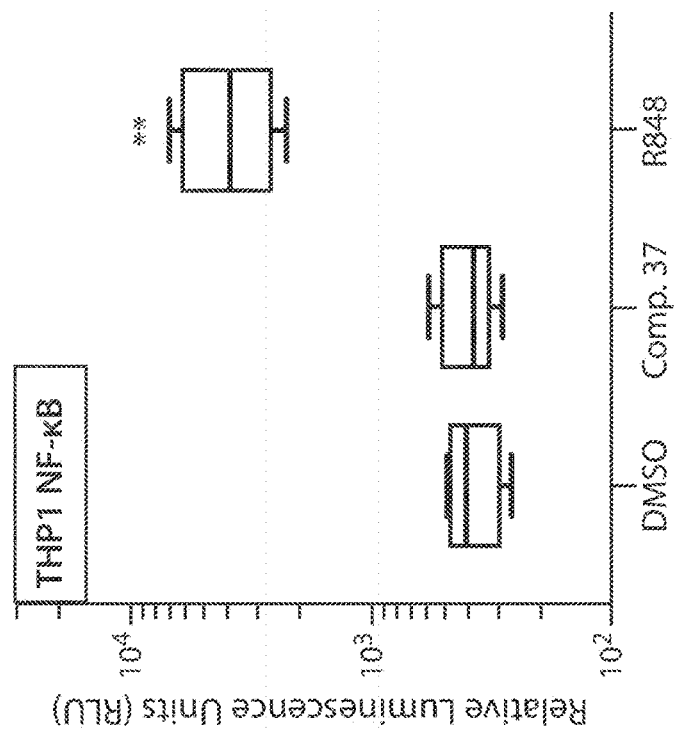
FIGS. 5A-5B demonstrate that while compound 037 induces robust production of TNF-α from human primary peripheral blood mononuclear cells, it demonstrates little activity towards THP1-Lucia cells via NF-κB-driven expression of luciferase.
Figure 5A:
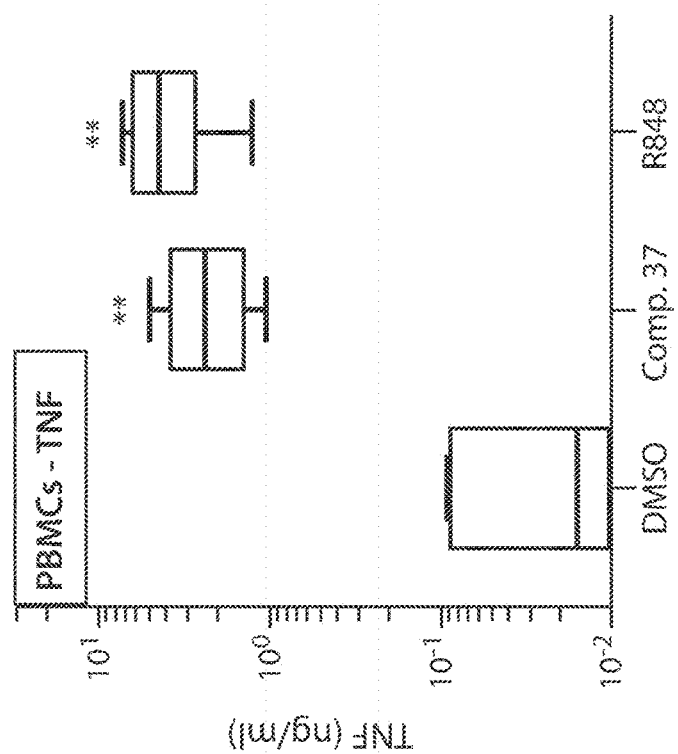

Hits were determined based on the ability of small molecules to induce TNF production in at least two of the three human adult donors screened (FIG. 1D). From this screen, the imidazopyrimidine compounds emerged as the chemical family with greatest potency in inducing robust TNF production in vitro (FIGS. 2A-2B). These results were confirmed in conventional human PBMC assays measuring cytokine production by ELISA as well as multiplexing assay for other Th-polarizing cytokines (IL-12p70, IL-6, IL-1β etc.) (FIGS. 3A, 3B, and 4). Of note, imidazopyrimidines did not activate the human THP1 cell line in any assay formatted tested, as demonstrated by the lack of activity towards the THP1 NF-κB reporter cell line (FIGS. 5A-5B).

Figure 8:
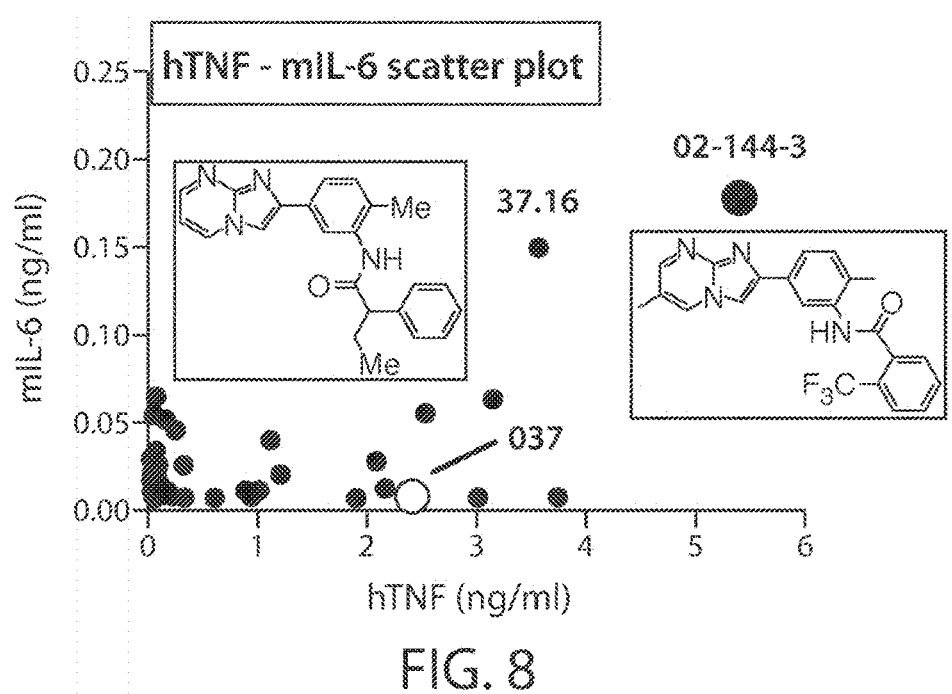
FIG. 8 demonstrates that the compound 037 analog 02-144-3 activates both human PBMCs and mouse splenocytes. Splenocytes isolated from 6-8 weeks old C57BL/6 mice and human adult PBMCs were stimulated for 18 hours with compound 037 and its analogs at 33 μM. Production of murine IL-6 and human TNF was assessed in cell-free supernatants by ELISA. Results are presented as scatter plot in which each dot represents median production of human TNF (N=3-5) or murine IL-6 (N=6) for each compound.
Figure 10:
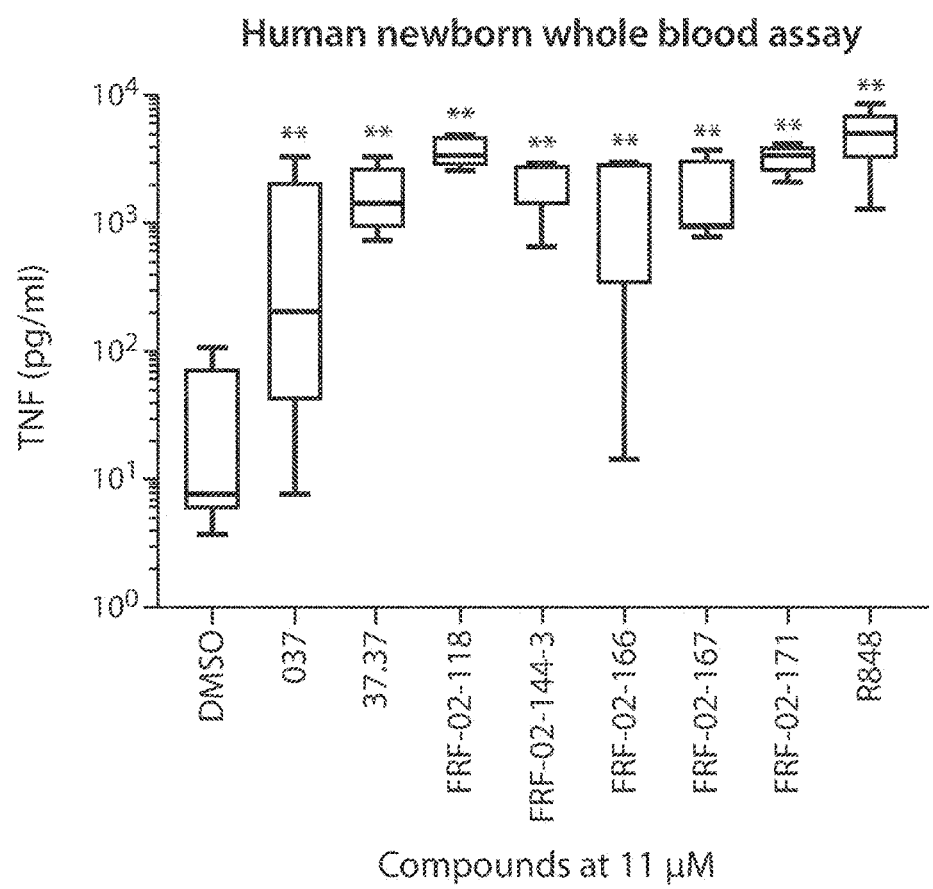
FIG. 10 demonstrates that imidazopyrimidines induce TNF production in a human newborn whole blood assay. Human newborn cord blood was anticoagulated with pyrogen-free heparin and stimulated with compound 037 analog family or R848 at 11 μM for 18 hours. After centrifugation, supernatants were collected and cryopreserved prior to measurement of TNF production by ELISA. N=5. **$p<0.01$ determined by repeated measure one-way ANOVA with Dunn's multiple comparison test on log-transformed data and comparing each compound with DMSO (control condition).

This great discrepancy in activity of the imidazopyrimidines between primary cells and THP1 cells is noteworthy, as for practical convenience many conventional high throughput screens employ cell lines such as THP-1 cells, highlighting the novelty and importance of the PBMC screening methodology in the identification of imidazopyrimidines as immune stimulating compounds. The ability of imidazopyrimidines to activate human newborn and elderly leukocytes as well as murine leukocytes was also confirmed in vitro (FIGS. 2A, 8, and 10), expanding potential utility of this compound family (e.g., to sub-populations at high risk for infection).

Figure 9:
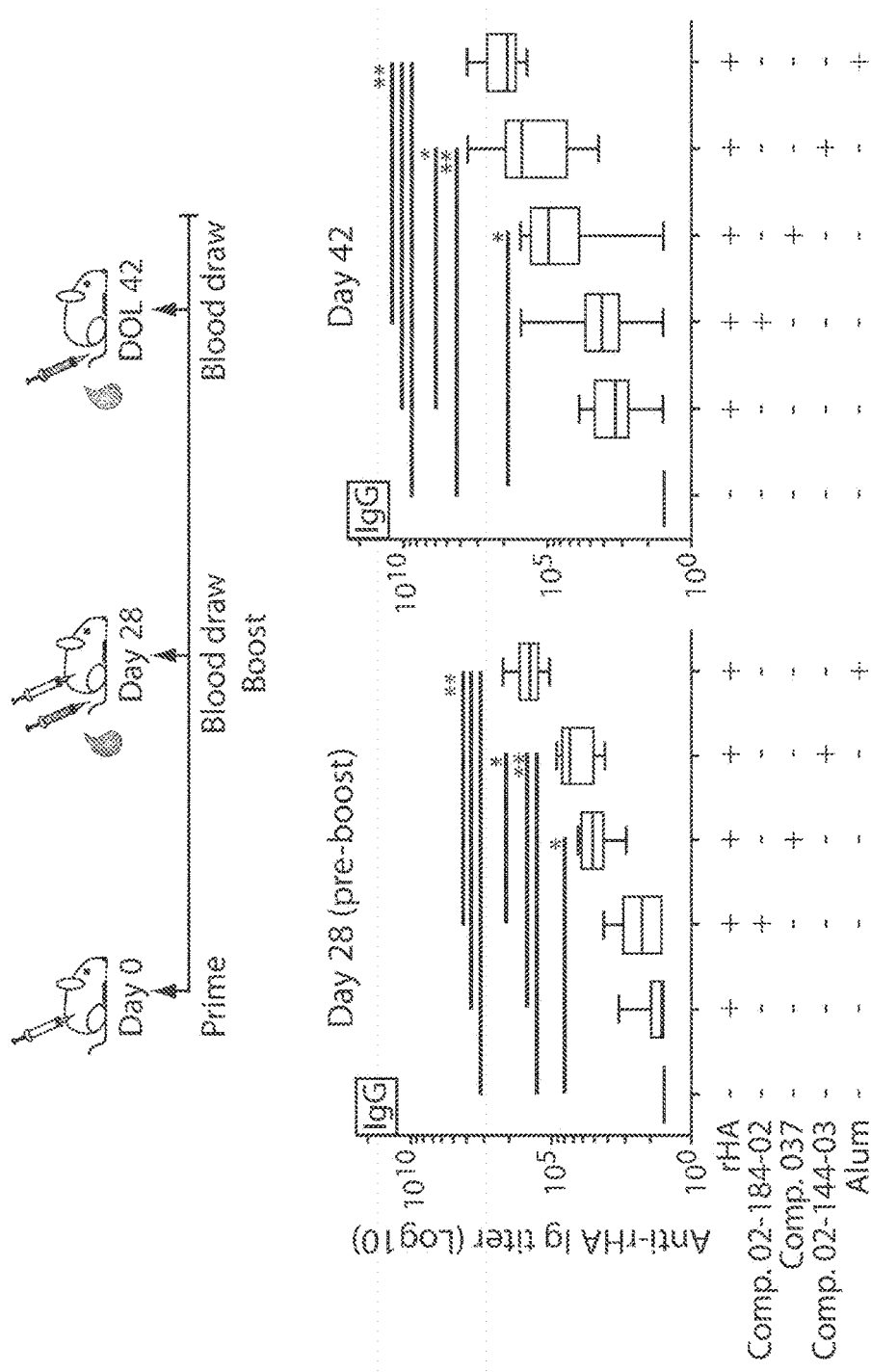
FIG. 9 shows correlation between in vitro and in vivo activities of compound 037 analogs. 6-8 weeks old C57BL/6 mice were immunized on Day 0 (prime) and Day 28 (boost) with rHA alone or formulated with compound 02-184-02 (inactive analog), compound 037, compound 02-144-3 (analog that was active on both human and murine cells) or alum. Serum samples were collected at Day 28 (pre-boost) and Day 42 (14 post-boost) and anti-rHA IgG titers were measured by ELISA. Results are shown as the median, the 25th and 75th percentiles (boxes) and the 5th and 95th percentiles (whiskers) of 10 mice per group. *$p<0.05$ and **$p<0.01$ determined by Kruskal-Wallis with Dunn's multiple comparison test.

Additionally, in vivo studies in a murine model of influenza immunization indicate that the addition of imidazopyrimidines markedly enhances vaccine responses of adult mice (FIG. 9). Mice vaccinated with recombinant Influenza Hemagglutinin (rHA)+imidazopyrimidines demonstrated higher antibody titers compared to mice vaccinated with rHA alone and equivalent or enhanced titers as compared to mice vaccinated with rHA+Alum, the most commonly used vaccine adjuvant.

Figures 6A, 6B:
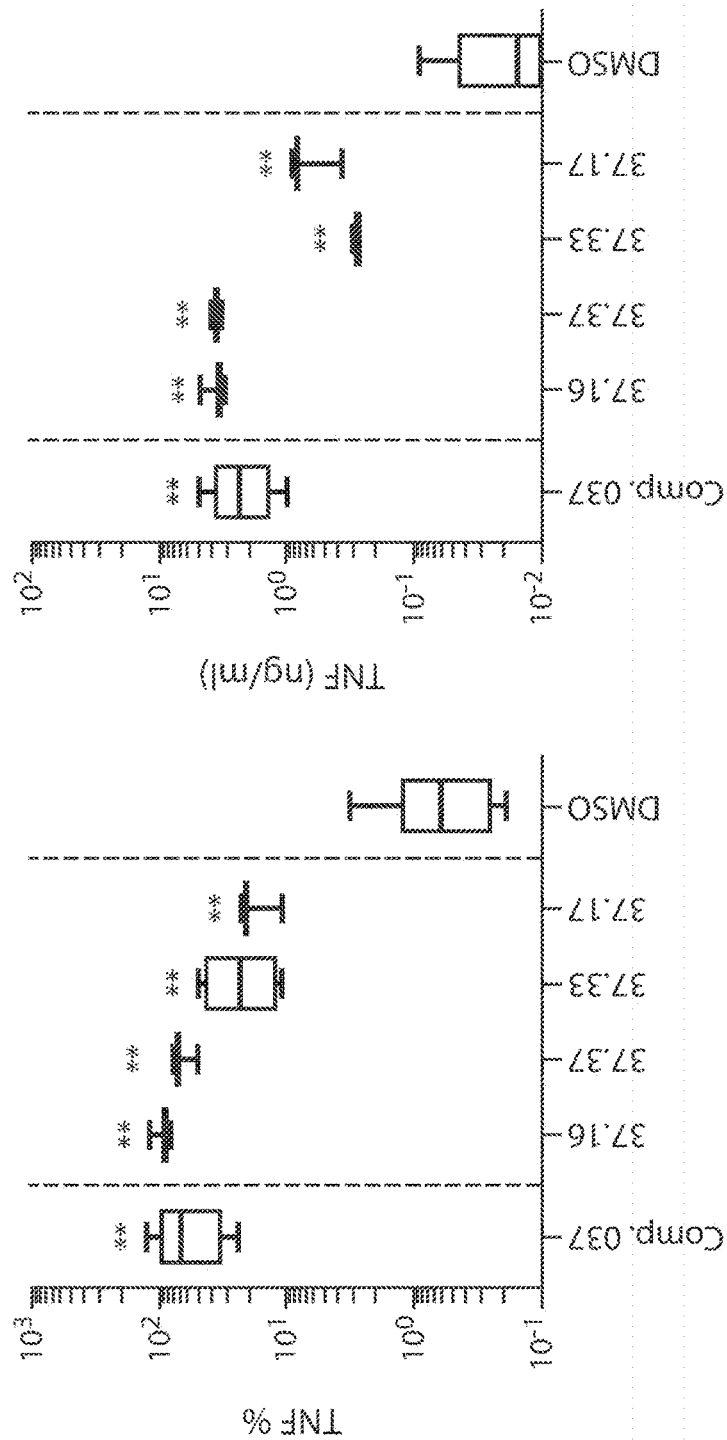
FIGS. 6A-6B shows the activity of compound 037 and commercially available compound 037 analogs (imidazopyrimidines) on human adult PBMCs. Human adult PBMCs were stimulated for 18 hours with compound 037 and its analogs at 33 μM. Production of human TNF was assessed in cell-free supernatants by ELISA. Results are shown as the median, the 25th and 75th percentiles (boxes) and the 5th and 95th percentiles (whiskers) and expressed as percentage TNF production (TNF %) as compared to R848 (FIG. 6A) or TNF concentration in ng/ml (FIG. 6B) (N=3-5). **$p<0.01$ determined by repeated measure one-way ANOVA with Dunnett's multiple comparison test on log-transformed data and comparing each compound with DMSO (control condition).
Figure 7A:
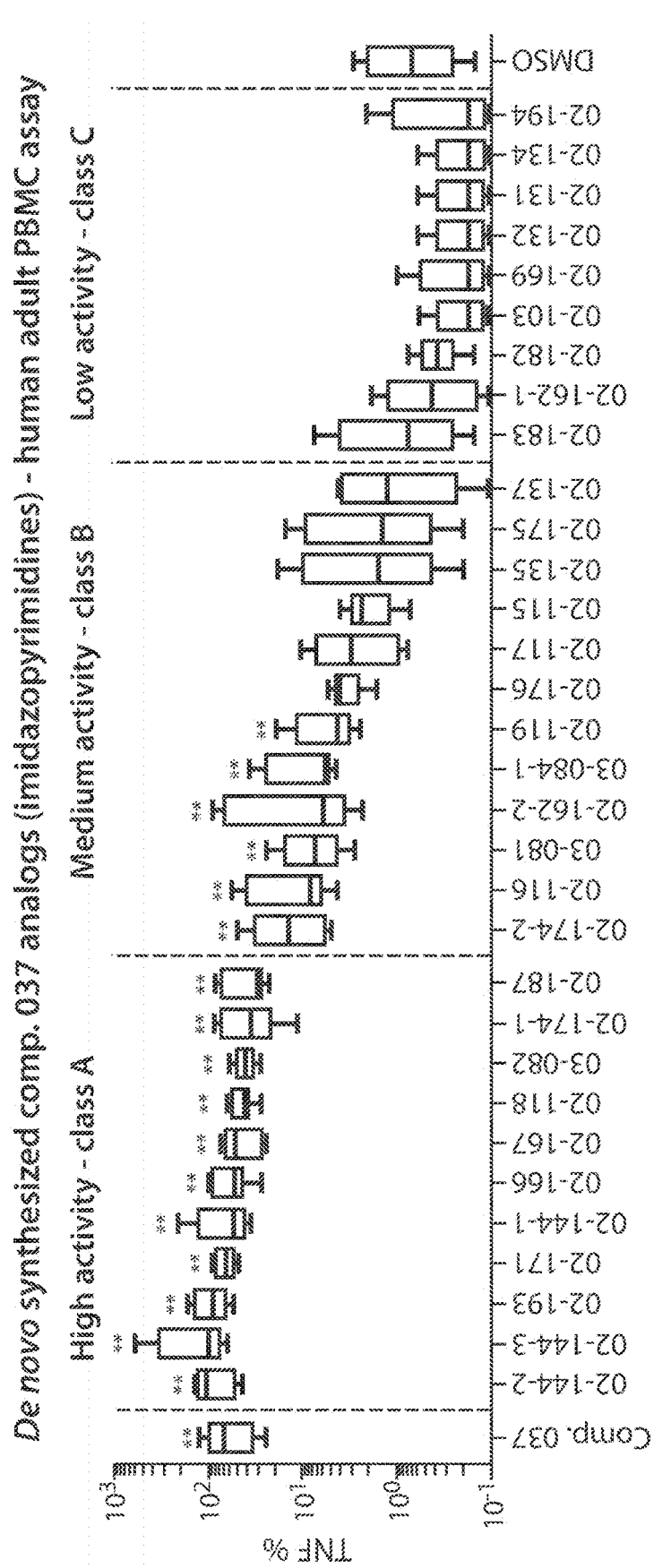
FIGS. 7A-7B shows the activity of compound 037 and de novo synthesized compound 037 analogs (imidazopyrimidines) on human adult PBMCs. Human adult PBMCs were stimulated for 18 hours with compound 037 and its analogs at 33 μM. Production of human TNF was assessed in cell-free supernatants by ELISA. Results are shown as the median, the 25th and 75th percentiles (boxes) and the 5th and 95th percentiles (whiskers) and expressed as percentage TNF production (TNF %) as compared to R848 (FIG. 7A) or TNF concentration in ng/ml (FIG. 7B) (N=5). Analogs are ranked left to right by TNF % (compound 037 on the far left). Compound 037 analogs have been classified in the following categories according to TNF %: high activity—class A: TNF %>15%; medium activity—class B: 1%<TNF %≤15%; low activity—class C: TNF %≤1%. **$p<0.01$ determined by repeated measure one-way ANOVA with Dunnett's multiple comparison test on log-transformed data and comparing each compound with DMSO (control condition).
Figure 7B:
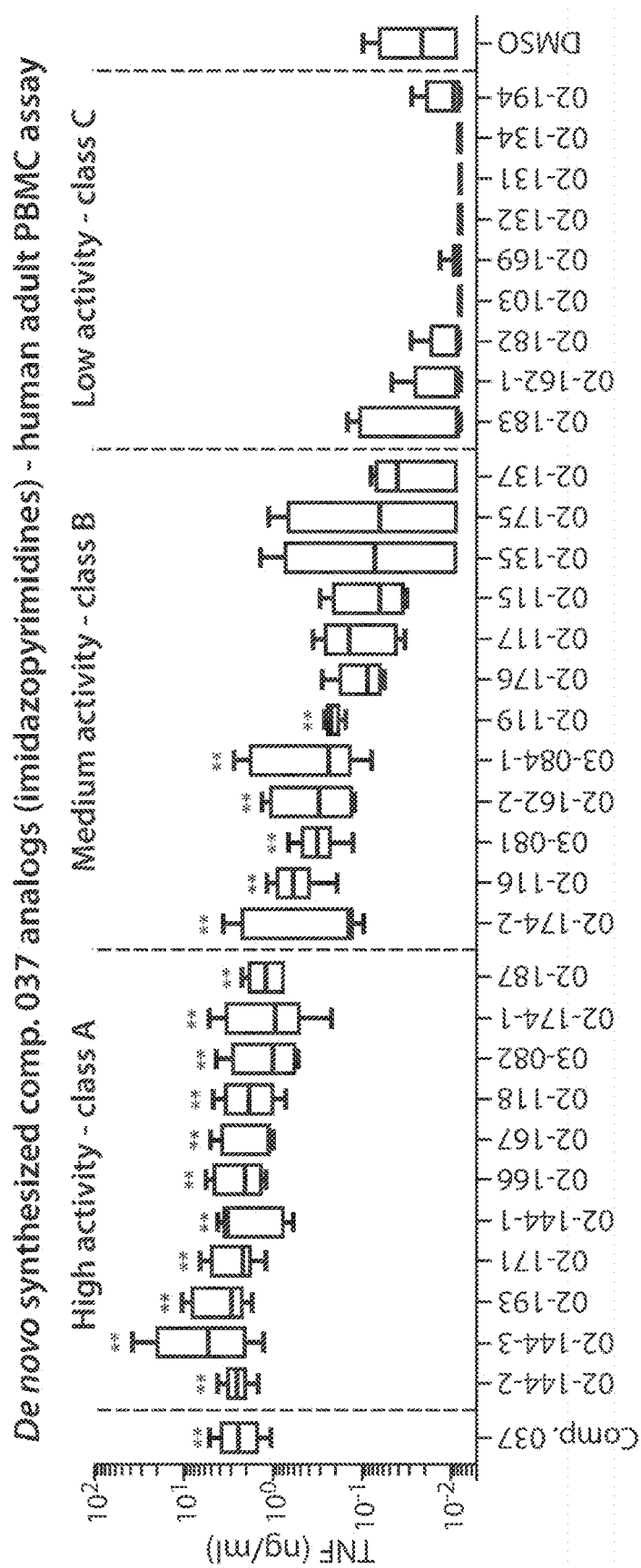

Additional commercially available analogs of compound 037 were profiled in the PBMC assay (FIGS. 6A, 6B, and Table 1) with R848 as a positive control, to generate some initial structure activity relationships (SAR) within the imidazopyrimidine series. Certain structural features appeared important for activity, and a further set of imidazopyrimidines was prepared and tested, with some examples showing equivalent or superior activity to both compound 037 and R848 in this assay (e.g. FIGS. 7A and 7B and Table 1).

In summary, imidazopyrimidine compounds have activity as immunomodulators/adjuvants, activating human leukocytes in vitro and demonstrating adjuvanticity in mice in vivo.

The imidazopyrimidine compounds described herein may be used as stand alone agents to modify human immune responses, e.g., to be applied topically to treat infections by enhancing an immune response; given orally to enhance mucosal immunity or intranasally to treat respiratory infection or to reduce allergy (e.g., allergic rhinitis); injected locally or systemically to enhance immune responses against tumors and cancers. The compounds may also be given prophylactically to induce heightened immunity for broad protection against infection or radiation injury in high risk populations. The adjunctive therapy may also be coupled with other treatments for the conditions described herein. Further, the compounds may be used as vaccine adjuvant to be formulated with vaccinal antigen to enhance, accelerate, and/or broaden immune responses and/or to reduce the number of doses required ("dose sparing"), which is very important given the costs of vaccinal antigens and challenges of multiple clinic visits when vaccine boosting is required to achieve protective immune responses.

The imidazopyrimidine compounds, compositions, and methods described herein are advantageous for the following, but are not limited to, reasons:

(1) Small molecule category amenable to affordable scale up for mass production/use;
(2) Molecular scaffold of the compounds appears to be relatively favorable from a medicinal chemistry perspective for production and creation of congeners/analogues;
(3) The compounds are active towards human cells including those at the extremes of age—e.g., newborns and the elderly; and
(4) The compounds induce a distinct pattern of cytokines relative to other established small molecule adjuvants (e.g., different from R848), suggesting distinct activity.

Table 1. Activity of Exemplary Imidazopyrimidine Compounds on Stimulating TNF Production in PBMCs as Compared to Compound R848

Table 1 provides the activity of exemplary compounds on stimulating TNF production in PBMCs as compared to the benchmark compound R848. Specifically, TNF production was measured by ELISA after stimulation of adult PBMCs with compound 037 analog family or the compound R848 at 33 µM for 18 hours. Analogs are ranked top to bottom by median percentage TNF production (TNF %) as compared to R848 (N=3-5). The compounds have been classified in the following categories according to TNF %: high activity—class A: TNF %>15%; medium activity—class B: 1%<TNF %≤15%; low activity—class C: TNF %≤1%.

TABLE 1

Activity of Exemplary Imidazopyrimidine Compounds on Stimulating TFN Production in PBMCs as compared to Compound R848

| Compound ID | TNF (Median) | TNF % (Median) | Activity class | # replicates | Series | Molecular weight | Compound Structure |
|---|---|---|---|---|---|---|---|
| FRF-02-144-2 | 2.5245 | 104.32 | A | 5 | 6-Me Imidazopyrimidine | 376.84 | 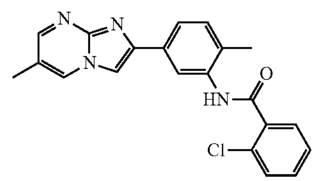 |
| FRF-02-144-3 | 5.397 | 99.81 | A | 5 | 6-Me Imidazopyrimidine | 410.40 | 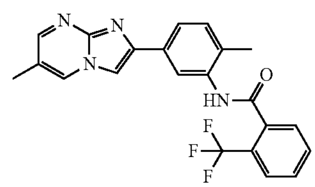 [SMILES: Cc1cnc2nc(-c3ccc(C)c(NC(=O)c4ccccc4C(F)(F)F)c3)cn2c1] |
| FRF-02-193 | 2.997 | 91.73 | A | 5 | Imidazopyrimidine | 372.43 | 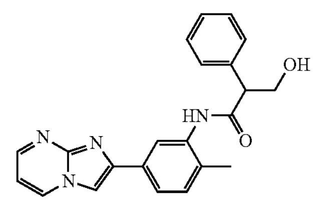 [SMILES: Cc1ccc(-c2cn3cccnc3n2)cc1NC(=O)C(CO)c1ccccc1] |
| 37.16 | 3.5625 | 90.17 | A | 3 | Imidazopyrimidine | 407.27 | 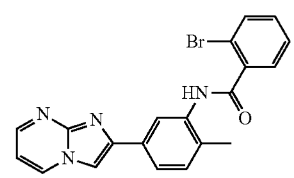 [SMILES: Cc1ccc(-c2cn3cccnc3n2)cc1NC(=O)c1ccccc1Br] |
| 37.37 | 3.73 | 71.12 | A | 3 | Imidazopyrimidine | 396.37 | 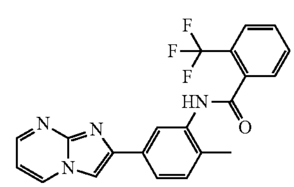 [SMILES: Cc1ccc(-c2cn3cccnc3n2)cc1NC(=O)c1ccccc1C(F)(F)F] |
| Compound 37 | 2.403 | 69.79 | A | 5 | Imidazopyrimidine | 370.46 | 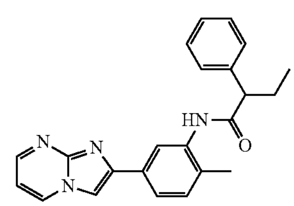 [SMILES: CCC(C(=O)Nc1cc(-c2cn3cccnc3n2)ccc1C)c1ccccc1] |

TABLE 1-continued

*Activity of Exemplary Imidazopyrimidine Compounds on Stimulating TFN Production in PBMCs as compared to Compound R848*

| Compound ID | TNF (Median) | TNF % (Median) | Activity class | # replicates | Series | Molecular weight | Compound Structure |
|---|---|---|---|---|---|---|---|
| FRF-02-171 | 2.1615 | 65.93 | A | 5 | 6-F Imidazo-pyrimidine | 428.39 | 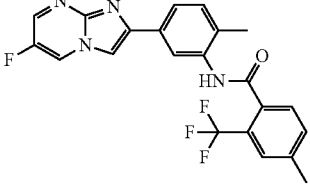 |
| FRF-02-144-1 | 3.144 | 55.24 | A | 5 | 6-Me Imidazo-pyrimidine | 384.48 | 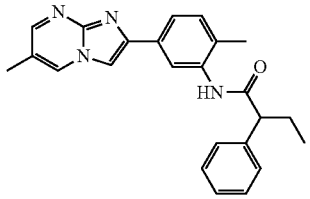 [SMILES: CCC(C(=O)Nc1cc(-c2cn3cc(C)cnc3n2)ccc1C)c1ccccc1] |
| FRF-02-166 | 2.0745 | 53.91 | A | 5 | 6-F Imidazo-pyrimidine | 432.35 | 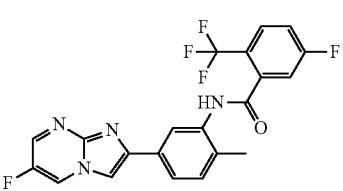 [SMILES: Cc1ccc(-c2cn3cc(F)cnc3n2)cc1NC(=O)c1cc(F)ccc1C(F)(F)F] |
| FRF-02-167 | 1.101 | 51.62 | A | 5 | 6-F Imidazo-pyrimidine | 432.35 | 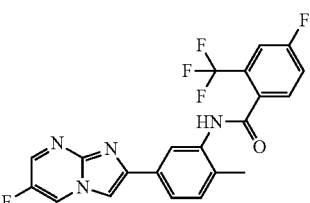 |
| FRF-02-118 | 1.8795 | 43.53 | A | 5 | 6-F Imidazo-pyrimidin | 414.36 | 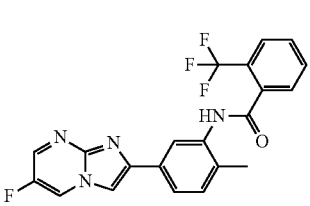 [SMILES: Cc1ccc(-c2cn3cc(F)cnc3n2)cc1NC(=O)c1ccccc1C(F)(F)F] |
| FRF-03-082 | 1.008 | 41.65 | A | 5 | 6-F Imidazo-pyrimidine | | 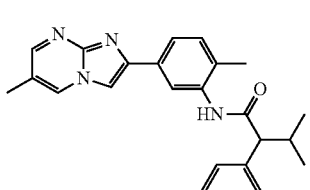 |
| FRF-02-174-1 | 0.924 | 35.71 | A | 5 | 6-Me Imidazo-pyrimidine | 404.90 | 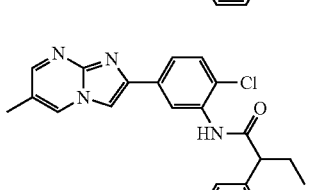 |

TABLE 1-continued

Activity of Exemplary Imidazopyrimidine Compounds on Stimulating TFN Production in PBMCs as compared to Compound R848

| Compound ID | TNF (Median) | TNF % (Median) | Activity class | # replicates | Series | Molecular weight | Compound Structure |
|---|---|---|---|---|---|---|---|
| FRF-02-187 | 1.191 | 31.32 | A | 5 | 6-F Imidazo-pyrimidine | 390.42 | 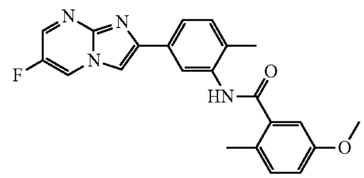 [SMILES: COc1ccc(C)c(C(=O)Nc2cc(-c3cn4cc(F)cnc4n3)ccc2C)c1] |
| 37.33 | 0.288 | 22.94 | A | 4 | Imidazo-pyrimidine | 362.82 | 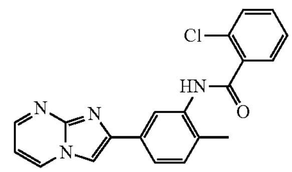 [SMILES: Cc1ccc(-c2cn3cccnc3n2)cc1NC(=O)c1ccccc1Cl] |
| 37.17 | 0.865 | 20.64 | A | 3 | Imidazo-pyrimidine | 342.40 | 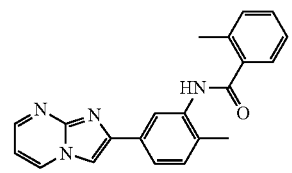 [SMILES: Cc1ccc(-c2cn3cccnc3n2)cc1NC(=O)c1ccccc1C] |
| FRF-02-174-2 | 0.1455 | 13.99 | B | 5 | 6-Me Imidazo-pyrimidine | 430.82 | 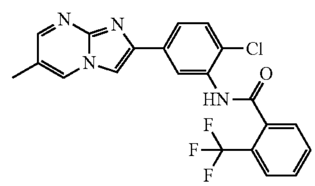 [SMILES: Cc1cnc2nc(-c3ccc(Cl)c(NC(=O)c4ccccc4C(F)(F)F)c3)cn2c1] |
| FRF-02-116 | 0.594 | 8.48 | B | 5 | 6-F Imidazo-pyrimidine | 425.26 | 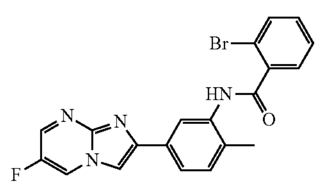 [SMILES: Cc1ccc(-c2cn3cc(F)cnc3n2)cc1NC(=O)c1ccccc1Br] |
| FRF-03-081 | 0.3195 | 7.51 | B | 5 | 6-F Imidazo-pyrimidine | | 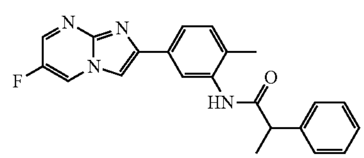 [SMILES: Cc1ccc(-c2cn3cc(F)cnc3n2)cc1NC(=O)C(C)c1ccccc1] |
| FRF-02-162-2 | 0.309 | 6.34 | B | 5 | 6-Me Imidazo-pyrimidine | 356.43 | 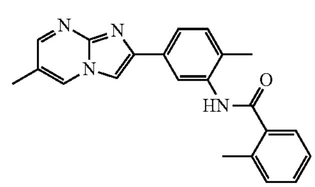 [SMILES: Cc1cnc2nc(-c3ccc(C)c(NC(=O)c4ccccc4C)c3)cn2c1] |
| FRF-03-084-1 | 0.24 | 6.00 | B | 5 | 6-F Imidazo-pyrimidine | | 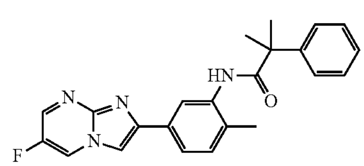 [SMILES: Cc1ccc(-c2cn3cc(F)cnc3n2)cc1NC(=O)C(C)(C)c1ccccc1] |

TABLE 1-continued

Activity of Exemplary Imidazopyrimidine Compounds on Stimulating TFN
Production in PBMCs as compared to Compound R848

| Compound ID | TNF (Median) | TNF % (Median) | Activity class | # replicates | Series | Molecular weight | Compound Structure |
|---|---|---|---|---|---|---|---|
| FRF-02-119 | 0.219 | 4.35 | B | 5 | 6-F Imidazo-pyrimidine | 388.45 | 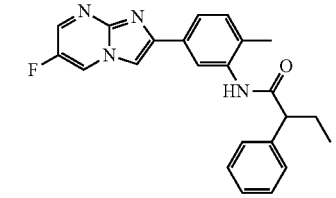 [SMILES: CCC(C(=O)Nc1cc(-c2cn3cc(F)cnc3n2)ccc1C)c1ccccc1] |
| FRF-02-176 | 0.087 | 3.81 | B | 5 | 6-F Imidazo-pyrimidine | 390.42 | 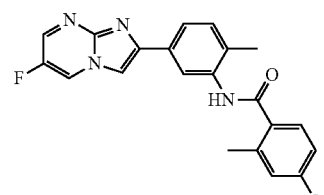 |
| FRF-02-117 | 0.138 | 3.06 | B | 5 | 6-F Imidazo-pyrimidine | 360.39 | 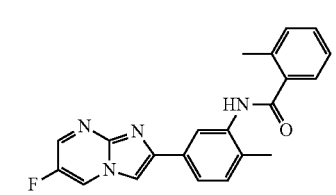 [SMILES: Cc1ccc(-c2cn3cc(F)cnc3n2)cc1NC(=O)c1ccccc1C] |
| FRF-02-115 | 0.0625 | 2.42 | B | 5 | 6-F Imidazo-pyrimidine | 380.81 | 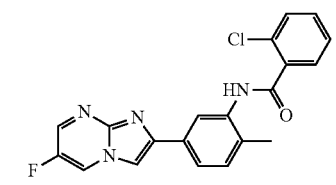 |
| FRF-02-135 | 0.0705 | 1.60 | B | 5 | 6-MeO Imidazo-pyrimidine | 426.40 | 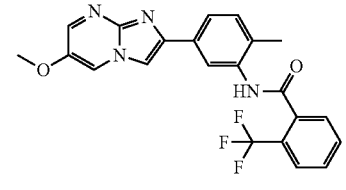 [SMILES: COc1cnc2nc(-c3ccc(C)c(NC(=O)c4ccccc4C(F)(F)F)c3)cn2c1] |
| FRF-02-175 | 0.063 | 1.43 | B | 5 | 6-F Imidazo-pyrimidine | 432.35 | 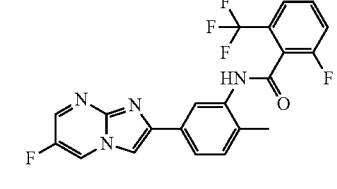 |
| FRF-02-137 | 0.04 | 1.27 | B | 5 | 6-MeO Imidazo-pyrimidine | 400.48 | 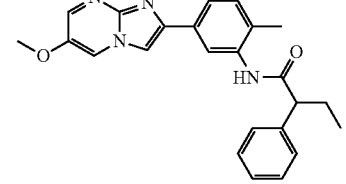 |

TABLE 1-continued

Activity of Exemplary Imidazopyrimidine Compounds on Stimulating TFN Production in PBMCs as compared to Compound R848

| Compound ID | TNF (Median) | TNF % (Median) | Activity class | # replicates | Series | Molecular weight | Compound Structure |
|---|---|---|---|---|---|---|---|
| FRF-02-183 | 0.008 | 0.77 | C | 5 | Imidazo-pyrimidine | 372.43 | 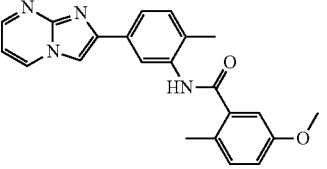 [SMILES: COc1ccc(C)c(C(=O)Nc2cc(-c3cn4cccnc4n3)ccc2C)c1] |
| FRF-02-162-1 | 0.008 | 0.42 | C | 5 | 6-Me Imidazo-pyrimidine | 356.43 | 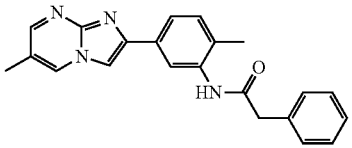 [SMILES: Cc1cnc2nc(-c3ccc(C)c(NC(=O)Cc4ccccc4)c3)cn2c1] |
| FRF-02-182 | 0.008 | 0.39 | C | 5 | Imidazo-pyrimidine | 372.43 | 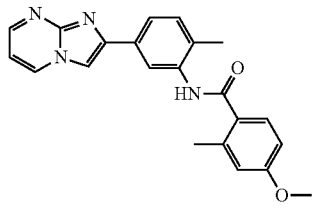 [SMILES: COc1ccc(C(=O)Nc2cc(-c3cn4cccnc4n3)ccc2C)c(C)c1] |
| FRF-02-103 | 0.008 | 0.18 | C | 5 | Imidazo-pyrimidine | 342.40 | 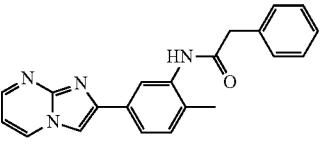 [SMILES: Cc1ccc(-c2cn3cccnc3n2)cc1NC(=O)Cc1ccccc1] |
| FRF-02-169 | 0.008 | 0.18 | C | 5 | 6-F Imidazo-pyrimidine | 448.81 | 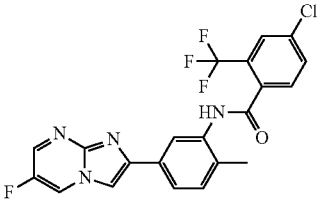 [SMILES: Cc1ccc(-c2cn3cc(F)cnc3n2)cc1NC(=O)c1ccc(Cl)cc1C(F)(F)F] |
| FRF-02-132 | 0.008 | 0.18 | C | 5 | 6-MeO Imidazo-pyrimidine | 437.30 | 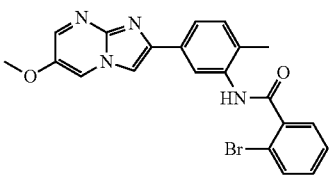 [SMILES: COc1cnc2nc(-c3ccc(C)c(NC(=O)c4ccccc4Br)c3)cn2c1] |
| FRF-02-131 | 0.008 | 0.18 | C | 5 | 6-MeO Imidazo-pyrimidine | 392.84 | 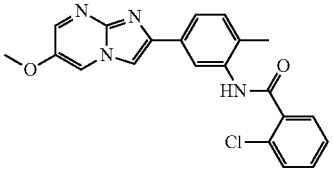 [SMILES: COc1cnc2nc(-c3ccc(C)c(NC(=O)c4ccccc4Cl)c3)cn2c1] |
| FRF-02-134 | 0.008 | 0.18 | C | 5 | 6-MeO Imidazo-pyrimidine | 372.43 | 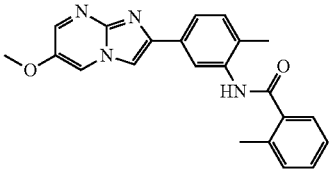 [SMILES: COc1cnc2nc(-c3ccc(C)c(NC(=O)c4ccccc4C)c3)cn2c1] |

TABLE 1-continued

Activity of Exemplary Imidazopyrimidine Compounds on Stimulating TFN Production in PBMCs as compared to Compound R848

| Compound ID | TNF (Median) | TNF % (Median) | Activity class | # replicates | Series | Molecular weight | Compound Structure |
|---|---|---|---|---|---|---|---|
| FRF-02-194 | 0.008 | 0.18 | C | 5 | 6-F Imidazopyrimidine | 390.42 | 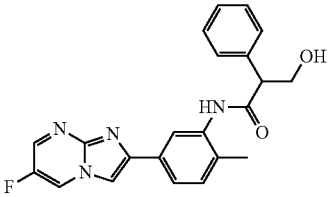 [SMILES: Cc1ccc(-c2cn3cc(F)cnc3n2)cc1NC(=O)C(CO)c1ccccc1] |

Materials and Methods

Overview. To identify immunomodulators/adjuvants that robustly activate human immune cells, screening of ~200,000 small molecules tested against THP1 cells was conducted. As there is evidence that cell culture lines such as THP-1 cells may not model responses of natural primary human leukocytes, also employed was a smaller-scale novel high throughput screening methodology in which ~9,000 commercially available compounds were screened, focusing on small molecule library plates that had relatively high # of hits form the THP-1 screen, using primary human blood mononuclear cells from three different adult human donors and a TNFαLISA Assay (commercially purchased from PerkinElmer). See Schildberger et al., *Mediators of Inflammation*, Volume 2013, Article ID 697972 (2013).

THP-1 Cell Line and Culture Conditions. The THP1-Lucia™ cell line was obtained from Invivogen (San Diego, Calif.). THP1-Lucia cells, which are human monocytic cells derived from the blood of a boy with leukemia, contain an NF-kB-inducible Luc reporter construct. This allows NF-kB activation to be measured by quantifying the luminescence from the secreted luciferase enzyme. THP1-Lucia cells were cultured in RPMI 1640 supplemented with 10% non-heat inactivated fetal bovine serum (FBS), 10 mM HEPES, 1.0 mM sodium pyruvate, 50 ug/ml Pen-Strep, and 100 ug/mL Normocin™. Once cultured, the cells were stored in a 37° C. incubator with 5% $CO_2$ and a humidified atmosphere. Cells were passaged every 2-3 days and not allowed to exceed a concentration of $2.0 \times 10^6$ cells/ml media.

Chemical Libraries. The chemical libraries screened included known bioactive and commercial libraries from various sources (e.g., commercial libraries such as ChemDiv, ChemBridge, and Asinex; see attached pdf of all libraries). All libraries were owned and provided by the Institute of Chemistry and Cell Biology (ICCB)—Longwood (Harvard Medical School).

NF-kB-induced Luminescence Assay. THP1-Lucia cells between passage 15 and 18 and suspended in culture medium were dispensed into 384-well black clear-bottom plates (Corning 3712) at 30,000 cells/30 μl/well using a Combi liquid dispenser. To allow comparison to a benchmark small molecule with known immune stimulating activity, cells at the same concentration were stimulated with 50 μM R848, a TLR7/8 agonist, in 0.3% DMSO and added to every other well of column 24, which was left empty of cells, by multichannel pipette at the same volume. Five μl of 700 nM Phorbol myristate acetate (PMA) in THP1 culture media and 2.3% DMSO, a known peripheral blood cell mitogen, was added to every other well of column 23 by multichannel pipette (final concentration in well: 100 nM in 0.3% DMSO). Five μl of THP1 culture media with 2.3% DMSO was added to the remaining wells of column 23 by multichannel pipette (final concentration 0.3% DMSO). One hundred nl aliquots of library compounds diluted in 100% DMSO were transferred from their original 384-well plates to the assay plates using a Seiko pin transfer machine. Each library plate was pinned in duplicate, yielding two assay plates with identical conditions for comparison. Plates were then incubated for 24 hours at 37 C with 5% $CO_2$ in humid conditions. Following incubation, 10 μL of supernatant was removed from each well and transferred to a white plate (Corning 3570) using a Vprep liquid transfer machine. 10 μL of recombinant Lucia protein (Invivogen) diluted 1:2000 in THP1 culture media was added to empty well 24P. Using a Combi liquid dispenser, 50 μL/well of Quanti-Luc substrate (Invivogen) diluted 1:3 in sterile water was added to the assay plate. Immediately after adding the substrate, the luminescence was read using a PerkinElmer Envision plate reader.

THP1 Cell Adherence Assay. Following incubation and supernatant transfer described above, each black assay plate was manually washed. First, remaining suspension cells were expelled into a bath of 15% bleach by shaking the plate upside down. The plate was then submerged in a 7 L bath of 1×PBS. Once submerged, each plate was shaken vigorously side-to-side to release any air bubbles forming in the wells. The plate was then removed and shaken into the bleach bath once again. This process was repeated 3 times per plate. 30 μL/well of a mix of 2 μg/mL Hoechst 33342 in PBS with 1% Para-formaldehyde was added using a Combi liquid dispenser to the washed assay plates. Plates were left in the dark to stain and fix for 20 minutes. Washed and stained assay plates were then loaded onto an Acumen laser scanning cytometer. Total fluorescence area and number of objects (nuclei) were measured using the instrument for each well.

TNFαLISA Assay. Human adult peripheral blood was collected according to approved protocols. PBMCs were isolated from blood using a Ficoll density gradient. PBMCs were stored at $5 \times 10^7$ cells per vial in 1 mL RPMI containing 20% autologous plasma and 10% DMSO at −80° C. until use. On Day 1, PBMCs were thawed in 37° C. water bath for 3 min and washed twice with PBS. Viability was assessed by trypan blue staining and cells were then resuspended to $6.67 \times 10^5$ viable cells/mL in DMEM with 10% autologous plasma. 30 μl of cells were dispensed per well in Corning 2712 black 384-well cell culture plates (final concentration was 20,000 cells/well). Controls were added to cells manually and the test compounds were added by robotic pin transfer. Plates were then incubated at 37° C./5% $CO_2$ humidity-controlled incubator for 24 hours. On day 2 of the assay, plates were centrifuged and 2 µl supernatants were collected into Perkin Elmer Alpha plates. Perkin Elmer Human TNFα kits (cat #AL208F) were used to detect the presence of TNFα in supernatants. Plates were run on the EnVision (Perkin Elmer) instrument to detect light emission at 615 nm.

Hit Calling Method. Test compounds that resulted in a robust Z score>2 in both duplicates and at ≥2 of the 3 human samples of PBMCs were considered hits. The see following hit calling standard operating procedures (SOPs) were used for the THP-1 and TNFαLISA Assay::

All Data is log 10-transformed (log 10)—CrossTalk Corrected luminescence data from columns E, and F is log-transformed (log 10) in columns K, and L. Only experimental wells are evaluated, referencing column C with an "if" logic statement. An example of the calculation in column Q, log-transforming data from column E, is shown below:
=IF(C2="X",LOG 10(E2), " ")

A robust Z score is calculated for each experimental well with adjusted median absolute deviation (MAD) values. First, the plate median and MAD values are generated from the log-transformed data. The absolute deviation for each well value is calculated in columns M and N, an example of which is shown below:
=IF($C_2$="X", ABS(K2−$I$3), " ") wherein K2 is a log transformed data point, and 13 is the median value for that plate for that readout.

The MAD is then calculated as the median of each of columns U-X multiplied by 1.4286, an example of which is shown below:
=MEDIAN(M2:M385)*1.4286

The robust Z score is then calculated as (well_value−median_plate)/(MAD_plate*1.4286), an example calculation is shown below:
=IF($C2="X", ((K2−$I$3)/$I$5), " ") wherein K2 is a log-transformed well value, 13 is the plate experimental median for that readout, and 15 is the plate experimental MAD for that readout.

Any wells with robust Z score values of 2 or greater in both replicates are considered a hit. This is evaluated in column Q as shown in the example below:
=IF(AND((O2>$I$7), (P2>$J$7), ($C2="X")),TRUE, FALSE) wherein O2 and P2 are robust Z scores for replicates of the luminescence readout, while I7 and J7 represent the luminescence robust Z score threshold (2). "TRUE" will be returned in column Q if the compound meets these hit criteria.

For any well that is determined to be a hit, the Plate:Well compound ID will be displayed in column R as shown in the example below:
=IF(Q2,CONCATENATE(A2, ":",B2), " ") in which Q2 is the TRUE/FALSE value determining the hit status of the compound while A2 is the plate ID and B2 is the well ID.

Human MoDCs arrays. Heparinized human adult peripheral blood was layered onto Ficoll-Hypaque gradients (Ficoll-Paque PREMIUM, GE Healthcare, Waukesha, Wis.) blood mononuclear cell (PBMC's) layers. Monocytes were isolated from mononuclear cell fractions by positive selection with magnetic microbeads according to the manufacturer's instructions (Miltenyi Biotec, Auburn, Calif.) using CD14 as a pan-marker. Monocyte preparations were routinely >95% pure as assessed by flow cytometry for CD14 as previously described [1-5]. Isolated monocytes were cultured in tissue culture dishes at $0.4\times10^6$ cells/ml in RPMI 1640 medium containing fresh 10% autologous platelet-poor plasma, supplemented with recombinant human (rh) IL-4 (50 ng/ml) and rhGM-CSF (100 ng/ml) (R&D Systems, Minneapolis, Minn.) with one supplement of fresh medium and cytokines at day 3 of culture. After 5-6 days, immature MoDCs, routinely HLA-DR$^+$, CD14$^−$, DC-SIGN$^+$[3], of >90% purity were harvested by gently pipetting only the loosely adherent fraction and re-plated in a 96-well format at desired cell density.

ELISAs and Multiplex-Analyte Assays. Supernatants derived from human PBMCs and DC stimulations were assayed by ELISA for TNF (ThermoFisher Scientific; Waltham, Mass., USA). Cytokine and chemokine expression profiles (e.g., IFNγ, IL-9, IL-10, IL-12 (p70), IL-13, IL-1β, IL-23, IL-27, IL-28A, IL-33, IL-6, MIP-3α/CCL20, and TNF) in cell culture supernatants were measured using a customized Milliplex® Human Th17 Magnetic Bead Panel according to the manufacturer's instructions (Millipore, Chicago, Ill., USA). Assays were read and analyzed on the Luminex® 100/200™ System and xPOTENT® software (Luminex, Austin, Tex.). A minimum threshold was set at the minimum detectable concentration for each individual assay, defined as three standard deviations above the mean background.

In Vitro PBMC Stimulation.

PBMCs were isolated from blood using a Ficoll density gradient. PBMCs either used fresh or were stored at $5\times10^7$ cells per vial in 1 mL RPMI containing 20% autologous plasma and 10% DMSO at −80° C. until use. Stimulation plates were prepared by transferring 0.66 µl of DMSO-dissolved compounds (10 mM) to each well of a round bottom 96-well plate. PBMCs isolated from human adult donors were resuspended at a concentration of $10^5$ cells/200 µl of RPMI supplemented with 10% of platelet-poor plasma. 200 µl of the cell suspension were transferred to each well resulting in a final compound concentration of 33 M. After about 18 hours of incubation (37° C., 5% $CO_2$), plates were spun down (500×g, room temperature, 5 minutes) and supernatants were harvested for further analysis.

Newborn Whole Blood Assay

Human newborn cord blood was collected from term newborns (n=5) immediately after cesarean section using pyrogen-free heparin as anti-coagulant. Cord blood was diluted 1:1 (v/v) in RPMI 1640 medium. One microliter of each of the indicated compounds was added to each well containing 200 microliters of diluted blood in a 96-well round-bottomed plate at the final concentration of 11 µM. The plate was then incubated in the presence of 5% $CO_2$ at 37° C. in a humidified incubator for 18 hours. After ~18 hours of incubation (37° C., 5% $CO_2$), plates were spun down (500×g, room temperature, 5 minutes) and supernatants were harvested for further analysis.

Animals

C57BL/6 and BALB/c mice were obtained from Taconic Biosciences or Charles River Laboratories and housed in specific pathogen-free conditions in the animal research facilities at Boston Children's Hospital.

Splenocyte Isolation and In Vitro Stimulation

Spleens were harvested from 6-8 weeks old C57BL/6 mice. For splenocyte isolation, spleens were mashed through a 70 µM strainer, washed with PBS, and erythrocytes were lysed with 2 min of incubation in ammonium chloride-based lysis buffer (BD Biosciences). Cells were then counted and plated $2\times10^6$ per well (round bottom 96-well plate) in 200 µl of complete culture medium (RPMI 1640 plus 10% heat-inactivated fetal bovine serum [FBS, GE Healthcare HyClone], 50 µM 2-mercaptoethanol, 2 mM 1-glutamine, 100 U/ml penicillin/streptomycin [Gibco ThermoFisher Scientific]) with 0.66 µl of DMSO-dissolved compounds (10 mM) in order to achieve a final compound concentration of 33 µM. After 18 hours of incubation (37° C., 5% $CO_2$), plates were spun down (500×g, room temperature, 5 minutes) and supernatants were harvested for further analysis.

Antigens, Immunization and Antibody Quantification

For immunization experiments, adult mice were immunized intramuscularly (i.m.) in the right posterior thigh with 50 µl of vaccine containing 0.33 µg of each of the following recombinant influenza virus hemagglutinins (rHA): A/Michigan/45/2015 ($H_1N_1$), A/Hong Kong/4801/2014 (H3N2), and B/Brisbane/60/2008, contained in the 2016-2017 formulation of the FluBlok vaccine (Protein Sciences Corp.). Mice were immunized with a prime-boost schedule (two injections four weeks apart). Vaccine in all experimental groups was formulated with 10% (v/v) DMSO (except for the groups immunized with the small molecules since they were dissolved in DMSO) and 5% (v/v) Tween-80. As indicated for specific experimental groups, vaccine was also formulated with Aluminium hydroxide (100 µg) and/or compound 037 (100 nmol, final DMSO concentration 10%). Serum was collected 28 days post-prime (pre-boost blood sample) and 14 days post-boost for antibody detection. rHA-specific IgG were quantified by ELISA. High binding flat bottom 96-well plates (Corning Life Sciences) were coated with 1 µg/ml rHA in carbonate buffer pH 9.6, incubated overnight at 4° C. and blocked with PBS+BSA 1% (Sigma-Aldrich) for 1 h at room temperature (RT). Then, sera from vaccinated mice were added with an initial dilution of 1:100 and 1:4 serial dilutions in PBS+BSA 1% and incubated for 2 h at RT. Plates were then washed and incubated for 1 h at RT with HRP-conjugated anti-mouse IgG (Southern Biotech). At the end of the incubation plates were washed again and developed with tetramethylbenzidine (BD Biosciences) for 5 minutes, then stopped with 1 N $H_2SO_4$. The optical density was read at 450 nm Versamax microplate reader with SoftMax Pro Version 5 (both from Molecular Devices) and endpoint titers were calculated using as cutoff three times the optical density of the background.

Statistical analysis. Statistical significance and graphic output were generated using Prism v. 5.0b (GraphPad Software) and Microsoft Excel (Microsoft Corporation, Redmond, Wash.). Results were considered significant at p values<0.05, and indicated as follows: * $p<0.05$,  $p<0.01$, * $p<0.001$.

REFERENCES

1. Dowling, D. J., et al., The ultra-potent and selective TLR8 agonist VTX-294 activates human newborn and adult leukocytes. PLoS One, 2013. 8(3): p. e58164.
2. Palmer, C. D., et al., The effect of stable macromolecular complexes of ionic polyphosphazene on HIV Gag antigen and on activation of human dendritic cells and presentation to T-cells. Biomaterials, 2014. 35(31): p. 8876-86.
3. Philbin, V. J., et al., Imidazoquinoline Toll-like receptor 8 agonists activate human newborn monocytes and dendritic cells through adenosine-refractory and caspase-1-dependent pathways. J Allergy Clin Immunol, 2012. 130 (1): p. 195-204 e9.
4. Ganapathi, L., et al., The Imidazoquinoline Toll-Like Receptor-7/8 Agonist Hybrid-2 Potently Induces Cytokine Production by Human Newborn and Adult Leukocytes. PLoS One, 2015. 10(8): p. e0134640.
5. Dowling, D. J., et al., Toll-like receptor 8 agonist nanoparticles mimic immunomodulating effects of the live BCG vaccine and enhance neonatal innate and adaptive immune responses. J Allergy Clin Immunol, 2017.
6. Dowling, D. J., et al., TLR7/8 adjuvant overcomes newborn hyporesponsiveness to pneumococcal conjugate vaccine at birth, *JCI Insight.* 2017; 2(6).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but

What is claimed is:

1. A compound of Formula (I):

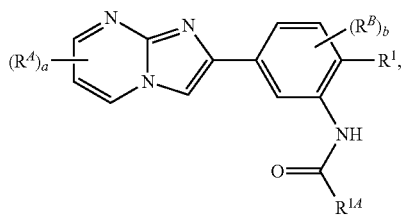

(I)

or a pharmaceutically acceptable salt thereof, wherein:
  $R^{14}$ is substituted or unsubstituted phenyl or substituted or unsubstituted benzyl, or substituted or unsubstituted 6-membered heteroaryl;
  $R^1$ is halogen, substituted or unsubstituted $C_{1-6}$ alkyl, —$OR^a$, or —$N(R^{a1})_2$;
  each instance of $R^A$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^{a1})_2$, —$SR^a$, —CN, —C(=O)$R^a$, —C(=O)$OR^a$, —C(=O)$N(R^{a1})_2$, or —$NO_2$;
  each instance of $R^B$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^{a1})_2$, —$SR^a$, —CN, —C(=O)$R^a$, —C(=O)$OR^a$, —C(=O)$N(R^{a1})_2$, or —$NO_2$;
  each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom;
  each instance of $R^{a1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or two instances of $R^{a1}$ are joined to form a substituted or unsubstituted, heterocyclic ring, or substituted or unsubstituted, heteroaryl ring;
  a is 1, 2, or 3; and
  b is 0, 1, 2, or 3.

2. The compound of claim 1, wherein the compound is of the formula:

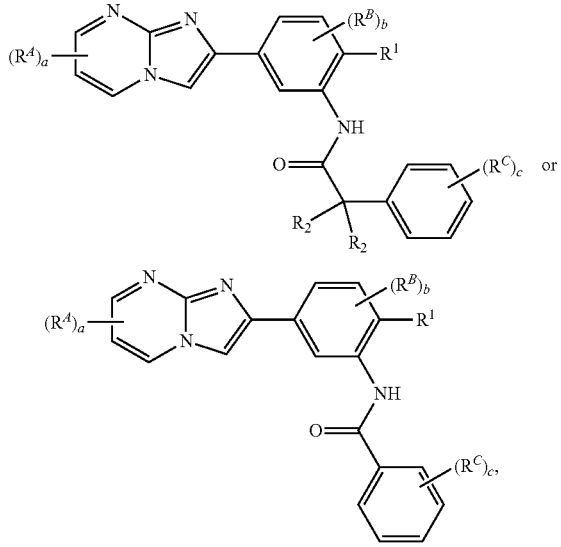

or a pharmaceutically acceptable salt thereof, wherein:
  each instance of $R^2$ is independently hydrogen, halogen, substituted or unsubstituted $C_{1-6}$ alkyl, —$OR^a$, or —$N(R^{a1})_2$;
  each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^{a1})_2$, —$SR^a$, —CN, —C(=O)$R^a$, —C(=O)$OR^a$, —C(=O)$N(R^{a1})_2$, or —$NO_2$; and
  c is 0, 1, 2, 3, 4, or 5.

3. The compound of claim 1, wherein $R^1$ is halogen or substituted or unsubstituted $C_{1-6}$ alkyl.

4. The compound of claim 1, wherein $R^{14}$ is of the formula:

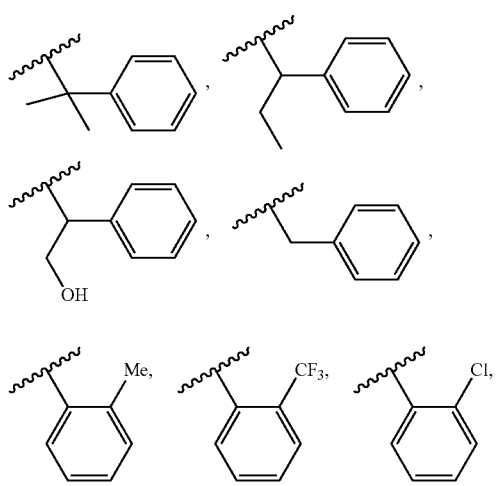

119

-continued

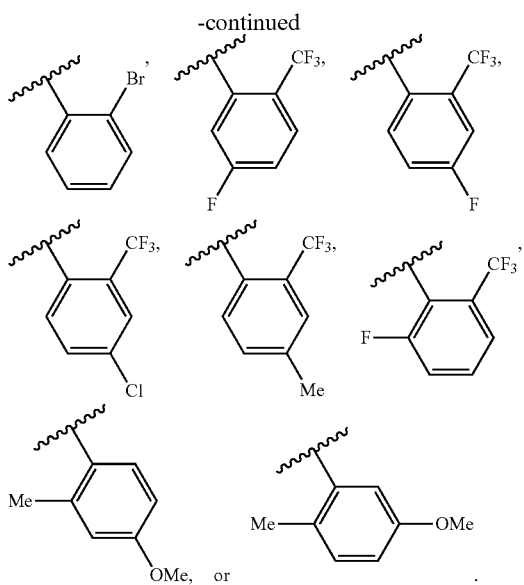

5. The compound of claim 2, wherein at least one instance of $R^2$ is substituted or unsubstituted $C_{1-6}$ alkyl.

6. The compound of claim 5, wherein at least one instance of $R^2$ is Me or Et.

7. The compound of claim 1, wherein $R^A$ is halogen, substituted or unsubstituted $C_{1-6}$ alkyl, or —O (substituted or unsubstituted $C_{1-6}$ alkyl).

8. The compound of claim 7, wherein $R^A$ is —F, Me, or —OMe.

9. The compound of claim 1, wherein a is 1.

10. The compound of claim 1, wherein b is 0.

11. The compound of claim 2, wherein c is 0.

12. The compound of claim 2, wherein c is 1.

13. The compound of claim 2, wherein $R^C$ is halogen or substituted or unsubstituted $C_{1-6}$ alkyl.

14. The compound of claim 1, wherein the compound is of the formula:

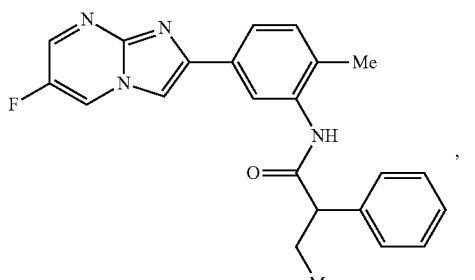

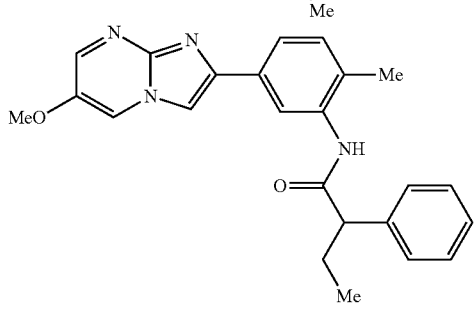

120

-continued

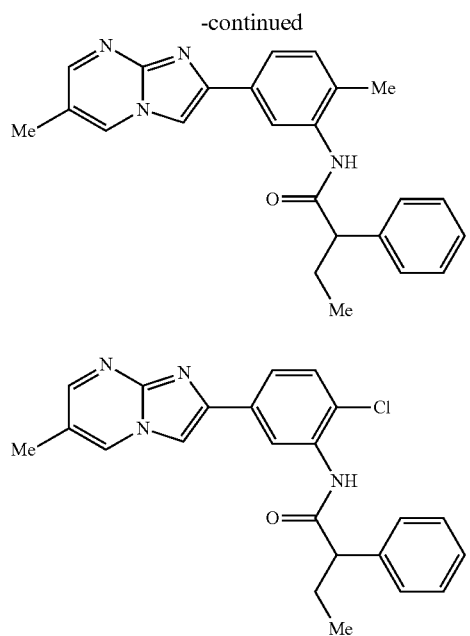

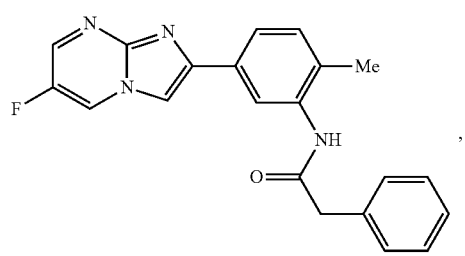

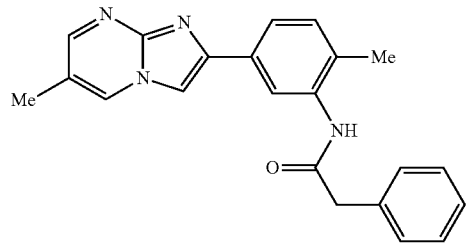

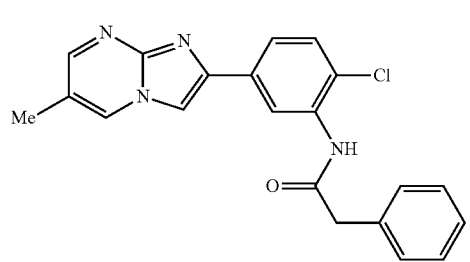

121
-continued
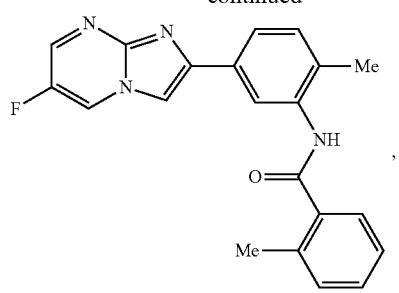
,
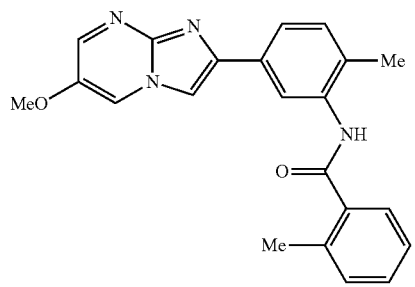
,
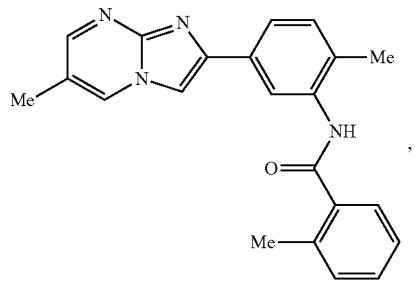
,
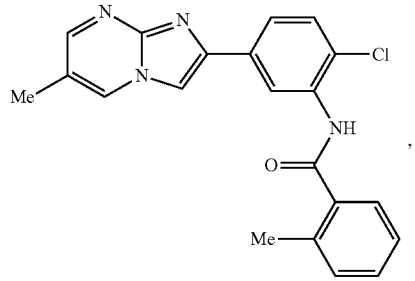
,
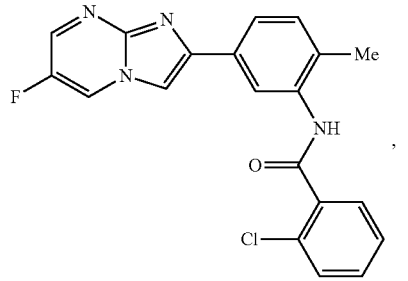
,
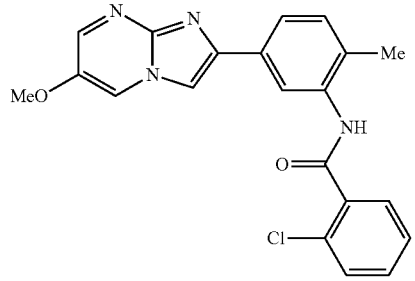
,
122
-continued
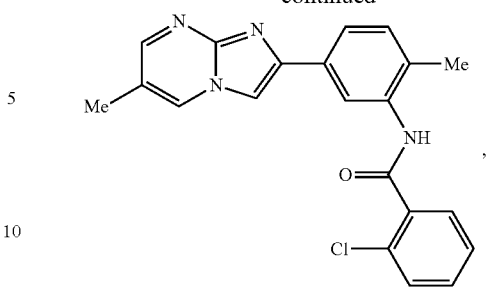
,
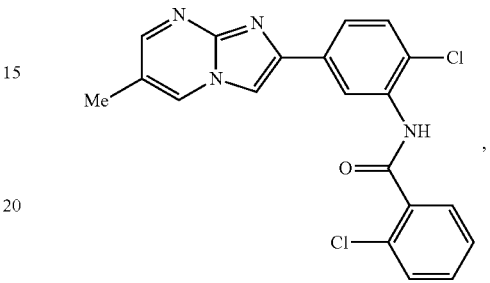
,
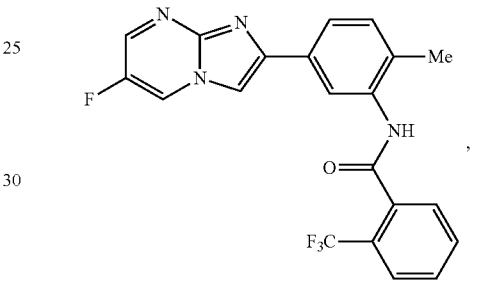
,
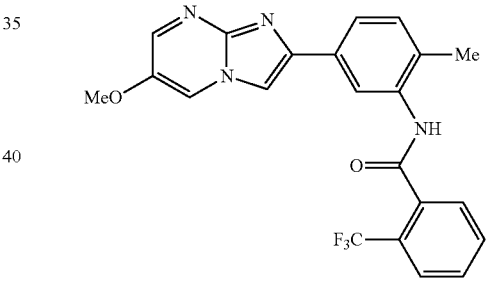
,
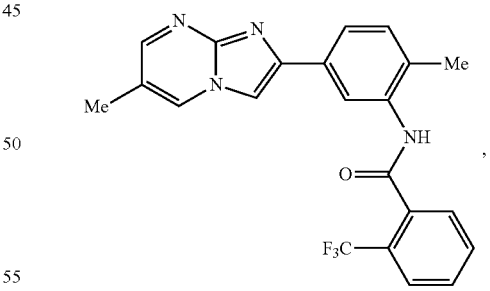
,
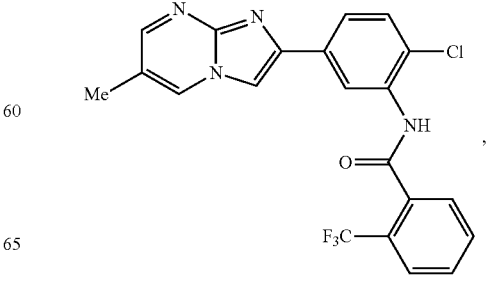
, 123
-continued
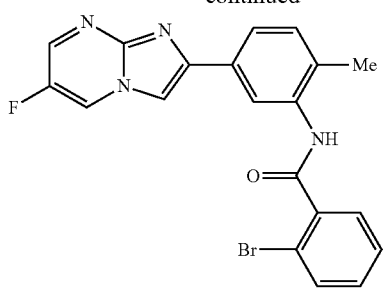
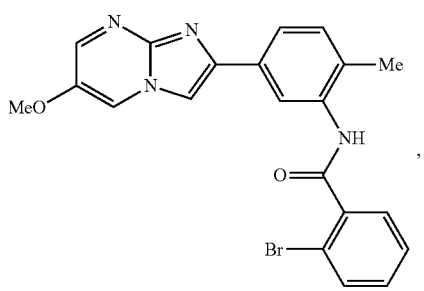
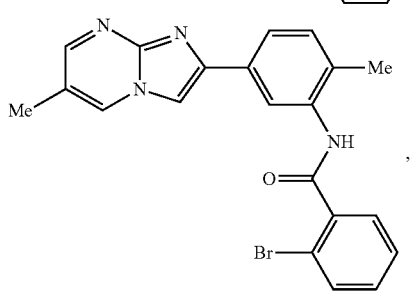
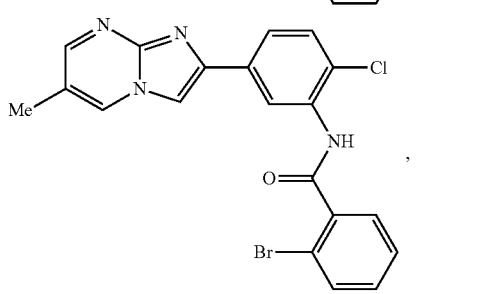
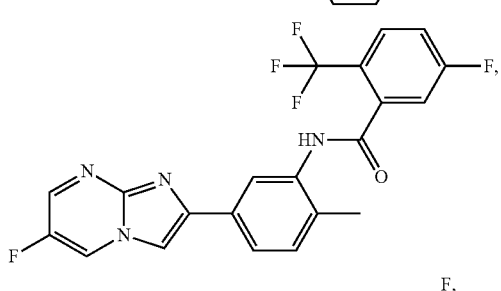
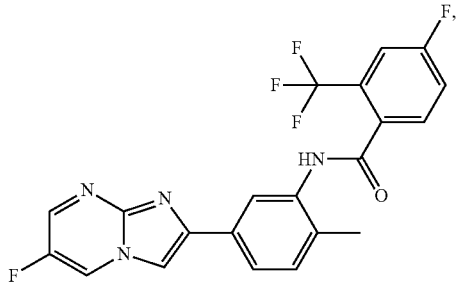
124
-continued
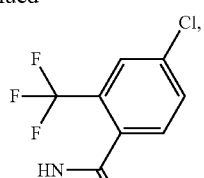
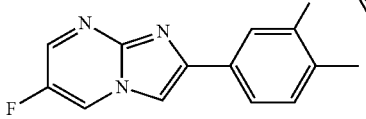
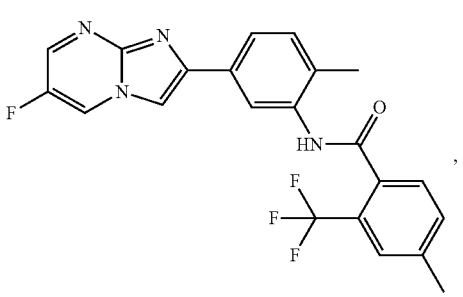
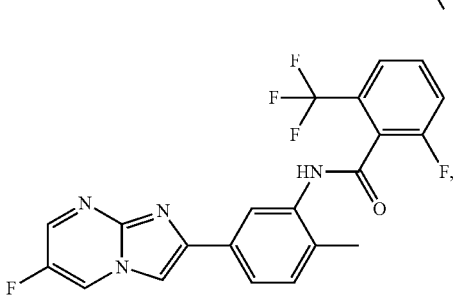
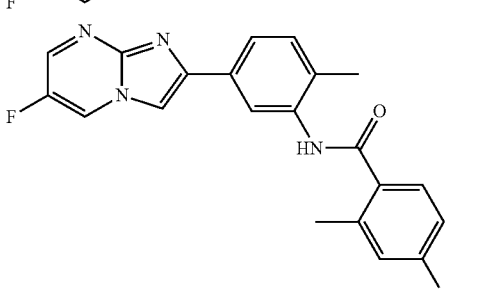
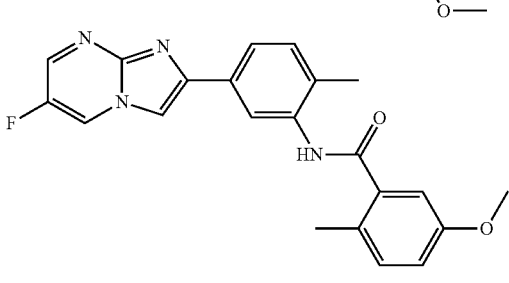
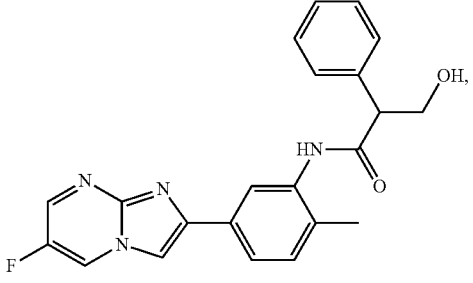

-continued

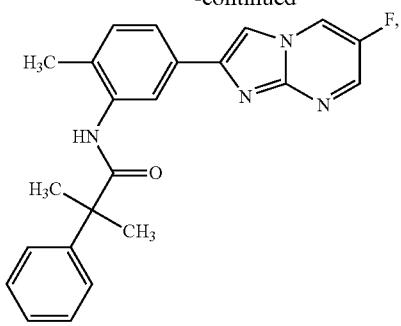

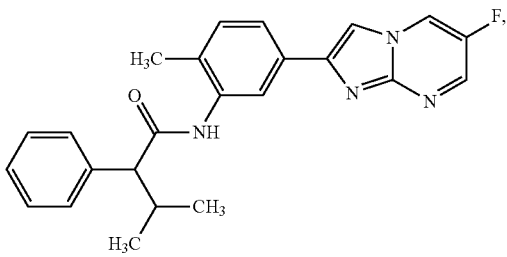

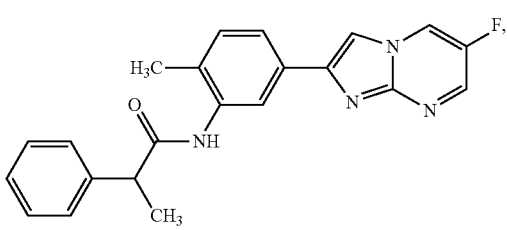

or a pharmaceutically acceptable salt thereof.

15. A pharmaceutical composition comprising a compound of claim 1, and a pharmaceutically acceptable excipient.

16. The compound of claim 1, wherein $R^{1A}$ is of formula:

wherein:

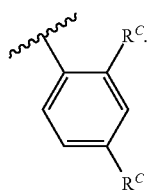

each instance of $R^c$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^{a1}$)$_2$, —SR$^a$, —CN, —C(=O)R$^a$, —C(=O)OR$^a$, —C(=O)N(R$^{a1}$)$_2$, or —NO$_2$.

17. The compound of claim 2, wherein the compound is of the formula:

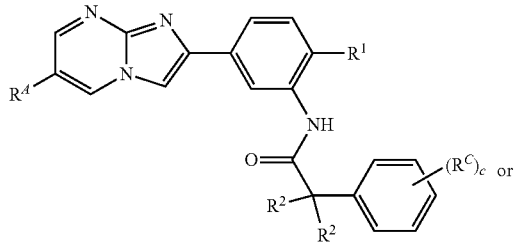

or a pharmaceutically acceptable salt thereof.

18. The compound of claim 2, wherein the compound is of the formula:

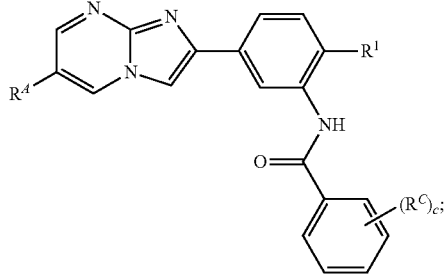

or a pharmaceutically acceptable salt thereof.

19. The compound of claim 2, wherein the compound is of the formula:

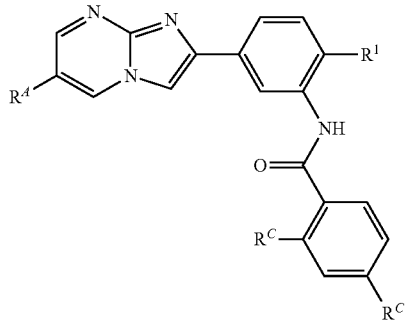

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 11,673,891 B2 | Page 1 of 1 |
| APPLICATION NO. | : 16/764171 | |
| DATED | : June 13, 2023 | |
| INVENTOR(S) | : Ofer Levy et al. | |

It is certified that error appears in the above-identified patent and that said Letters Patent is hereby corrected as shown below:

In the Specification

At Column 1, Line 15, please replace the paragraph titled "GOVERNMENT SUPPORT" with the following paragraph:
FEDERALLY SPONSORED RESEARCH
This invention was made with government support under Contract Number HHSN272201400052C, awarded by the National Institutes of Health. The Government has certain rights in the invention.

Signed and Sealed this
Eighth Day of August, 2023

Katherine Kelly Vidal
*Director of the United States Patent and Trademark Office*